US010428157B2

(12) United States Patent
Baccara-Dinet et al.

(10) Patent No.: US 10,428,157 B2
(45) Date of Patent: Oct. 1, 2019

(54) DOSING REGIMENS FOR USE WITH PCSK9 INHIBITORS

(71) Applicants: Sanofi Biotechnology, Paris (FR); Regeneron Pharmaceuticals, Inc., Tarrytown, NY (US)

(72) Inventors: Marie Baccara-Dinet, Paris (FR); Laurence Bessac, Paris (FR); Corinne Hanotin, Paris (FR); Robert C. Pordy, Tarrytown, NY (US); William J. Sasiela, Tarrytown, NY (US); Jacques Rey, Paris (FR)

(73) Assignees: SANOFI BIOTECHNOLOGY, Paris (FR); REGENERON PHARMACEUTICALS, INC., Tarrytown, NY (US)

( * ) Notice: Subject to any disclaimer, the term of this patent is extended or adjusted under 35 U.S.C. 154(b) by 1140 days.

(21) Appl. No.: 14/539,199

(22) Filed: Nov. 12, 2014

(65) Prior Publication Data

US 2015/0152191 A1 Jun. 4, 2015

Related U.S. Application Data

(60) Provisional application No. 61/955,337, filed on Mar. 19, 2014, provisional application No. 61/902,857, filed on Nov. 12, 2013.

(30) Foreign Application Priority Data

Jul. 31, 2014 (EP) .................................... 14306222

(51) Int. Cl.
*C07K 16/40* (2006.01)
*A61K 39/00* (2006.01)

(52) U.S. Cl.
CPC ........ *C07K 16/40* (2013.01); *A61K 2039/505* (2013.01); *A61K 2039/545* (2013.01); *C07K 2317/21* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,260,440 A | 11/1993 | Hira et al. | |
| 5,273,995 A | 12/1993 | Roth | |
| 5,399,670 A | 3/1995 | Bhattacharya et al. | |
| 5,851,999 A | 12/1998 | Ulrich et al. | |
| 5,939,598 A | 8/1999 | Kucherlapati | |
| 6,011,003 A | 1/2000 | Charnock-Jones et al. | |
| 6,171,586 B1 | 1/2001 | Lam et al. | |
| 6,267,958 B1 | 7/2001 | Andya et al. | |
| 6,270,993 B1 | 8/2001 | Shibuya et al. | |
| 6,596,541 B2 | 7/2003 | Murphy | |
| 6,629,949 B1 | 10/2003 | Douglas | |
| 6,659,982 B2 | 12/2003 | Douglas et al. | |
| 6,875,432 B2 | 4/2005 | Liu et al. | |
| 7,001,892 B1 | 2/2006 | Chmielweski et al. | |
| 7,029,895 B2 | 4/2006 | Glucksmann et al. | |
| 7,060,268 B2 | 6/2006 | Andya et al. | |
| 7,129,338 B1 | 10/2006 | Ota et al. | |
| 7,300,754 B2 | 11/2007 | Fadel et al. | |
| 7,482,147 B2 | 1/2009 | Glucksmann et al. | |
| 7,572,618 B2 | 8/2009 | Mintier et al. | |
| 7,608,693 B2 | 10/2009 | Martin et al. | |
| 7,754,208 B2 | 7/2010 | Ledbetter et al. | |
| 8,030,457 B2 | 10/2011 | Jackson et al. | |
| 8,062,640 B2 | 11/2011 | Sleeman et al. | |
| 8,080,243 B2 | 12/2011 | Liang et al. | |
| 8,092,803 B2 | 1/2012 | Furfine et al. | |
| 8,168,762 B2 | 5/2012 | Jackson et al. | |
| 8,188,233 B2 | 5/2012 | Condra et al. | |
| 8,188,234 B2 | 5/2012 | Condra et al. | |
| 8,357,371 B2 | 1/2013 | Sleeman et al. | |
| 8,501,184 B2 | 8/2013 | Sleeman et al. | |
| 8,748,115 B2 | 6/2014 | Ni et al. | |
| 8,795,669 B2 | 8/2014 | Walsh et al. | |
| 8,883,157 B1 | 11/2014 | Clube | |
| 9,034,332 B1 | 5/2015 | Clube | |
| 9,193,801 B2 | 11/2015 | Walsh et al. | |
| 9,540,449 B2 | 1/2017 | Yancopoulos et al. | |
| 9,561,155 B2 | 2/2017 | Hanotin et al. | |
| 9,682,013 B2 | 6/2017 | Hanotin et al. | |
| 9,724,411 B2 | 8/2017 | Sleeman et al. | |
| 2003/0092606 A1 | 5/2003 | L'italien et al. | |
| 2003/0113316 A1 | 6/2003 | Kaisheva et al. | |

(Continued)

FOREIGN PATENT DOCUMENTS

CN 101489565 A 7/2009
EP 0521471 B1 10/2000

(Continued)

OTHER PUBLICATIONS

Bambauer et al. (2003) "Low-density Lipoprotein Apheresis: An Overview," Therapeutic Apheresis and Dialysis. 7 (4):382-390.
Beliard et al. (Mar. 3, 2014) "Improvement in LDL-cholesterol levels of patients with familial hypercholesterolemia: can we do better? Analysis of results obtained during the past two decades in 1669 French subjects," Atherosclerosis. 234:136-141.
Berthold et al. (Jan. 2013) "Hyperlipoproteinemia(a): Clinical significance and treatment options," Atherosclerosis Supplements 14:1-5.
Borberg (Apr. 2013) "The lower the better: Target values after LDL-Apheresis and semi-selective LDL-elimination therapies," Transfusion and Apheresis Science. 48:203-206.

(Continued)

*Primary Examiner* — Sharon X Wen
(74) *Attorney, Agent, or Firm* — Lathrop Gage LLP; James H. Velema, Esq.

(57) ABSTRACT

The present invention provides methods for treating a PCSK9-mediated disease or a PCSK9-mediated condition. Specifically, the invention relates to methods comprising the administration of a proprotein convertase subtilisin/kexin type 9 (PCSK9) antibody or antigen binding protein, in the absence of a statin, to a subject in need thereof.

13 Claims, 9 Drawing Sheets

Specification includes a Sequence Listing.

(56) References Cited

U.S. PATENT DOCUMENTS

| | | |
|---|---|---|
| 2003/0118592 A1 | 6/2003 | Ledbetter et al. |
| 2003/0133939 A1 | 7/2003 | Ledbetter et al. |
| 2004/0101920 A1 | 5/2004 | Radziejewski et al. |
| 2004/0197324 A1 | 10/2004 | Liu et al. |
| 2005/0281831 A1 | 12/2005 | Davis-Smyth et al. |
| 2006/0147945 A1 | 7/2006 | Edmonds et al. |
| 2007/0082345 A1 | 4/2007 | Ota et al. |
| 2007/0224663 A1 | 9/2007 | Rosen et al. |
| 2008/0008697 A1 | 1/2008 | Mintier et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0269350 A1 | 10/2009 | Glucksmann et al. |
| 2009/0318536 A1 | 12/2009 | Freier et al. |
| 2009/0326202 A1 | 12/2009 | Jackson et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068199 A1 | 3/2010 | Liang et al. |
| 2010/0136028 A1 | 6/2010 | Sparrow et al. |
| 2010/0150937 A1 | 6/2010 | Sparrow et al. |
| 2010/0166768 A1 | 7/2010 | Sleeman et al. |
| 2010/0233177 A1 | 9/2010 | Yowe et al. |
| 2011/0027287 A1 | 2/2011 | Jackson et al. |
| 2011/0033465 A1 | 2/2011 | Hedrick et al. |
| 2011/0065902 A1 | 3/2011 | Sleeman et al. |
| 2011/0098450 A1 | 4/2011 | Igawa et al. |
| 2011/0111406 A1 | 5/2011 | Igawa et al. |
| 2011/0142849 A1 | 6/2011 | Rue et al. |
| 2011/0171241 A1 | 7/2011 | Dix et al. |
| 2011/0229489 A1 | 9/2011 | Pons et al. |
| 2011/0256148 A1 | 10/2011 | Sleeman et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0093818 A1 | 4/2012 | Jackson et al. |
| 2012/0097565 A1 | 4/2012 | Dix et al. |
| 2012/0195910 A1 | 8/2012 | Wu et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2013/0011866 A1 | 1/2013 | Igawa et al. |
| 2013/0064825 A1 | 3/2013 | Chan et al. |
| 2013/0064834 A1 | 3/2013 | Sleeman et al. |
| 2013/0085266 A1 | 4/2013 | Sleeman et al. |
| 2013/0189277 A1 | 7/2013 | Walsh et al. |
| 2013/0243784 A1 | 9/2013 | Swergold |
| 2013/0245235 A1 | 9/2013 | Jackson et al. |
| 2014/0004122 A1 | 1/2014 | Chan et al. |
| 2014/0030270 A1 | 1/2014 | Clogston et al. |
| 2014/0065649 A1 | 3/2014 | Schafer et al. |
| 2014/0099312 A1 | 4/2014 | Sleeman et al. |
| 2014/0154262 A1 | 6/2014 | Hanotin et al. |
| 2014/0161821 A1 | 6/2014 | Udata |
| 2014/0178402 A1 | 6/2014 | Hanotin et al. |
| 2014/0341928 A1 | 11/2014 | Walsh et al. |
| 2014/0356370 A1 | 12/2014 | Swergold et al. |
| 2014/0356371 A1 | 12/2014 | Swergold et al. |
| 2015/0140002 A1 | 5/2015 | Baccara-Dinet et al. |
| 2015/0283236 A1 | 10/2015 | Baccara-Dinet et al. |
| 2015/0284473 A1 | 10/2015 | Bessac et al. |
| 2015/0284474 A1 | 10/2015 | Sleeman et al. |
| 2016/0032015 A1 | 2/2016 | Walsh et al. |
| 2016/0115246 A1 | 4/2016 | Sasiela et al. |
| 2016/0137745 A1 | 5/2016 | Baccara-Dinet et al. |
| 2016/0137746 A1 | 5/2016 | Hanotin et al. |
| 2016/0152734 A1 | 6/2016 | Udata |
| 2017/0266079 A1 | 9/2017 | Hanotin et al. |

FOREIGN PATENT DOCUMENTS

| | | |
|---|---|---|
| EP | 1067182 A2 | 1/2001 |
| EP | 0409281 B1 | 10/2001 |
| EP | 1514933 A1 | 3/2005 |
| EP | 1317537 B1 | 12/2006 |
| EP | 1618212 B1 | 11/2007 |
| EP | 2 703 008 A1 | 3/2014 |
| EP | 2 703 009 A1 | 3/2014 |
| EP | 2 706 070 A1 | 3/2014 |
| WO | 1993/000807 A1 | 1/1993 |
| WO | 1997/035620 A1 | 10/1997 |
| WO | 1998/022136 A2 | 5/1998 |
| WO | 1999/038495 A2 | 8/1999 |
| WO | 2001057081 A2 | 8/2001 |
| WO | 2004/055164 A2 | 7/2004 |
| WO | 2005103081 A2 | 11/2005 |
| WO | 2007/143315 A2 | 12/2007 |
| WO | 2007/149334 A2 | 12/2007 |
| WO | 2008057457 A2 | 5/2008 |
| WO | 2008057458 A2 | 5/2008 |
| WO | 2008057459 A2 | 5/2008 |
| WO | 2008063382 A2 | 5/2008 |
| WO | 2008125623 A2 | 10/2008 |
| WO | 2008133647 A2 | 11/2008 |
| WO | 2009026558 A1 | 2/2009 |
| WO | 2009055783 A2 | 4/2009 |
| WO | 2009100297 A1 | 8/2009 |
| WO | 2009100318 A1 | 8/2009 |
| WO | 2010/032220 A1 | 3/2010 |
| WO | 2010029513 A2 | 3/2010 |
| WO | 2010077854 A1 | 7/2010 |
| WO | 2010/102241 A1 | 9/2010 |
| WO | 2010/148337 A1 | 12/2010 |
| WO | 2011028938 A1 | 3/2011 |
| WO | 2011039578 A1 | 4/2011 |
| WO | 2011/053759 A1 | 5/2011 |
| WO | 2011/061712 A1 | 5/2011 |
| WO | 2011/072263 A1 | 6/2011 |
| WO | 2011/111007 A2 | 9/2011 |
| WO | 2011/117401 A1 | 9/2011 |
| WO | 2012054438 A1 | 4/2012 |
| WO | 2012064792 A2 | 5/2012 |
| WO | 2012101251 A1 | 8/2012 |
| WO | 2012101252 A1 | 8/2012 |
| WO | 2012101253 A1 | 8/2012 |
| WO | 2012109530 A1 | 8/2012 |
| WO | 2012146776 A1 | 11/2012 |
| WO | 2012154999 A1 | 11/2012 |
| WO | 2013/039958 A1 | 3/2013 |
| WO | 2013039969 A1 | 3/2013 |
| WO | 2013/158984 A1 | 10/2013 |
| WO | 2013/166448 A1 | 11/2013 |
| WO | 2014/194111 A1 | 12/2014 |
| WO | 2014/197752 A1 | 12/2014 |
| WO | 2015/054619 A2 | 4/2015 |
| WO | 2015/073494 A1 | 5/2015 |
| WO | 2015/123423 A2 | 8/2015 |
| WO | 2015/140079 A1 | 9/2015 |
| WO | 2015/142668 A1 | 9/2015 |
| WO | 2016/011256 A1 | 1/2016 |
| WO | 2016/011260 A1 | 1/2016 |

OTHER PUBLICATIONS

Demant et al. (2001) "The metabolism of lipoprotein(a) and other apolipoprotein B-containing lipoproteins: a kinetic study in humans," Atherosclerosis 157:325-339.

Huijgen et al. (2010) "Two years after molecular diagnosis of familial hypercholesterolemia: majority on cholesterol-lowering treatment but a minority reaches treatment goal," PLoS One. 5(2):e9220. pp. 1-7.

Koschinsky et al. (2009) Clinical Lipidology: A Companion to Braunwald's Heart Disease. Ed: Ballantyne. pp. 136-143.

Leebmann et al. (Dec. 17, 2013) Circulation "Lipoprotein Apheresis in Patients With Maximally Tolerated Lipid-Lowering Therapy, Lipoprotein(a)-Hyperlipoproteinemia, and Progressive Cardiovascular Disease," Circulation. 128 (24):2567-2576.

(56) References Cited

OTHER PUBLICATIONS

McPherson (2013) "Remnant Cholesterol: Non-(HDL-C + LDL-C) as a Coronary Artery Disease Risk Factor," Journal of the American College of Cardiology. 61(4):437-439.
Moon (2007) "Lipoprotein(a) and LDL Particle Size are Related to the Severity of Coronary Artery Disease", Cardiology 108:282-289.
Neil et al. (2004) "Established and emerging coronary risk factors in patients with heterozygous familial hypercholesterolaemia," Heart 90(12):1431-1437.
Pijlman et al. (2010) "Evaluation of cholesterol lowering treatment of patients with familial hypercholesterolemia: a large cross-sectional study in The Netherlands," Atherosclerosis. 209:189-194.
Regeneron and Sanofi (Nov. 5, 2012) "IR Conference Call on PCSK9: SAR236553/REGN727 PCSK9 Antibody for Hypercholesterolemia Phase 3 ODYSSEY Program Underway," Accessible on the Internet at URL: www.sanofi.com/Images/31341_2012-11-05_PCSK9_call.pdf. pp. 1-30. [Last Accessed on Sep. 5, 2017].
Robinson et al. (2013) "Management of Familial Hypercholesterolemia: A Review of the Recommendations from the National Lipid Association Expert Panel on Familial Hypercholesterolemia," J. Manag. Care Pharm. 19(2):139-149.
Saeedi et al. (Mar. 31, 2016) "Lipoprotein (a), an independent cardiovascular risk marker," Clinical Diabetes and Endocrinology. 2:7 pp. 1-6.
Sahebkar et al. (Aug. 8, 2013) "New LDL-Cholesterol Lowering Therapies: Pharmacology, Clinical Trials, and Relevance to Acute Coronary Syndromes," Clinical Therapeutics. 35(8):1082-1098.
Shoji et al. (1998) "Intermediate-Density Lipoprotein as an Independent Risk Factor for Aortic Atherosclerosis in Hemodialysis Patients," J. Am. Soc. Nephrol. 9:1277-1284.
Stone et al. (2014) "2013 ACC/AHA Guideline on the Treatment of Blood Cholesterol to Reduce Atherosclerotic cardiovascular Risk in Adults," Circulation. 129:S1-S48.
Tavori et al. (Oct. 11, 2013) "Loss of Plasma Proprotein Convertase Subtilisin/Kevin 9 (PCSK9) After Lipoprotein Apheresis," Circulation Research. 113(12):1290-1295.
Thompsen et al. (2006) "A systematic review of LDL apheresis in the treatment of cardiovascular disease," Atherosclerosis. 189:31-38.
Van Wissen et al. (2003) "Long term statin treatment reduces lipoprotein(a) concentrations in heterozygous familial hypercholesterolaemia," Heart 89(8):893-896.
Walji (2013) "Lipoprotein Apheresis for the Treatment of Familial Hypercholesterolemia," Clinical Lipidology. 8 (5):573-586.
Park et al., 'Lipids and Lipoproteins: Post-transcriptional Regulation of Low Density Lipoprotein Receptor Protein by Proprotein Convertase Subtilisin/Kexin Type 9a in Mouse Liver.' J. Biol. Chem. 2004, 279: 50630-50638.
Partial International Search Report dated Nov. 6, 2014 for International Application No. PCT/US2014/040163.
Pfizer: 'Safety and Tolerability of Multiple Doses of PF-04950615 (RN316) In Subjects With Hypercholesterolemia.' Nov. 3, 2012, XP002682100. Retrieved from the Internet: URL:http://clinicaltrials.gov/ct2/show?term=rn316&rank=2.
Pearson, William R., 'Using the FASTA program to search protein and DNA sequence databases.' Computer Analysis of Sequence Data. 1994, pp. 307-331.
Powell et al., 'Compendium of Excipients for Parenteral Formulations PDA' Journal of Pharmaceutical Science and Technology. 1998, vol. 52, No. 5, pp. 238-311.
Qiu et al., 'Small antibody mimetics comprising two complementarity-determining regions and a framework region for tumor targeting.' Nature Biotechnology. 2007, vol. 25, No. 8, pp. 921-929.
Reddy et al., 'Elimination of Fc receptor-dependent effector functions of a modified IgG4 monoclonal antibody to human CD4.' The Journal of Immunology. 2000, vol. 164, No. 4, pp. 1925-1933.
Reineke, Ulrich, 'Antibody epitope mapping using arrays of synthetic peptides.' Antibody Engineering. Humana Press. 2004, pp. 443-463.
Rhainds et al., 'PCSK9 inhibition and LDL cholesterol lowering: The biology of an attractive therapeutic target and critical review of the latest clinical trials.' Clinical Lipidology. 2012, 7(6):621-640.
Rashid et al., 'Decreased plasma cholesterol and hypersensitivity to statins in mice lacking Pcsk9.' PNAS. 2005, 102(15):5374-5379.
Sarkar et al., 'Rational cytokine design for increased lifetime and enhanced potency using pH-activated "histidine switching".' Nature Biotechnology. 2002, 20:908-913.
Sefton, Michael V. 'Implantable Pumps.' Critical Reviews in Biomedical Engineering. 1987, vol. 14, No. 3, pp. 201-240.
Seidah et al., 'The secretory proprotein convertase neural apoptosis-regulated convertase 1 (NARC-1): liver regeneration and neuronal differentiation.' PNAS. 2003,100(3):928-933.
Shields et al., 'Lack of fucose on human IgG1 N-linked oligosaccharide improves binding to human FcγRIII and antibody-dependent cellular toxicity.' Journal of Biological Chemistry. 2002, vol. 277, No. 30, pp. 26733-26740.
Soutar, Anne, 'Unexpected Roles for PCSK9 in Lipid Metabolism.' Current Opinion in Lipodology. 2011, vol. 22, pp. 192-196.
Stein et al., 'Potential of proprotein Convertase Subtilisin/Kexin Type 9 Based Therapeutics.' Current Atherosclerosis Reports. 2013, 15(310):1-14.
Stein et al., 'Effect of a monoclonal antibody to PCSK9 on LDL cholesterol.' Obstetrical and Gynecological Survey. 2012, 67(7):413-414.
Stein et al., 'Effect of a Monoclonal Antibody to PCSK9 on D Cholesterol.' New England Journal of Medicine. 2012, 366:1108-1118.
Stein et al., 'Effect of a monoclonal antibody to PCSK9, REGN727/SAR236553, to reduce low-density lipoprotein cholesterol in patients with heterozygofamilial hypercholesterolemia on stable statin dose with or without ezetimibe therapy: a phase 2 randomized controlled trial.' The Lancet. 2012, 380:29-36.
Timms et al., 'A mutation in PCSK9 causing autosomal-dominant hypercholesterolemia in a Utah pedigree.' Human Genetics. 2004, 114(4):349-353.
Tiwari et al., 'Statins therapy: a review on conventional and novel formulation approaches.' Journal of Pharmacy and Pharmacology. 2011, vol. 63, No. 8, pp. 983-998.
Toth et al., 'Alirocumab, a Proprotein Convertase Substilisin/Kexin Type 9 Monoclonal Antibody, Reduces Cholesterol Concentrations of Serum Remnant Lipoprotein Fractions, Very Low-Density Lipoproteins and Triglycerides.' Circulation. 2013, 128(22):17492.
Tutt et al., 'Trispecific F (ab') 3 derivatives that use cooperative signaling via the TCR/CD3 complex and CD2 to activate and redirect resting cytotoxic T cells.' The Journal of Immunology. 1991, vol. 147, No. 1, pp. 60-69.
Vajdos et al., 'Comprehensive functional maps of the antigen-binding site of an anti-ErbB2 antibody obtained with shotgun scanning mutagenesis.' Journal of Molecular Biology. 2002, vol. 320, No. 2, pp. 415-428.
Varbo et al., 'Remnant Cholesterol as a Casual Risk Factor for Ischemic Heart Disease.' Journal of the American College of Cardiology. 2013, 61(4):427-436.
Ward et al., 'Binding activities of a repertoire of single immunoglobulin variable domains secreted from *Escherichia coli*.' Nature. 1989, vol. 341, No. 6242, pp. 544-546.
Watanabe et al., 'Optimizing pH response of affinity between protein G and IgG Fc.' J. Biological Chemistry. 2009, 284(18):12373-12383.
Winter et al., 'Humanized Antibodies.' Immunology Today. 1993, 14(6):243-246.
Written Opinion of the International Searching Authority for International Application No. PCT/EP2012/051320, Jul. 30, 2013 (16 pages).
Wu et al., 'Receptor-mediated in vitro gene transformation by a soluble DNA carrier system.' Journal of Biological Chemistry. 1987, vol. 262, No. 10, pp. 4429-4432.
Lamon-Fava et al. (Apr. 7, 2011) "Lipoprotein(a) levels, apo(a) isoform size, and coronary heart disease risk in the Framingham Offspring Study," J. Lipid Res. 52:1181-1187.

(56) References Cited

OTHER PUBLICATIONS

Lunven et al. (2014) "A randomized study of the relative bioavailability, pharmacodynamics, and safety of alirocumab, a fully human monoclonal antibody to proprotein convertase subtilison/ kexin type 9, after single subcutaneous administration at three different injection sites in healthy subjects," J Am Coll Cardiol 63(12 Suppl 1): A1377.
Lunven et al. (Dec. 2014) "A randomized study of the relative pharmacokinetics, pharmacodynamics and safety of alirocumab, a fully human monoclonal antibody to PCSK9, after single subcutaneous administration at three different injection sites in healthy subjects," Cardiovasc Ther. 32(6):297-301.
McKenney et al. (Mar. 2012) "A randomized, double-blind, placebo-controlled trial of the safety and efficacy of a monoclonal antibody to proprotein convertase subtilisin/kexin type 9 serine protease, REGN727/SAR236553, in patients with primary hypercholesterolemia (NCT: 01288443);" Presented as a late-breaking oral presentation at the American College of Cardiology (ACC) Annual Scientific Session, Chicago, Illinois, USA.
Missouri DU Report (2003) "Statin Therapy" Drug Use Review Newsletter. 8(6) pp. 1-9.
Moriarty et al. (2014) "Odyssey Alternative: Efficacy and safety of the proprotein convertase subtilisin/kexin type 9 monoclonal antibody, alirocumab, versus ezetimibe, in patients with statin intolerance as defined by a placebo run-in and statin rechallenge arm," Circulation. 130:2108-2109.
Moriarty et al. (Aug. 1, 2013) "Homogeneity of treatment effect of REGN727/SAR236553, a fully human monoclonal antibody against PCSK9, in lowering LDL-C: data from three phase 2 studies," Eur Heart J. 34(Suppl 1):18. Abstract 142.
Moriarty et al. (Aug. 29, 2015) "Efficacy and safety of alirocumab versus ezetimibe in statin-intolerant patients, with a statin-rechallenge arm: The Odyssey Alternative randomized trial;" J Clin Lipidol. 9(6):758-769.
Moriarty et al. (Sep. 19, 2014) "Efficacy and safety of alirocumab, a monoclonal antibody to PCSK9, in statin-intolerant patients: Design and rationale of Odyssey Alternative, a randomized Phase 3 trial," J Clin Lipidol. 8 (6):554-561.
Pordy et al. (May 2013) "Alirocumab, a fully human monoclonal antibody to proprotein convertase subtilisin/kexin type 9: therapeutic dosing in phase 3 studies," J Clin Lipidol. 7(3):279.
Ramanathan et al. (2013) "Role of alirocumab (proprotein convertase subtilisin/kexin type 9 antibody) on CD81 levels and hepatitis C virus entry into hepatocytes," Circulation. 128:A12052.
Ray (Jan. 2015) "Alirocumab: an investigational treatment for hypercholesterolemia," Clin Lipidol. 10(1):9-12.
Ray et al. (2013) "Attainment of low-density lipoprotein cholesterol goals in patients at very high cardiovascular risk in the United Kingdom: results from a general practice population study," Value Health. 16(7):A513.
Rey et al. (2014) "Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects," J Am Coll Cardiol. 63(12 Suppl 1):A1375.
Reyes-Soffer et al. (2015) "Abstract 129: Effects of a proprotein convertase subtilisin/kexin type 9 inhibitor, alirocumab, on lipid and lipoprotein metabolism in normal subjects," Arterioscler, Thromb Vasc Biol. 35:A129.
Robinson et al. (2014) "Long-term safety, tolerability and efficacy of alirocumab versus placebo in high cardiovascular risk patients: first results from the Odyssey Long Term study in 2,341 patients," Circulation. 130:2120.
Robinson et al. (2015) "Adverse events in patients with low-density lipoprotein cholesterol levels <25 or <15 mg/dL on at least two consecutive visits in fourteen randomized, controlled, clinical trials of alirocumab," J Am Coll Cardiol. 65 (10_S):A1350.
Robinson et al. (Apr. 16, 2015) "Odyssey Long Term Investigators. Efficacy and Safety of Alirocumab in Reducing Lipids and Cardiovascular Events.," N Eng J Med. 372:1489-1499.
Robinson et al. (Aug. 31, 2014) "Long-term safety, tolerability and efficacy of alirocumab versus placebo in high cardiovascular risk patients: first results from the Odyssey Long Term study in 2,341 patients," Highlights Presented at ESC Congress, Barcelona Spain.
Robinson et al. (Sep. 30, 2014) "Efficacy and safety of alirocumab as add-on therapy in high-cardiovascular-risk patients with hypercholesterolemia not adequately controlled with atorvastatin (20 or 40 mg) or rosuvastatin (10 or 20mg): design and rationale of the Odyssey Options studies," Clin Cardiol. 37(10):597-604.
Roth et al. (Apr. 2014) "A 24-week study of alirocumab monotherapy versus ezetimibe: The first phase 3 data of a proprotein convertase subtilisin/kexin type 9 inhibitor," J Am Coll Cardiol. 63(12_S):A1370.
Roth et al. (Jan. 2015) "Odyssey Mono: effect of alirocumab 75 mg subcutaneously every 2 weeks as monotherapy versus ezetimibe over 24 weeks," Future Cardiol. 11(1):27-37.
Roth et al. (Jul. 2, 2014) "Monotherapy with the PCSK9 inhibitor alirocumab versus ezetimibe in patients with hypercholesterolemia: Results of a 24 week, double-blind, randomized Phase 3 trial," Int J Cardiol. 176(1):55-61.
Roth et al. (Mar. 2014) "Alirocumab for hyperlipidemia: physiology of PCSK9 inhibition, pharmacodynamics and Phase I and II clinical trial results of a PCSK9 monoclonal antibody," Future Cardiology. 10(2):183-199.
Roth et al. (Mar. 27, 2012) "The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469);" J Am Coll Cardiol. 59:E1620.
Roth et al. (May 2015) "Patient and physician perspectives on administration of the PCSK9 monoclonal antibody alirocumab, an injectable medication to lower LDL-C levels," J. Clin. Lipidol. 37(9):1945-1954.
Roth et al. (May 23-26, 2015) "Phase 3 Randomized Trial Evaluating Alirocumab Every Four Weeks Dosing as Add-on to Statin or as Monotherapy: Odyssey Choice I," International Symposium on Atherosclerosis, Abstract No. 254.
Roth et al. (Nov. 15, 2012) "Atorvastatin with or without an antibody to PCSK9 in primary hypercholesterolemia," N Engl J Med. 367(20):1891-1900.
Schwartz et al. (Aug. 7, 2014) "Effect of alirocumab, a monoclonal antibody to pcsk9, on long-term cardiovascular outcomes following acute coronary syndromes: Rationale and design of the odyssey outcomes trial" Am Heart J. 168 (5):682-689.
Shao (Apr. 26, 2014) "New Therapies for Lowering LDL-C: Targeting PCSK9," Abstract of oral presentation at the Sino-American Pharmaceutical Professionals Association—2014 Scientific Symposium, Apr. 26, 2014, New Jersey, USA.
Stahl (Jul. 15, 2010) "Early Clinical Development #1 REGN727: anti-PCSK9," Regeneron Pharmaceuticals. Accessible on the Internet at URL: http://files.shareholder.com/downloads/Regn/0x0x387214/534aaeb6-5e66-4e8f-86a9-0f9cac20d72f/REGN%20Investor%20Day%20Early%20Clinical%20Development1.pdf. 21 pages.
Steen et al. (2014) "Attainment of Lipid Levels in Patients at High Cardiovascular Risk: Results from a U.S. Managed Care Population Study," Circulation. 130:A19949.
Steen et al. (Mar. 2015) "Cardiovascular Event Rates in a High-Risk Managed Care Population in the United States," .J Am Coll Cardiol. 65(10_S):A1647.
Stein et al. (Mar. 25-28, 2012) "Safety and efficacy of a monoclonal antibody to PCSK9, REGN727/SAR236553, in statin-treated heterozygous familial hypercholesterolemia patients," Presented as an oral presentation at the 80th European Atherosclerosis Society (EAS) Congress, Milan, Italy. Abstract 1398.
Stein et al. (Mar. 30, 2014) "One year open-label treatment with alirocumab 150 mg every two weeks in heterozygous familial hypercholesterolemic patients," J Am Coll Cardiol. 63(12 Suppl 1):A1371.

(56) References Cited

OTHER PUBLICATIONS

Steinberg et al. (2009) "Inhibition of PCSK9: A powerful weapon for achieving ideal LDL cholesterol levels," Proceedings of the National Academy of Sciences USA. 106(24):9546-9547.
Stroes et al. (Jun. 17, 2014) "Anti-PCSK9 Antibody Effectively Lowers Cholesterol in Patients With Statin Intolerance," J. Am. Coll. Cardiol. 63(23):2541-2548.
Stroes et al. (Mar. 17, 2015) "Efficacy and safety of different dosing regimens of alirocumab (starting doses of 75 mg every two weeks and 150 mg every four weeks) versus placebo in patients with hypercholesterolemia not treated using statins: the Odyssey Choice II study," J Am Coll Cardiol. 65(10_S):A1370.
Sullivan et al. (Dec. 19, 2012) "Effect of a Monoclonal Antibody to PCSK9 on Low-Density Lipoprotein Cholesterol Levels in Statin-Intolerant Patients," JAMA. 308(23):2497-2506.
Swergold et al. (2010) "Safety, lipid, and lipoprotein effects of REGN727/SAR236553, a fully human proprotein convertase subtilisin kexin 9 (PCSK9) neutralizing monoclonal antibody administered intravenously to healthy volunteers," Circulation. 122:A23251.
Swergold et al. (2011) "Inhibition of proprotein convertase subtilisin/ kexin type 9 with a monoclonal antibody REGN727/SAR236553, effectively reduces low-density-lipoprotein cholesterol, as mono or add-on therapy in heterozygous familial and non-familial hypercholesterolaemia," Circulation 124:A16265.
Swergold et al. (2011) "REGN727/SAR236553, a fully human proprotein convertase subtilisin kexin 9 (PCSK9) monoclonal antibody: effects on safety and lipid and lipoprotein profiles when administered subcutaneously," J Am Coll Cardiol. 57(14):E2023.
Swergold et al. (2011) "REGN727/SAR236553, a fully-human monoclonal antibody to proprotein convertase subtilisin kexin 9 (PCSK9), decreases ApoB and non-HDL-C when administered intravenously to healthy volunteers," J Clin Lipidol. 5(3):219. Abstract 135.
Swergold et al. (Oct. 22-26, 2013) "Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB)," Abstract of a poster presentation at the American Society of Human Genetics (ASHG), Boston, USA.
Teramoto et al. (2014) "Efficacy and safety of alirocumab in Japanese patients with hypercholesterolemia on stable statin therapy: first data with the 75 mg every two weeks dose," Circulation. 130:A13651.
Toth et al. (2013) "Alirocumab, a proprotein convertase subtilisin/ kexin type 9 monoclonal antibody, reduces cholesterol concentrations of all serum low-density lipoprotein cholesterol fractions," Circulation. 128:A17313.
Toth et al. (2014) "Proprotein convertase subtilisin/kexin 9 monoclonal antibody therapy significantly reduces apoprotein CII and CIII levels in serum," Atherosclerosis. 235(2):e107-e108. Abstract EAS-0750.
Tsimikas et al. (Jul. 22, 2015) "Antisense therapy targeting apolipoprotein(a): A randomised double-blind, placebo-controlled phase 1 study," Lancet. 386:1472-1483.
Van Der Hoorn et al. (2014) "Alirocumab, a monoclonal antibody to PCSK-9, dose-dependently decreases atherosclerosis, improves plaque stability and shows additive effects with atorvastatin in APOE*3Leiden.CETP mice," Atherosclerosis. 235(2):e19. Abstract WS16.
Westerterp et al. (2006) "Cholesteryl Ester Transfer Protein Decreases High-Density Lipoprotein and Severely Aggravates Atherosclerosis in APOE*3-Leiden Mice," Arterioscler Thromb. Vasc. Biol. 26(11):2552-2559.
Anonymous (Jun. 27, 2013) "Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study," Archive from ClinicalTrials.gov for NCT01507831, 3 pages.

Anonymous (Mar. 11, 2014) "A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome," Archive from ClinicalTrials.gov for NCT01663402, 3 pages.
Anthem (Sep. 21, 2015) "Preprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016] 8 pages.
Bays et al. (2014) "PCSK9 Inhibitor Alirocumab as Add-on to Atorvastatin versus Other Lipid Treatment Strategies in Patients at High CVD Risk: Odyssey Options I," Circulation. 130:A16194.
Bays et al. (Dec. 2, 2014) "Efficacy and safety of combining alirocumab with atorvastatin or rosuvastatin versus statin intensification or adding ezetimibe in high cardiovascular risk patients: Odyssey Options I and II," Circulation. 130:2118-2119.
Bays et al. (May 2015) "Alirocumab treatment effect on non-HDL-C: pooled analyses of ten Phase 3 trials in the Odyssey program," J Clin Lipidol. 9(3):471-472. Abstract 183.
Blom et al. (May 8, 2014) "A 52-Week Placebo-Controlled Trial of Evolocumab in Hyperlipidemia," The New England Journal of Medicine. 370(19):1809-1819.
Cannon et al. (Feb. 16, 2015) "Efficacy and safety of alirocumab in high cardiovascular risk patients with inadequately controlled hypercholesterolaemia on maximally tolerated doses of statins: the Odyssey Combo II randomized controlled trial," Eur Heart J. 36(19):1186-1194.
Cariou et al. (May 23-26, 2015) "Patient and physician perspectives on administration of the PCSK9 monoclonal antibody alirocumab, an injectable medication to lower LDL-C levels," International Symposium on Atherosclerosis. Abstract No. 1039.
Catapano et al. (Feb. 8, 2013) "The safety of therapeutic monoclonal antibodies: implications for cardiovascular disease and targeting the PCSK9 pathway," Atherosclerosis. 228(1):18-28.
Colhoun et al. (Sep. 20, 2014) "Efficacy and safety of alirocumab, a fully human PCSK9 monoclonal antibody, in high cardiovascular risk patients with poorly controlled hypercholesterolemia on maximally tolerated doses of statins: rationale and design of the Odyssey Combo I and II trials," BMC Cardiovasc Disord. 14(1):121.
Costet (May 1, 2012) "PCSK9 inhibitors as LDL cholesterol-lowering agents: Rationale, concerns and preliminary outcomes," Drugs of the Future. 37(5):331-341.
Dube et al. (Apr. 2012) "Lipoprotein(a): more interesting than ever after 50 years," Curr. Opin. Lipidol. 23:133-140.
Duff et al. (2009) "Antibody-mediated disruption of the interaction between PCSK9 and the low-density lipoprotein receptor," Biochem. J. 419(3):577-584.
Dufour et al. (2012) "Effect of REGN727/SAR236553 PCSK9 fully human monoclonal antibody in patients with elevated triglycerides/ low high-density lipoprotein cholesterol: data from three phase 2 studies," Circulation. 126: A16127.
Dufour et al. (Sep. 30, 2014) "One year open-label treatment with alirocumab 150 mg every two weeks in heterozygous familial hypercholesterolemic patients," Can J Cardiol. 30(10 suppl):S338. Abstract 546.
Farnier et al. (2014) "Relationship between alirocumab, PCSK9 and LDL-C levels: results from the Odyssey Mono Phase 3 trial of alirocumab 75 mg every 2 weeks," Atherosclerosis. 235(2):e34-e35. Abstract EAS-0758.
Foody et al. (2013) "Attainment of low-density lipoprotein cholesterol goals in patients at high cardiovascular risk: results from a managed care population study," Circulation. 128:A17254.
Gaudet et al. (2012) "Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443)," Circulation. 126:A14725.
Gaudet et al. (Jun. 18, 2014) "Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials)," Am J Cardiol. 114(5):711-715.

(56) References Cited

OTHER PUBLICATIONS

Gaudet et al. (May 2013) "Alirocumab, a fully human monoclonal antibody to PCSK9, reduces high plasma Lp(a) concentration: pooled analysis of 352 patients from phase 2," J Clin Lipidol. 7(3):283-284. Abstract 178.

Ginsberg et al. (2014) "Odyssey High FH: efficacy and safety of alirocumab in patients with severe heterozygous familial hypercholesterolemia," Circulation. 130:2119.

Gorcyca et al. (May 2015) "Prevalence of atherosclerotic cardiovascular disease and diabetes in the United States," J Clin Lipidol. 9(3):424. Abstract 118.

Gusarova et al. (Dec. 18, 2012) "Reduction of LDL cholesterol by a monoclonal antibody to PCSK9 in rodents and nonhuman primates," Clin Lipidol. 7(6):737-743.

Gusarova et al. (Mar. 25-30, 2012) "Fully human antibody that blocks PCSK9 demonstrates reduction in LDL-C preclinically and in early clinical trials," Abstract of oral presentation at the Keystone Symposia on Molecular and Cellular Biology, Montana, USA.

Haddley et al. (Apr. 1, 2013) "Alirocumab Anti-Proprotein Convertase 9 (PCSK9) Mab Treatment of Hypercholesterolemia," Drugs of the Future. 38(4):213-219.

Hiriyama et al. (Jan. 1, 2014) "Effects of evolocumab (AMG 145), a monoclonal antibody to PCSK9, in hypercholesterolemic, statin-treated Japanese patients at high cardiovascular risk—primary results from the phase 2 YUKAWA study," Circulation Journal. 78(5):1073-1082.

Hopkins et al. (2013) "A randomized placebo-phase clinical trial with the monoclonal antibody alirocumab demonstrates reductions in low-density lipoprotein cholesterol in patients with proprotein convertase subtilisin/kexin type 9 gain-of-function mutations," Circulation. 128:A17156.

Hopkins et al. (Dec. 2015) "Characterization of Autosomal Dominant Hypercholesterolemia Caused by PCSK9 Gain of Function Mutations and its Specific Treatment with Alirocumab, a PCSK9 Monoclonal Antibody," Circ Cardiovasc Genet. 8(6):823-831.

Hovingh et al. (Feb. 13, 2013) "Diagnosis and treatment of familial hypercholesterolaemia," Eur Heart J. 34 (13):962-971.

Huang et al. (May 2015) "Clinical characteristics and unmet need among real-world atherosclerotic cardiovascular disease (ASCVD) patients stratified by statin use," J Clin Lipidol. 9(3):437-438. Abstract 134.

Jones et al. (2015) "Pooled safety and adverse events in nine randomized, placebo-controlled, phase 2 and 3 clinical trials of alirocumab," J Am Coll Cardiol. 65(10_S):A1363.

Junghans et al. (1990) "Anti-Tac-H, a Humanized Antibody to the Interleukin 2 Receptor with New Features for Immunotherapy in Malignant and Immune Disorders," Cancer Research. 50:1495-1502.

Kastelein et al. (Aug. 31, 2014) "Efficacy and Safety of Alirocumab in Patients with Heterozygous Familial Hypercholesterolemia not Adequately Controlled with Current Lipid-Lowering Therapy: Results of Odyssey FH I and FH II Studies," Poster Presented at the ECS Congress 2014. Barcelona, Spain.

Kastelein et al. (Jun. 2014) "Efficacy and Safety of Alirocumab in Patients with Heterozygous Familial Hypercholesterolemia not Adequately Controlled with Current Lipid-Lowering Therapy: Design and Rationale of the Odyssey FH Studies," Cardiovasc Drugs Ther. 28(3):281-289.

Kastelein et al. (Sep. 1, 2015) "Odyssey FH I and FH II: 78-week results with alirocumab treatment in 735 patients with heterozygous familial hypercholesterolemia," Eur Heart J. 36(43):2996-3003.

Kereiakes et al. (Dec. 2, 2014) "Efficacy and safety of alirocumab in high cardiovascular risk patients with suboptimally controlled hypercholesterolemia on maximally tolerated doses of statins: the Odyssey Combo I study," Circulation. 130:2119-2120.

Kereiakes et al. (Mar. 13, 2015) "Efficacy and safety of the PCSK9 inhibitor alirocumab among high cardiovascular risk patients on maximally tolerated statin therapy: the Odyssey Combo I study," Am Heart J. 169(6):906-915.

Konrad et al. (2011) "Effects of currently prescribed LDL-C-lowering drugs on PCSK9 and implications for the next generation of LDL-C-lowering agents," Lipids in Health and Disease. 10(1):38.

Koren et al. (2012) "Efficacy, safety and tolerability of 150 mg Q2W dose of the anti-PCSK9 mAb, REGN727/SAR236553: data from 3 phase 2 studies," Eur Heart J. 33(Abstract Supplement):37. Abstract 429.

Koren et al. (2014) "Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial," J Am Coll Cardiol. 63(12 Suppl 1):A1373.

Koren et al. (Jan. 22, 2015) "Safety and efficacy of alirocumab 150 mg every 2 weeks, a fully human proprotein convertase subtilisin/kexin type 9 monoclonal antibody: a Phase II pooled analysis," Postgrad Med. 22:1-8.

Koren et al. (May 2013) "Efficacy, safety and tolerability of alirocumab 150 mg Q2W, a fully human PCSK9 monoclonal antibody: a pooled analysis of 352 patients from phase 2," J Clin Lipidol. 7(3):279-280. Abstract 172.

Koschinsky et al. (Dec. 2014) "Lipoprotein(a): an important cardiovascular risk factor and a clinical conundrum," Endocrinol. Metab. Clin. North Am. 43:949-962.

Krauss et al. (2014) "Alirocumab, a fully human monoclonal antibody to proprotein convertase subtilisin/kexin type 9, and its effects on lipoprotein subfractions determined by ion mobility," Circulation. 130:A15525.

Kühnast et al. (2013) "PCSK-9 monoclonal antibody alirocumab dose-dependently decreases atherosclerosis development and enhances the effects of atorvastatin in APOE*3Leiden CETP mice," Circulation. 128:A15823.

Kühnast et al. (Oct. 2014) "Alirocumab inhibits atherosclerosis, improves the plaque morphology, and enhances the affects of a statin," J Lipid Res. 55(10):2103-2112.

Kuiper et al. (May 2015) "Statin use and low density lipoprotein cholesterol goal attainment among a high cardiovascular risk population in the Netherlands," Pharmo ISA Poster.

Lambert et al. (Jul. 17, 2012) "The PCSK9 decade," J Lipid Res. 53(12):2515-2524.

Lambert et al. (Nov. 24, 2014) "Normalization of Low-Density Lipoprotein Receptor Expression in Receptor Defective Homozygous Familial Hypercholesterolemia by Inhibition of PCSK9 With Alirocumab," J Am Coll Cardiol. 64(21):2299-2300.

Holliger et al., 'Diabodies: small bivalent and bispecific antibody fragments.' Proceedings of the National Academy of Sciences. 1993, vol. 90,No. 14, pp. 6444-6448.

Hopkins et al., 'Familial Hypercholesterolemias: Prevalence, genetics, diagnosis and screening recommendations from the National Lipid Association Expert Panel on Familial Hypercholesterolemia.' Journal of Clinical Lipidology. 2011, 5(3):S9-S17.

Horton et al., 'Molecular biology of PCSK9: its role in LDL metabolism.' Trends Biochem Sci., 2007, 32(2): 71-77.

Huston et al. 'Protein engineering of antibody binding sites: recovery of specific activity in an anti-digoxin single-chain Fv analogue produced in *Escherichia coli*.' Proceedings of the National Academy of Sciences. 1988, vol. 85, No. 16, pp. 5879.

Igawa et al., 'Antibody recycling by engineered pH-dependent antigen binding improves the duration of antigen neutralization.' Nature Biotechnology. 2010, 28(11):1203-1208.

International Search Report for International Application No. PCT/EP2012/051320, dated Sep. 21, 2012 (9 pages).

Ito et al., 'The His-probe method: effects of histidine residues introduced into the complementarity-determining regions of antibodies on antigen-antibody interactions at different pH values.' Federation of European Biochemical Societies. 1992, 309(1):85-88.

Jorgensen et al., 'Genetically elevated non-fasting triglycerides and calculated remnant cholesterol as casual risk factors for myocardial infarction.' European Heart Journal. 2013, 34:1826-1833.

Kawashiri et al., 'Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope.' Circulation. 2012, 126(21):13869.

(56) References Cited

OTHER PUBLICATIONS

Lagace et al., 'Secreted PCSK9 decreases the number of LDL receptors in hepatocytes and in liver of parabiotic mice.' J Clin Invest Am Soc Clin Invest., 2006, 116(11):2995-3005.
Langer et al., 'New methods of drug delivery.' Science. 1990, vol. 249, No. 4976, pp. 1527-1533.
Langer et al., 'Medical Applications of Controlled Release.' CRC Press, Boca Raton, Florida. 1984, pp. 115-138.
Leuenberger et al., 'A Multilingual Glossary of Biotechnological Terms.' Recueil des Travaux Chimiques des Pays Bas. 1996, vol. 115, No. 7, pp. 382.
Lippi et al., 'Lipoprotein(a): from ancestral benefit to modern pathogen?' QJ Med., 2000, 93:75-84.
Lopez, Dayami, 'Inhibition of PCSK9 as a Novel Strategy for the Treatment of Hypercholesterolemia.' Drug News & Perspectives Abstract. 2008, 21(6): 323.
Lose et al., 'Evaluation of Proprotein Convertase Subtilisin/Kexin Type 9: Focus on Potential Clinical and Therapeutic Implications for Low-Density Lipoprotein Cholesterol Lowering.' Journal of Human Pharmacology and Drug Therapy. 2013, 33(4):447-460.
Maeda et al., 'pH-dependent receptor/ligand dissociation as a determining factor for intracellular sorting of ligands for epidermal growth factor receptors in rat hepatocytes.' J. Controlled Release. 2002, 82:71-82.
Marcovina et al., 'Lipoprotein(a) as a Risk Factor for Coronary Artery Disease.' The American Journal of Cardiology. 1998, 82(12A):57U-66U.
Maxwell et al., 'Adenoviral-mediated expression of Pcsk9 in mice results in a low-density lipoprotein receptor knockout phenotype.' PNAS. 2004, 101(18):7100-7105.
McKenney et al., 'Safety and Efficacy of a Monoclonal Antibody to Proprotein Convertase Subtilisin/Kexin Type 9 Serine Protease, SAR236553/REGN727, in Patients With Primary Hypercholesterolemia Receiving Ongoing Stable Atorvastatin Therapy.' Journal of American College of Cardiology. 2012, 59(25):2335-2353.
Nakasako et al., 'The pH-dependent structural variation of complementarity-determining region H3 in the crystal structures of the Fv fragment from an anti-dansyl monoclonal antibody.' Journal of Molecular Biology. 1999, 291:117-134.
Naureckiene et al., 'Functional characterization of Narc 1, a novel proteinase related to proteinase K.' Archives of Biochemistry and Biophysics. 2003, 420:55-67.
Noguchi et al., 'The E32K variant of PCSK9 exacerbates the phenotype of familial hypercholesterolemia by increasing PCSK9 function and concentration in the circulation.' Atherosclerosis. 2010, 210(1):166-172.
Nordestgaard et al., 'Lipoprotein(s) as cardiovascular risk factor: current status.' European Heart Journal. 2010, 31:2844-2853.
Padlan et al., 'Identification of specificity-determining residues in antibodies.' The FASEB Journal. 1995, vol. 9, No. 1, pp. 133-139.
Parhofer, 'Lipoprotein(a): Medical Treatment Options for an Elusive Molecule.' Current Pharmaceutical Design. 2011, 17:871-876.
Kostner et al. (Jun. 4, 2013) "When should we measure lipoprotein (a)?" European Heart Journal. 34:3268-3276.
Lefranc et al. (2009) "IMGT®, the international ImMunoGeneTics information system®" Nucl. Acids Res. 37:D1006-D1012.
Li et al. (2009) "Recent Patents on PCSK9: A New Target for Treating Hypercholesterolemia," Recent Patents on DNA and Gene Sequences. 3(3):201-212.
Majumdar et al. (2011) "Evaluation of the effect of syringe surfaces on protein formulations," Journal of Pharmaceutical Sciences. 100(7):2563-2573.
McKenney et al. (Jun. 2-5, 2013) "Dynamics between the monoclonal antibody SAR236553/REGN727, proprotein convertase subtilisin/ kexin type 9 (PCSK9) and low-density lipoprotein cholesterol (LDL-C) levels (funding: Regeneron/Sanofi)," Abstract of an oral presentation at the 81st European Atherosclerosis Society (EAS) Congress, Jun. 2-5, 2013, Lyon, France.
McKenney et al. (Jun. 2-5, 2013) "Dynamics between the monoclonal antibody SAR236553/REGN727, proprotein convertase subtilisin/ kexin type 9 (PCSK9) and low-density lipoprotein cholesterol (LDL-C) levels (funding: Regeneron/Sanofi)," Presented as a poster presentation at the 81st European Atherosclerosis Society (EAS) Congress, Jun. 2-5, 2013, Lyon, France.
Rader et al. (1995) "The Low Density Lipoprotein Receptor Is Not Required for Normal Catabolism of Lp(a) in Humans," The Journal of Clinical Investigation. 95:1403-1408.
Regeneron Pharmaceuticals (Nov. 5, 2012) "Sanofi and Regeneron Announce Patient Enrollment in Cardiovascular Outcome Trial with Antibody to PCSK9 for Hypercholesterolemia," Press Release. Acquire Media.
Robinson (2002) "Protein Deamidation," Proc. Natl. Acad. Sci. USA 99(8):5283-5288.
Romagnuolo et al. (Mar. 16, 2015) "Lipoprotein(a) Catabolism is Regulated by Proprotein Convertase Subtilisin/Kexin Type 9 through the Low Density Lipoprotein Receptor," The Journal of Biological Chemistry. 290 (18):11649-11662.
Scaviner et al. (1999) "Protein Displays of the Human Immunoglobulin Heavy, Kappa and Lambda Variable and Joining Regions," Exp. Clin. Immunogenet. 16:234-240.
Schäfer et al. (Mar. 14-16, 2011) "Cholesterol lowering effect of SAR236553/REGN727, a fully human PCSK9 blocking monoclonal antibody in male Syrian hamster," Presented as a poster at the Drugs Affecting Lipid Metabolism (DALM)—XVII International Symposium, Mar. 14-16, 2011, Doha, Qatar.
Varrett et al. (1999) "A third major locus for autosomal dominant hypercholesterolemia Maps to 1p34.1-p32," Am. J. Hum. Genet. 64:1378-1387.
Wang (1999) "Instability, stabilization, and formulation of liquid protein pharmaceuticals," International J. Pharmaceutics 185(2):129-188.
Wang (2009) "Fixed dosing versus body size-based dosing of monoclonal antibodies in adult clinical trials," J Clin Pharmacol. 49(9):1012-1024.
Webb et al. (2002) "A new mechanism for decreasing aggregation of Recombinant Human Interferon-gamma by a Surfactant: Slowed Dissolution of Lyophilized Formulations in a Solution Containing 0.03% Polysorbate 20," J. Pharm. Sci. 91(2):543-558.
Abifadel et al., 'Identification and characterization of new gain-of-function mutations in the PCSK9 gene responsible for autosomal dominant hypercholesterolemia.' Atherosclerosis. 2012, 223(2):394-400.
Abifadel et al., 'Mutations and polymorphisms in the proprotein convertase subtilisin kexin 9 (PCSK9) gene in cholesterol metabolism and disease.' Human Mutation. 2009, 30(4):520-529.
Abifadel et al., 'Mutations in PCSK9 cause autosomal dominant hypercholesterolemia.' Nature Genetics. 2003, 34 (2):154-156.
Alborn et al., 'Serum proprotein convertase subtilisin Kexin type 9 is correlated directly with serum LDL cholesterol.' Clinical Chemistry. 2007, 53(10):1814-1819.
Almagro et al., 'Humanization of antibodies.' Frontiers in Bioscience. 2008, vol. 13, pp. 1619-1633.
Al-Mashhadi et al., 'Atherosclerosis: Familial hypercholesterolemia and atherosclerosis in clones minipigs created by DNA transposition of a human PCSK9 gain-of-function mutant.' Science Translation Medicine, American Association for the Advancement of Science. 2013, 5(166):44-53.
Altschul et al., 'Basic local alignment search tool.' Journal of Molecular Biology. 1990, vol. 215, No. 3, pp. 403-410.
Altschul et al., 'Gapped BLAST and PSI-BLAST: a new generation of protein database search programs.' Nucleic Acids Research. 1997, vol. 25, No. 17, pp. 3389-3402.
Amgen: 'Ascending Multiple Dose Study to Evaluate the Safety, Tolerability, Pharmacokinetics and Pharmacodynamics of AMG 145 in Subjects With Hyperlipidemia on Stable Doses of a Statin'. May 27, 2010, XP002682099. Retrieved from the Internet: URL:http://clinicaltrials.gov/ct2/show/nct01133522?term=amg+145&rank=2 Accessed on Aug. 6, 2014.
Angal et al., 'A single amino acid substitution abolishes the heterogeneity of chimeric mouse/human (IgG4) antibody.' Molecular Immunology. 1993, vol. 30, No. 1, pp. 105-108.
Attie et al., 'Dual regulation of the LDL receptor—Some clarity and new questions.' Cell Metabolism. 2005, 5:290-292.

(56) References Cited

OTHER PUBLICATIONS

Annex to Form PCT/ISA/206—Communication Relating to the Results of the Partial International Search for PCT/US2009/068013, dated Mar. 10, 2010.
Benjannet et al., 'The Proprotein Convertase (PC) PCSK9 Is Inactivated by Furin and/or PC5/6A.' J. Biological Chemistry. 2006, 281(41): 30561-30572.
Bird et al. 'Single-chain antigen-binding proteins.' Science. 1988, vol. 242, No. 4877, pp. 423-426.
Chan et al., 'A Proprotein Convertase subtilisin/kexin type 9 Neutralizing Antibody Reduces Serum Cholesterol in Mice and Non-human primates.' PNAS. 2009, vol. 106, No. 24, pp. 9820-9825.
Chaparro-Riggers et al., 'Increasing serum half-life and extending cholesterol lowering in vivo by engineering antibody with pH-sensitive binding to PCSK9.' J. Biological Chemistry. 2012, 287(14):11090-11097.
Fallon et al., 'Increased endosomal sorting of ligand to recycling enhances potency of an intereukin-2 analog.' J. Biological Chemistry. 2000, 275(10):6790-6797.
Farnier, Michel, 'The role of proprotein convertase subtilisin/kexin type 9 in hyperlipidemia: Focus on therapeutic implications.' American Journal of Cardiovascular Drugs. 2011, 11(3):145-152.
Fasano et al., 'Activity of Gain-of-Function PCSK9 Mutants on LDLR Correlates with Total-Cholesterol Values in ADH patients.' NMCD Nutrition Metabolism and Cardiovascular Diseases. 2008, 18(1):S46.
Foote et al., 'Antibody Framework Residues Affecting the Conformation of the Hypervariable Loops.' J. Mol. Biol. 1992, 224:487-499.
Gonnet et al. 'Exhaustive matching of the entire protein sequence database.' Science. 1992, vol. 256, No. 5062, pp. 1443-1445.
Grozdanov et al., 'Expression and localization of PCSK9 in rat hepatic cells.' Biochem. Cell. Biol., 2006, 84:80-92.
Heap et al., 'Analysis of a 17-amino acid residue, virus-neutralizing microantibody.' Journal of General Virology. 2005, vol. 86, No. 6, pp. 1791-1800.
Hochleitner et al. 'Characterization of a discontinuous epitope of the human immunodeficiency virus (HIV) core protein p24 by epitope excision and differential chemical modification followed by mass spectrometric peptide mapping analysis.' Protein Science. 2000, vol. 9, No. 3, pp. 487-496.
Barbie et al. (1998) "The Human Immunoglobulin Kappa Variable (IGKV) Genes and Joining (IGKJ) Segments," Exp. Clin. Immunogenet. 15:171-183.
Breen et al. (2001) "Effect of moisture on the stability of a lyophilized humanized monoclonal antibody formulation," Pharmaceutical Research. 18(9):1345-1353.
Cannon et al. (Aug. 31, 2014) "Efficacy and safety of alirocumab in high cardiovascular risk patients with inadequately controlled hypercholesterolaemia on maximally tolerated daily statin: results from the Odyssey Combo II study," presentation presented at the ESC Congress 2014.
Carpenter (1997) "Rational Design of Stable Lyophilized Protein Formulations: Some Practical Advice," Pharm. Res. 14(8):969-975.
clinicaltrials.gov (Aug. 10, 2012) "View of NCT01663402," US National Institutes of Health. [accessible on the internet at: https://clinicaltrials.gov/archive/NCT01663402/2012_08_10].
clinicaltrials.gov (Aug. 12, 2013) "View of NCT01617655," US National Institutes of Health. [accessible on the internet at: https://clinicaltrials.gov/archive/NCT01617655/2013_08_12].
clinicaltrials.gov (Aug. 20, 2014) "View of NCT01604824," US National Institutes of Health. [accessible on the internet at: https://clinicaltrials.gov/archive/NCT01604824/2014_08_20].
clinicaltrials.gov (Aug. 7, 2014) "View of NCT01507831," US National Institutes of Health. [accessible on the internet at: https://clinicaltrials.gov/archive/NCT01507831/2014_08_07].
clinicaltrials.gov (Dec. 23, 2010) "View of NCT01266876," US National Institutes of Health. [accessible on the internet at: https://clinicaltrials.gov/archive/NCT01266876/2010_12_23].
clinicaltrials.gov (Dec. 27, 2013) "View of NCT02023879," US National Institutes of Health. [accessible on the internet at: https://clinicaltrials.gov/archive/NCT02023879/2013_12_27].
clinicaltrials.gov (Feb. 1, 2011) "View of NCT01288443," US National Institutes of Health. [accessible on the internet at: https://clinicaltrials.gov/archive/NCT01288443/2011_02_01].
clinicaltrials.gov (Feb. 1, 2011) "View of NCT01288469," US National Institutes of Health. [accessible on the internet at: https://clinicaltrials.gov/archive/NCT01288469/2011_02_01].
clinicaltrials.gov (Jan. 10, 2012) "View of NCT01507831," US National Institutes of Health. [accessible on the internet at: https://clinicaltrials.gov/archive/NCT01507831/2012_01_10].
clinicaltrials.gov (Jan. 24, 2013) "View of NCT01604824," US National Institutes of Health. [accessible on the internet at: https://clinicaltrials.gov/archive/NCT01604824/2013_01_24].
clinicaltrials.gov (Jan. 30, 2014) "View of NCT01812707," US National Institutes of Health. [accessible on the internet at: https://clinicaltrials.gov/archive/NCT01812707/2014_01_30].
clinicaltrials.gov (Jul. 12, 2010) "View of NCT01161082," US National Institutes of Health. [accessible on the internet at: https://clinicaltrials.gov/archive/NCT01161082/2010_07_12].
clinicaltrials.gov (Jul. 17, 2012) "View of NCT01644175," US National Institutes of Health. [accessible on the internet at: https://clinicaltrials.gov/archive/NCT01644175/2012_07_17].
clinicaltrials.gov (Jul. 17, 2012) "View of NCT01644188," US National Institutes of Health. [accessible on the internet at: https://clinicaltrials.gov/archive/NCT01644188/2012_07_17].
clinicaltrials.gov (Jul. 18, 2012) "View of NCT01644474," US National Institutes of Health. [accessible on the internet at: https://clinicaltrials.gov/archive/NCT01644474/2012_07_18].
clinicaltrials.gov (Jul. 18, 2013) "View of NCT01644175," US National Institutes of Health. [accessible on the internet at: https://clinicaltrials.gov/archive/NCT01644175/2013_07_18].
clinicaltrials.gov (Jul. 18, 2013) "View of NCT01644474," US National Institutes of Health. [accessible on the internet at: https://clinicaltrials.gov/archive/NCT01644474/2013_07_18].
clinicaltrials.gov (Jul. 2, 2013) "View of NCT01288443," US National Institutes of Health. [accessible on the internet at: https://clinicaltrials.gov/archive/NCT01288443/2013_07_02].
clinicaltrials.gov (Jul. 2, 2013) "View of NCT01288469," US National Institutes of Health. [accessible on the internet at: https://clinicaltrials.gov/archive/NCT01288469/2013_07_02].
clinicaltrials.gov (Jul. 22, 2014) "View of NCT02023879," US National Institutes of Health. [accessible on the internet at: https://clinicaltrials.gov/archive/NCT02023879/2014_07_22].
clinicaltrials.gov (Jul. 8, 2014) "View of NCT01644474," US National Institutes of Health. [accessible on the internet at: https://clinicaltrials.gov/archive/NCT01644474/2014_07_08].
clinicaltrials.gov (Jun. 11, 2012) "View of NCT01617655," US National Institutes of Health. [accessible on the internet at: https://clinicaltrials.gov/archive/NCT01617655/2012_06_11].
clinicaltrials.gov (Jun. 18, 2012) "View of NCT01623115," US National Institutes of Health. [accessible on the internet at: https://clinicaltrials.gov/archive/NCT01623115/2012_06_18].
clinicaltrials.gov (Jun. 27, 2013) "View of NCT01507831," US National Institutes of Health. [accessible on the internet at: https://clinicaltrials.gov/archive/NCT01507831/2013_06_27].
clinicaltrials.gov (Jun. 27, 2013) "View of NCT01623115," US National Institutes of Health. [accessible on the internet at: https://clinicaltrials.gov/archive/NCT01623115/2013_06_27].
clinicaltrials.gov (Jun. 27, 2013) "View of NCT01812707," US National Institutes of Health. [accessible on the internet at: https://clinicaltrials.gov/archive/NCT01812707/2013_06_27].
clinicaltrials.gov (Mar. 15, 2013) "View of NCT01812707," US National Institutes of Health. [accessible on the internet at: https://clinicaltrials.gov/archive/NCT01812707/2013_03_15].
clinicaltrials.gov (Mar. 16, 2012) "View of NCT01266876," US National Institutes of Health. [accessible on the internet at: https://clinicaltrials.gov/archive/NCT01266876/2012_03_16].
clinicaltrials.gov (May 23, 2012) "View of NCT01604824," US National Institutes of Health. [accessible on the internet at: https://clinicaltrials.gov/archive/NCT01604824/2012_05_23].

(56) References Cited

OTHER PUBLICATIONS clinicaltrials.gov (Nov. 7, 2011) "View of NCT01161082," US National Institutes of Health. [accessible on the internet at: https://clinicaltrials.gov/archive/NCT01161082/2011_11_07].
clinicaltrials.gov (Oct. 1, 2014) "View of NCT01644175," US National Institutes of Health. [accessible on the internet at: https://clinicaltrials.gov/archive/NCT01644175/2014_10_01].
clinicaltrials.gov (Oct. 17, 2012) "View of NCT01709500," US National Institutes of Health. [accessible on the internet at: https://clinicaltrials.gov/archive/NCT01709500/2012_10_17].
clinicaltrials.gov (Oct. 17, 2012) "View of NCT01709513," US National Institutes of Health. [accessible on the internet at: https://clinicaltrials.gov/archive/NCT01709513/2012_10_17].
clinicaltrials.gov (Oct. 22, 2013) "View of NCT01663402," US National Institutes of Health. [accessible on the internet at: https://clinicaltrials.gov/archive/NCT01663402/2013_10_22].
clinicaltrials.gov (Oct. 25, 2013) "View of NCT01709500," US National Institutes of Health. [accessible on the internet at: https://clinicaltrials.gov/archive/NCT01709500/2013_10_25].
clinicaltrials.gov (Oct. 27, 2014) "View of NCT01644188," US National Institutes of Health. [accessible on the internet at: https://clinicaltrials.gov/archive/NCT01644188/2014_10_27].
clinicaltrials.gov (Oct. 6, 2014) "View of NCT01617655," US National Institutes of Health. [accessible on the internet at: https://clinicaltrials.gov/archive/NCT01617655/2014_10_06].
clinicaltrials.gov (Oct. 6, 2014) "View of NCT01623115," US National Institutes of Health. [accessible on the internet at: https://clinicaltrials.gov/archive/NCT01623115/2014_10_06].
clinicaltrials.gov (Oct. 6, 2014) "View of NCT01663402," US National Institutes of Health. [accessible on the internet at: https://clinicaltrials.gov/archive/NCT01663402/2014_10_06].
clinicaltrials.gov (Oct. 7, 2013) "View of NCT01644188," US National Institutes of Health. [accessible on the internet at: https://clinicaltrials.gov/archive/NCT01644188/2013_10_07].
clinicaltrials.gov (Oct. 7, 2013) "View of NCT01709513," US National Institutes of Health. [accessible on the internet at: https://clinicaltrials.gov/archive/NCT01709513/2013_10_07].
Daugherty et al. (2006) "Formulation and delivery issues for monoclonal antibody therapeutics," Advanced Drug Delivery Reviews 58:686-706.
Davidson et al. (2011) "Clinical utility of inflammatory markers and advanced lipoprotein testing: Advice from an expert panel of lipid specialists," Journal of Clinical Lipidology. 5:338-367.
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Abstract of a presentation presented at the 81st European Atherosclerosis Society (EAS) Congress, Jun. 2-5, 2013, Lyon, France.
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Presentation presented at the 81st European Atherosclerosis Society (EAS) Congress, Jun. 2-5, 2013, Lyon, France.
Katayama et al. (2004) "Retrospective statistical analysis of lyophilized Protein Formulations of Progenipoietin Using PLS: Determination of the Critical Parameters for Long-Term Storage Stability," J. Pharm. Sci. 93(10):2609-2623.
Miettinen et al. (1971) "Cholesterol production in obesity," Circulation. 44(5):842-850.
Wong et al. (May 1-4, 2014) "Residual Dyslipidemia According to LDL-C, non-HDL-C and Apolipoprotein B by Cardiovascular Risk Category in Statin Treated US Adults,"J Clin Lipidol. 8:323-324. Presented as a poster presentation at the National Lipid Association Scientific Sessions, Orlando, Florida, USA.
International Preliminary Report on Patentability corresponding to International Patent Application No. PCT/EP2012/051320, dated Jul. 30, 2013, 17 pages.
International Preliminary Report on Patentability corresponding to International Patent Application No. PCT/EP2012/051321, dated Jul. 30, 2013, 7 pages.
International Search Report with Written Opinion corresponding to International Patent Application No. PCT/PP2012/051321, dated Apr. 19, 2012, 10 pages.
International Search Report with Written Opinion corresponding to International Patent Application No. PCT/EP2012/057890, dated Aug. 28, 2012, 14 pages.
International Search Report with Written Opinion corresponding to International Patent Application No. PCT/EP2015/055369, dated May 21, 2015, 11 pages.
International Search Report with Written Opinion corresponding to International Patent Application No. PCT/US2014/041204, dated Oct. 17, 2014, 14 pages.
International Search Report with Written Opinion corresponding to International Patent Application No. PCT/US2014/060109, dated Apr. 16, 2015, 19 pages.
International Search Report with Written Opinion corresponding to International Patent Application No. PCT/US2014/065149, dated Feb. 3, 2015, 17 pages.
International Search Report with Written Opinion corresponding to International Patent Application No. PCT/US2015/015633, dated Aug. 19, 2015, 23 pages.
International Search Report with Written Opinion corresponding to International Patent Application No. PCT/US2015/020564, dated Jun. 12, 2015, 20 pages.
International Search Report with Written Opinion corresponding to International Patent Application No. PCT/US2015/040754, dated Oct. 14, 2015, 15 pages.
International Search Report with Written Opinion corresponding to International Patent Application No. PCT/US2015/040765, dated Nov. 26, 2015, 15 pages.
Office Action corresponding to Chinese Patent Application No. 201280015477.6, dated Dec. 2, 2014—with English summary, 14 pages.
Office Action corresponding to Chinese Patent Application No. 201280015571.1, dated Sep. 3, 2014—with English summary, 12 pages.
Office Action corresponding to European Patent Application No. 12701015.5, dated Apr. 24, 2015, 9 pages.
Office Action corresponding to European Patent Application No. 12701015.5, dated May 30, 2014, 8 pages.
Office Action corresponding to European Patent Application No. 12701742.4, dated Jun. 1, 2015, 10 pages.
Office Action corresponding to European Patent Application No. 12701742.4, dated May 28, 2014, 8 pages.
Third Party Observations corresponding to European Patent Application No. 12761864.3, dated Feb. 24, 2016, 9 pages.
Todo et al. (2004) "Detailed analysis of serum lipids and lipoproteins from Japanese type III hyperlipoproteinemia with apolipoprotein E2/2 phenotype," Clin. Chim. Acta 348:35-40.
Brouwers et al. (2013) "Plasma proprotein convertase subtilisin kexin type 9 levels are related to markers of cholesterol synthesis in familial combined hyperlipidemia," Nutrition, Metabolism & Cardiovascular Diseases, 23, 7 pp.
Lambert et al. (2009) "Review: Molecular basis of PCSK9 function," Atherosclerosis, 203, 7 pp.
Ned et al. (2011) "Cascade Screening for Familial Hypercholesterolemia (FH)," PLOS Currents Evidence on Genomic Tests, Edition 1, 13 pp.
Rahilly-Tierney et al. (2009) "Low-Density Lipoprotein Reduction and Magnitude of Cardiovascular Risk Reduction," Prev. Cardiol. 12(2):80-87.
Sanofi and Regeneron Report Positive Top-line Results with Alirocumab from First Phase 3 Study of a PCSK9 Inhibitor for LDL Cholesterol Reduction, Oct. 16, 2013, Retrieved from the Internet, [Last accessed Dec. 4, 2018: http://www.epresspack.net/mmr/sanofi-pcsk9-1st-phase3-results/].
Sanofi and Regeneron Announce Collaboration with American College of Cardiology for PCSK9 Inhibitor Clinical Program, Dec. 19, 2013, Retrieved from the Internet, [Last accessed Dec. 4, 2018:

(56) References Cited

OTHER PUBLICATIONS https://newsroom.regeneron.com/news-release/news-release-details/sanofi-and regeneron-announce-collaboration-american-college].
Australian Public Assessment Report for Alirocumab (rch) (2016) Australian Government Department of Health, Therapeutic Goods Administration. Sponsor: Sano-Aventis Australia Pty Ltd. 93 pp.
Ni et al. (2010) "A proprotein convertase subtilisin-like/kexin type 9 (PCSK9) C-terminal domain antibody antigen-binding fragment inhibits PCSK9 internalization and restores low density lipoprotein uptake," J Biol Chem. 285 (17):12882-91.

BAS = Baseline (Day -29)
Assessments from Day -29 (excluded) to Day -1 (included) are on Ezetimibe, Fenofibrate or Placebo alone BAS = Baseline (Day -1)
Assessments from Day -29 (excluded) to Day -1 (included) are on Ezetimibe, Fenofibrate or Placebo alone BAS = Baseline (Day -29)
Assessments from Day -29 (excluded) to Day -1 (included) are on Ezetimibe, Fenofibrate or Placebo alone

SEQUENCE LISTING

<160> NUMBER OF SEQ ID NOS: 198

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

```
Ala Met Asn Trp Val Arg Gln Ala Pro Gly Lys Gly Leu Asp Trp Val
            35                  40                  45

Ser Thr Ile Ser Gly Ser Gly Gly Thr Thr Asn Tyr Ala Asp Ser Val
     50                  55                  60

Lys Gly Arg Phe Ile Ile Ser Arg Asp Ser Ser Lys His Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Asn Asn Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Gly Ser Gly Gly Thr Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Asp Ser Asn Trp Gly Asn Phe Asp Leu
1               5                   10

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic
      REGN727 heavy chain polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
            35                  40                  45
```

Ser Thr Ile Ser Gly Ser Gly Gly Thr Thr Asn Tyr Ala Asp Ser Val
 50                  55                  60

Lys Gly Arg Phe Ile Ile Ser Arg Asp Ser Ser Lys His Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 6
<211> LENGTH: 113

```
-continued

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Val Leu Tyr Arg Ser Asn Asn Arg Asn Phe
1               5                   10

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ala Ser
1

<210> SEQ ID NO 9
<211> LENGTH: 220
<212> TYPE: PRT
<213> ORGANISM: Artificial Sequence
<220> FEATURE:
<223> OTHER INFORMATION: Description of Artificial Sequence: Synthetic
      REGN727 light chain polypeptide

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45
```

```
Pro Pro Asn Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Gln
                 85                  90                  95
Tyr Tyr Thr Thr Pro Tyr Thr Phe Gly Gln Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
210                 215                 220

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Tyr Tyr Thr Thr Pro Tyr Thr
 1               5

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Met Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser His
            20                  25                  30
Trp Met Lys Trp Val Arg Gln Ala Pro Gly Lys Gly Leu Glu Trp Val
        35                  40                  45
Ala Asn Ile Asn Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Phe
 65                  70                  75                  80
Leu Gln Met Asn Ser Leu Arg Ala Glu Asp Thr Ala Val Tyr Tyr Cys
                 85                  90                  95
Ala Arg Asp Ile Val Leu Met Val Tyr Asp Met Asp Tyr Tyr Tyr Tyr
            100                 105                 110
```

Gly Met Asp Val Trp Gly Gln Gly Thr Thr Val Thr Val Ser Ser
        115                 120                 125

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Thr Phe Ser Ser His Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn Gln Asp Gly Ser Glu Lys
1               5

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Asp Ile Val Leu Met Val Tyr Asp Met Asp Tyr Tyr Tyr Tyr
1               5                   10                  15

Gly Met Asp Val
            20

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Leu Leu His Ser Asn Gly Asn Asn Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gly Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gln Thr Leu Gln Thr Pro Leu Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Ser His Trp
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Asn Gln Asp Gly Ser Glu Lys
1               5

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 21

Ala Arg Asp Ile Val Leu Met Val Tyr Asp Met Asp Tyr Tyr Tyr
1               5                   10                  15

Gly Met Asp Val
            20

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Leu His His Ser Asn Gly Asn Asn Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Gly Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gln Thr Leu Gln Thr Pro Leu Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Phe Thr Phe Ser Ser His Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Asn Gln Asp Gly Ser Glu Lys
1               5
```

```
<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Asp Ile Val Leu Met Val Tyr His Met Asp Tyr Tyr Tyr Tyr
1               5                   10                  15

Gly Met Asp Val
            20

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Leu Leu His Ser Asn Gly Asn Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Gly Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Gln Thr Leu Gln Thr Pro Leu Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Thr Phe Ser Ser His Trp
1               5

<210> SEQ ID NO 32
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 32

Ile Asn Gln Asp Gly Ser Glu Lys
1               5

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asp Ile Val Leu Met Val Tyr His Met Asp Tyr Tyr Tyr Tyr
1               5                  10                  15

Gly Met Asp Val
            20

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Leu His His Ser Asn Gly Asn Asn Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Gly Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Gln Thr Leu Gln Thr Pro Leu Thr
1               5

<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: Synthetic
      VH; m2CX1D05 polypeptide

<400> SEQUENCE: 37

Gln Val Gln Leu Val Gln Ser Gly Ala Glu Val Lys Lys Pro Gly Ser
```

```
                1               5                   10                  15
            Ser Val Lys Val Ser Cys Lys Ala Ser Gly Gly Thr Phe Asn Ser His
                            20                  25                  30

Ala Ile Ser Trp Val Arg Gln Ala Pro Gly Gln Gly Leu Glu Trp Met
                        35                  40                  45

Gly Gly Ile Asn Pro Ile Leu Gly Ile Ala Asn Tyr Ala Gln Lys Phe
                    50                  55                  60

Gln Gly Arg Val Thr Ile Thr Ala Asp Glu Ser Thr Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg His Tyr Glu Ile Gln Ile Gly Arg Tyr Gly Met Asn Val Tyr
                            100                 105                 110

Tyr Leu Met Tyr Arg Phe Ala Ser Trp Gly Gln Gly Thr Leu Val Thr
                        115                 120                 125

Val Ser Ser
                130

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; m2CX1D05 peptide

<400> SEQUENCE: 38

Gly Gly Thr Phe Asn Ser His Ala Ile Ser
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; m2CX1D05 peptide

<400> SEQUENCE: 39

Trp Met Gly Gly Ile Asn Pro Ile Leu Gly Ile Ala Asn Tyr Ala Gln
1               5                   10                  15

Lys Phe Gln Gly
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      VH CDR3; m2CX1D05 peptide

<400> SEQUENCE: 40

His Tyr Glu Ile Gln Ile Gly Arg Tyr Gly Met Asn Val Tyr Tyr Leu
1               5                   10                  15

Met Tyr Arg Phe Ala Ser
            20

<210> SEQ ID NO 41
<211> LENGTH: 213
<212> TYPE: PRT
<213> ORGANISM: Artificial Sequence
```

```
<220> FEATURE:
<223> OTHER INFORMATION: Description of Artificial Sequence: Synthetic
      LC; m2CX1D05 polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Ala
    210

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR 1; m2CX1D05 peptide

<400> SEQUENCE: 42

Arg Ala Ser Gln Gly Ile Arg Ser Ala Leu Asn
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; m2CX1D05 peptide

<400> SEQUENCE: 43

Leu Leu Ile Tyr Asn Gly Ser Thr Leu Gln Ser
1               5                   10

<210> SEQ ID NO 44
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      VL CDR3; m2CX1D05 peptide

<400> SEQUENCE: 44

Gln Gln Phe Asp Gly Asp Pro
1               5

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      VH; 1B20 polypeptide

<400> SEQUENCE: 45

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Ser Trp Val Arg Gln Met Pro Gly Lys Gly Leu Glu Trp Met
            35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
                100                 105                 110

Thr Leu Val Thr Val Ser Ser
        115

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; 1B20 peptide

<400> SEQUENCE: 46

Gly Tyr Ser Phe Thr Asn Tyr Trp Ile Ser
1               5                   10

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; 1B20 peptide

<400> SEQUENCE: 47

Trp Met Gly Ile Ile Tyr Pro Gly Asp Ser Tyr Thr Asn Tyr Ser Pro
1               5                   10                  15

Ser Phe Gln Gly
            20

<210> SEQ ID NO 48
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR3; 1B20 peptide

<400> SEQUENCE: 48

Asp Tyr Trp Tyr Lys Pro Leu Phe Asp Ile
1               5                   10

<210> SEQ ID NO 49
<211> LENGTH: 220
<212> TYPE: PRT
<213> ORGANISM: Artificial Sequence
<220> FEATURE:
<223> OTHER INFORMATION: Description of Artificial Sequence: Synthetic
      LC; 1B20 polypeptide

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Ala
    210                 215                 220

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1; 1B20 peptide

<400> SEQUENCE: 50

Arg Ser Ser Gln Ser Val Leu Tyr Ser Ser Asn Asn Lys Asn Tyr Leu
1               5                   10                  15
```

Ala

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; 1B20 peptide

<400> SEQUENCE: 51

Leu Leu Ile Tyr Trp Ala Ser Thr Arg Glu Ser
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      VL CDR3; 1B20 peptide

<400> SEQUENCE: 52

Gln Gln Tyr Ser Ser Phe Pro Ile
1               5

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 heavy chain CDR1 antibody region peptide

<400> SEQUENCE: 54

Lys Ala Ser Gly Tyr Thr Phe Ser Ser Tyr Gly Met Tyr Trp Val Arg
1               5                   10                  15

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      AX132 heavy chain CDR2 antibody region peptide

<400> SEQUENCE: 55

Trp Ile Gly Trp Ile Asp Pro Gly Ser Gly Gly Thr Lys Tyr Asn Glu
1               5                   10                  15

Lys Phe Lys Gly Lys Ala Thr
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      AX132 heavy chain CDR3 antibody region peptide

<400> SEQUENCE: 56

Cys Ala Arg Glu Arg Tyr Gly Tyr Tyr Phe Asp Tyr Trp Gly Gln
1               5                   10                  15

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 57

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 58

Ile Thr Cys Arg Ala Ser Gln Tyr Val Gly Ser Tyr Leu Asn Trp Tyr
1               5                   10                  15

Gln

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR2 antibody region peptide

<400> SEQUENCE: 59

```
Leu Ile Tyr Asp Ala Ser Asn Arg Ala Thr Gly Ile Pro
1               5                   10
```

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 & AX213 light chain CDR3 antibody region peptide

<400> SEQUENCE: 60

```
Tyr Tyr Cys Gln Val Trp Asp Ser Ser Pro Pro Val Val Phe Gly Gly
1               5                   10                  15
```

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
        115                 120
```

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      AX213 heavy chain CDR1 antibody region peptide

<400> SEQUENCE: 62

```
Lys Ala Ser Gly Tyr Thr Phe Ser Arg Tyr Gly Ile Asn Trp Val Arg
1               5                   10                  15
```

<210> SEQ ID NO 63

```
<211> LENGTH: 23
<212> TYPE: PRT
<213> ORGANISM: Artificial Sequence
<220> FEATURE:
<223> OTHER INFORMATION: Description of Artificial Sequence: Synthetic
      AX213 heavy chain CDR2 antibody region peptide

<400> SEQUENCE: 63

Trp Ile Gly Arg Ile Asp Pro Gly Asn Gly Gly Thr Arg Tyr Asn Glu
1               5                   10                  15

Lys Phe Lys Gly Lys Ala Thr
            20

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      AX213 heavy chain CDR3 antibody region peptide

<400> SEQUENCE: 64

Cys Ala Arg Ala Asn Asp Gly Tyr Ser Phe Asp Tyr Trp Gly Gln
1               5                   10                  15

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 65

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 66

Ile Thr Cys Arg Ala Ser Gln Tyr Val Gly Ser Tyr Leu Asn Trp Tyr
1               5                   10                  15

Gln

<210> SEQ ID NO 67
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR2 antibody region peptide

<400> SEQUENCE: 67

Leu Ile Tyr Asp Ala Ser Asn Arg Ala Thr Gly Ile Pro
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 & AX213 light chain CDR3 antibody region peptide

<400> SEQUENCE: 68

Tyr Tyr Cys Gln Val Trp Asp Ser Ser Pro Pro Val Val Phe Gly Gly
1               5                   10                  15

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
      AX1 VH antibody sequence polypeptide

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30

Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser
        115

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      AX1 VH CDR1 antibody sequence peptide

<400> SEQUENCE: 70

Lys Ala Ser Gly Phe Thr Phe Thr Ser Tyr Tyr Met His Trp Val Arg
1               5                   10                  15

<210> SEQ ID NO 71
<211> LENGTH: 23
<212> TYPE: PRT
```

<213> ORGANISM: Artificial Sequence
<220> FEATURE:
<223> OTHER INFORMATION: Description of Artificial Sequence: Synthetic
      AX1 VH CDR2 antibody sequence peptide

<400> SEQUENCE: 71

Trp Ile Gly Arg Ile Asn Pro Asp Ser Gly Ser Thr Lys Tyr Asn Glu
1               5                   10                  15

Lys Phe Lys Gly Arg Ala Thr
            20

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      AX1 VH CDR3 antibody sequence peptide

<400> SEQUENCE: 72

Cys Ala Arg Gly Gly Arg Leu Ser Trp Asp Phe Asp Val Trp Gly Gln
1               5                   10                  15

<210> SEQ ID NO 73
<211> LENGTH: 109
<212> TYPE: PRT
<213> ORGANISM: Artificial Sequence
<220> FEATURE:
<223> OTHER INFORMATION: Description of Artificial Sequence: Synthetic
      AX1 VL antibody sequence polypeptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys
            100                 105

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR1 antibody sequence peptide

<400> SEQUENCE: 74

Arg Ala Ser Gln Asp Ile Ser Arg Tyr Leu Ala
1               5                   10

<210> SEQ ID NO 75
<211> LENGTH: 7
<212> TYPE: PRT
<213> ORGANISM: Artificial Sequence
<220> FEATURE:

<223> OTHER INFORMATION: Description of Artificial Sequence: Synthetic
      AX1 AX9 AX189 VL CDR2 antibody sequence peptide

<400> SEQUENCE: 75

Ala Ala Ser Ser Leu Gln Ser
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR3 antibody sequence peptide

<400> SEQUENCE: 76

Ala Ala Tyr Asp Tyr Ser Leu Gly Gly Tyr Val
1               5                   10

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      AX9 AX189 VH antibody sequence polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      AX9 AX189 VH CDR1 antibody sequence peptide

<400> SEQUENCE: 78

Lys Ala Ser Gly Tyr Thr Phe Ser Ser Tyr Trp Met His Trp Val Arg
1               5                   10                  15

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
      AX9 AX189 VH CDR2 antibody sequence peptide

<400> SEQUENCE: 79

Trp Ile Gly Arg Ile Asp Pro Tyr Asn Gly Gly Thr Lys Tyr Asn Glu
1               5                   10                  15

Lys Phe Lys Gly Lys Ala Thr
            20

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      AX9 AX189 VH CDR3 antibody sequence peptide

<400> SEQUENCE: 80

Cys Ala Arg Tyr Gly Tyr Tyr Leu Gly Ser Tyr Ala Met Asp Tyr Trp
1               5                   10                  15

Gly Gln

<210> SEQ ID NO 81
<211> LENGTH: 109
<212> TYPE: PRT
<213> ORGANISM: Artificial Sequence
<220> FEATURE:
<223> OTHER INFORMATION: Description of Artificial Sequence: Synthetic
      AX189 VL antibody sequence polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys
            100                 105

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      AX189 VL CDR1 antibody sequence peptide

<400> SEQUENCE: 82

Arg Ala Ser Gln Asp Val Ser Arg Tyr Leu Thr
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      AX1 AX9 AX189 VL CDR2 antibody sequence peptide

<400> SEQUENCE: 83

Ala Ala Ser Ser Leu Gln Ser
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      AX189 VL CDR3 antibody sequence peptide

<400> SEQUENCE: 84

Gln Ala Tyr Asp Tyr Ser Leu Ser Gly Tyr Val
1               5                   10

<210> SEQ ID NO 85
<211> LENGTH: 115
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 86
<211> LENGTH: 5
<212> TYPE: PRT
<213> ORGANISM: Homo sapiens

<400> SEQUENCE: 86

Ser Tyr Gly Ile Ser
1               5

<210> SEQ ID NO 87
<211> LENGTH: 17
<212> TYPE: PRT
<213> ORGANISM: Homo sapiens

<400> SEQUENCE: 87

Trp Val Ser Phe Tyr Asn Gly Asn Thr Asn Tyr Ala Gln Lys Leu Gln
1               5                   10                  15

Gly

<210> SEQ ID NO 88
<211> LENGTH: 6

```
<212> TYPE: PRT
<213> ORGANISM: Homo sapiens

<400> SEQUENCE: 88

Gly Tyr Gly Met Asp Val
1               5

<210> SEQ ID NO 89
<211> LENGTH: 109
<212> TYPE: PRT
<213> ORGANISM: Homo sapiens

<400> SEQUENCE: 89

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 90
<211> LENGTH: 14
<212> TYPE: PRT
<213> ORGANISM: Homo sapiens

<400> SEQUENCE: 90

Thr Gly Thr Ser Ser Asp Val Gly Gly Tyr Asn Ser Val Ser
1               5                   10

<210> SEQ ID NO 91
<211> LENGTH: 7
<212> TYPE: PRT
<213> ORGANISM: Homo sapiens

<400> SEQUENCE: 91

Glu Val Ser Asn Arg Pro Ser
1               5

<210> SEQ ID NO 92
<211> LENGTH: 9
<212> TYPE: PRT
<213> ORGANISM: Homo sapiens

<400> SEQUENCE: 92

Asn Ser Tyr Thr Ser Thr Ser Met Val
1               5

<210> SEQ ID NO 93
<211> LENGTH: 123
<212> TYPE: PRT
<213> ORGANISM: Homo sapiens

<400> SEQUENCE: 93

Glu Val Gln Leu Val Glu Ser Gly Gly Gly Leu Val Lys Pro Gly Gly
```

```
                1               5                  10                  15
            Ser Leu Arg Leu Ser Cys Ala Ala Ser Gly Phe Thr Phe Ser Ser Tyr
                           20                  25                  30

Ser Met Asn Trp Val Arg Gln Ala Pro Gly Lys Gly Leu Glu Trp Val
                           35                  40                  45

Ser Ser Ile Ser Ser Ser Ser Ser Tyr Ile Ser Tyr Ala Asp Ser Val
                           50                  55                  60

Lys Gly Arg Phe Thr Ile Ser Arg Asp Asn Ala Lys Asn Ser Leu Tyr
             65                 70                  75                  80

Leu Gln Met Asn Ser Leu Arg Ala Glu Asp Thr Ala Val Tyr Phe Cys
                           85                  90                  95

Ala Arg Asp Tyr Asp Phe Trp Ser Ala Tyr Tyr Asp Ala Phe Asp Val
                          100                 105                 110

Trp Gly Gln Gly Thr Met Val Thr Val Ser Ser
                          115                 120
```

<210> SEQ ID NO 94
<211> LENGTH: 10
<212> TYPE: PRT
<213> ORGANISM: Homo sapiens

<400> SEQUENCE: 94

```
Gly Phe Thr Phe Ser Ser Tyr Ser Met Asn
1               5                  10
```

<210> SEQ ID NO 95
<211> LENGTH: 17
<212> TYPE: PRT
<213> ORGANISM: Homo sapiens

<400> SEQUENCE: 95

```
Ser Ile Ser Ser Ser Ser Tyr Ile Ser Tyr Ala Asp Ser Val Lys
1               5                  10                  15
Gly
```

<210> SEQ ID NO 96
<211> LENGTH: 14
<212> TYPE: PRT
<213> ORGANISM: Homo sapiens

<400> SEQUENCE: 96

```
Asp Tyr Asp Phe Trp Ser Ala Tyr Tyr Asp Ala Phe Asp Val
1               5                  10
```

<210> SEQ ID NO 97
<211> LENGTH: 111
<212> TYPE: PRT
<213> ORGANISM: Homo sapiens

<400> SEQUENCE: 97

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Ser Gly Asn Ser Asn Arg Pro Ser Gly Val Pro Asp Arg Phe
             50                 55                  60

Ser Gly Ser Lys Ser Gly Thr Ser Ala Ser Leu Ala Ile Thr Gly Leu
```

```
                65                  70                  75                  80
Gln Ala Glu Asp Glu Ala Asp Tyr Tyr Cys Gln Ser Tyr Asp Ser Ser
                    85                  90                  95

Leu Ser Gly Ser Val Phe Gly Gly Gly Thr Lys Leu Thr Val Leu
                100                 105                 110
```

<210> SEQ ID NO 98
<211> LENGTH: 14
<212> TYPE: PRT
<213> ORGANISM: Homo sapiens

<400> SEQUENCE: 98

```
Thr Gly Ser Ser Ser Asn Ile Gly Ala Gly Tyr Asp Val His
1               5                   10
```

<210> SEQ ID NO 99
<211> LENGTH: 7
<212> TYPE: PRT
<213> ORGANISM: Homo sapiens

<400> SEQUENCE: 99

```
Gly Asn Ser Asn Arg Pro Ser
1               5
```

<210> SEQ ID NO 100
<211> LENGTH: 11
<212> TYPE: PRT
<213> ORGANISM: Homo sapiens

<400> SEQUENCE: 100

```
Gln Ser Tyr Asp Ser Ser Leu Ser Gly Ser Val
1               5                   10
```

<210> SEQ ID NO 101
<211> LENGTH: 114
<212> TYPE: PRT
<213> ORGANISM: Homo sapiens

<400> SEQUENCE: 101

```
Gln Val Gln Leu Val Glu Ser Gly Gly Gly Val Ala Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Tyr Tyr Asp Gly Ile Asn Lys His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Asp Trp Gly Gln Gly Thr Leu Val Thr Val
                100                 105                 110

Ser Ser
```

<210> SEQ ID NO 102
<211> LENGTH: 10
<212> TYPE: PRT
<213> ORGANISM: Homo sapiens

<400> SEQUENCE: 102

```
Gly Phe Thr Phe Ser Ser Tyr Gly Met His
1               5                  10

<210> SEQ ID NO 103
<211> LENGTH: 17
<212> TYPE: PRT
<213> ORGANISM: Homo sapiens

<400> SEQUENCE: 103

Val Ile Tyr Tyr Asp Gly Ile Asn Lys His Tyr Ala Asp Ser Val Lys
1               5                   10                  15

Gly

<210> SEQ ID NO 104
<211> LENGTH: 5
<212> TYPE: PRT
<213> ORGANISM: Homo sapiens

<400> SEQUENCE: 104

Asp Arg Gly Leu Asp
1               5

<210> SEQ ID NO 105
<211> LENGTH: 113
<212> TYPE: PRT
<213> ORGANISM: Homo sapiens

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Ser Lys Asn Tyr Leu Val Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
                100                 105                 110

Lys

<210> SEQ ID NO 106
<211> LENGTH: 17
<212> TYPE: PRT
<213> ORGANISM: Homo sapiens

<400> SEQUENCE: 106

Lys Ser Ser Gln Ser Val Leu Tyr Ser Ser Asn Ser Lys Asn Tyr Leu
1               5                   10                  15

Val

<210> SEQ ID NO 107
<211> LENGTH: 7
<212> TYPE: PRT
<213> ORGANISM: Homo sapiens

<400> SEQUENCE: 107
```

Trp Ala Ser Thr Arg Glu Ser
1               5

<210> SEQ ID NO 108
<211> LENGTH: 9
<212> TYPE: PRT
<213> ORGANISM: Homo sapiens

<400> SEQUENCE: 108

Gln Gln Tyr Tyr Ser Thr Pro Trp Thr
1               5

<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04 (clones LGT-209 and
      LGT-210) Vh heavy chain variable region (FR1-FR4)
      polypeptide

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Tyr Tyr Tyr Asn Met Asp Tyr Trp Gly Gln Gly Thr
            100                 105                 110

Leu Val Thr Val Ser Ser
        115

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 heavy chain CDR1 peptide

<400> SEQUENCE: 110

Thr Met Tyr Met Ser
1               5

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 heavy chain CDR2 peptide

<400> SEQUENCE: 111

```
Arg Ile Asp Pro Ala Asn Glu His Thr Asn Tyr Ala Gln Lys Phe Gln
1               5                   10                  15

Gly
```

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04(clones
      LGT-209 and LGT-210) Vh heavy chain complementarity
      determining region 3 (CDR3) peptide

<400> SEQUENCE: 112

```
Ser Tyr Tyr Tyr Tyr Asn Met Asp Tyr
1               5
```

<210> SEQ ID NO 113
<211> LENGTH: 106
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG10(clones
      LGT-209 and LGT-211) Vk light chain variable
      region (FR1-FR4) polypeptide

<400> SEQUENCE: 113

```
Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Gly Val Phe Arg Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105
```

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 light chain CDR1 peptide

<400> SEQUENCE: 114

```
Arg Ala Ser Gln Ser Val Ser Tyr Met His
1               5                   10
```

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 light chain CDR1 peptide

```
<400> SEQUENCE: 115

Gly Val Phe Arg Arg Ala Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      mouse anti-PCSK9 monoclonal antibody LFU720 and
      anti-PCSK9 monoclonal antibody clones LGT-209,
      LGT-210 and LGT-211 light chain CDR3 peptide

<400> SEQUENCE: 116

Leu Gln Trp Ser Ser Asp Pro Pro Thr
1               5

<210> SEQ ID NO 117
<211> LENGTH: 118
<212> TYPE: PRT
<213> ORGANISM: Homo sapiens

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Tyr Thr Phe Thr Ser Tyr
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

```
Ser Pro Phe Gly Gly Arg
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      variable heavy chain CDR peptide

<400> SEQUENCE: 120

Glu Arg Pro Leu Tyr Ala Ser Asp Leu
1               5

<210> SEQ ID NO 121
<211> LENGTH: 107
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 122

Arg Ala Ser Gln Gly Ile Ser Ser Ala Leu Ala
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 123

Ser Ala Ser Tyr Arg Tyr Thr
1               5

<210> SEQ ID NO 124
<211> LENGTH: 9
<212> TYPE: PRT
<213> ORGANISM: Artificial Sequence
```

<220> FEATURE:
<223> OTHER INFORMATION: Description of Artificial Sequence: Synthetic
      variable light chain CDR peptide

<400> SEQUENCE: 124

Gln Gln Arg Tyr Ser Leu Trp Arg Thr
1               5

<210> SEQ ID NO 125
<211> LENGTH: 118
<212> TYPE: PRT
<213> ORGANISM: Homo sapiens

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile His Pro Ser Gly Gly Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Met Asp Tyr Trp Gly Gln Gly Thr
                100                 105                 110

Thr Val Thr Val Ser Ser
            115

<210> SEQ ID NO 126
<211> LENGTH: 10
<212> TYPE: PRT
<213> ORGANISM: Homo sapiens

<400> SEQUENCE: 126

Gly Tyr Thr Phe Thr Ser Tyr Tyr Met His
1               5                   10

<210> SEQ ID NO 127
<211> LENGTH: 17
<212> TYPE: PRT
<213> ORGANISM: Homo sapiens

<400> SEQUENCE: 127

Glu Ile His Pro Ser Gly Gly Arg Thr Asn Tyr Asn Glu Lys Phe Lys
1               5                   10                  15

Ser

<210> SEQ ID NO 128
<211> LENGTH: 9
<212> TYPE: PRT
<213> ORGANISM: Homo sapiens

<400> SEQUENCE: 128

Glu Arg Pro Leu Tyr Ala Met Asp Tyr
1               5

<210> SEQ ID NO 129
<211> LENGTH: 107

<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 130
<211> LENGTH: 11
<212> TYPE: PRT
<213> ORGANISM: Homo sapiens

<400> SEQUENCE: 130

Lys Ala Ser Gln Asp Val His Thr Ala Val Ala
1               5                   10

<210> SEQ ID NO 131
<211> LENGTH: 7
<212> TYPE: PRT
<213> ORGANISM: Homo sapiens

<400> SEQUENCE: 131

His Ala Ser Tyr Arg Tyr Thr
1               5

<210> SEQ ID NO 132
<211> LENGTH: 9
<212> TYPE: PRT
<213> ORGANISM: Homo sapiens

<400> SEQUENCE: 132

Gln Gln Arg Tyr Ser Leu Trp Arg Thr
1               5

<210> SEQ ID NO 133
<211> LENGTH: 118
<212> TYPE: PRT
<213> ORGANISM: Homo sapiens

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Arg Thr Asn Tyr Asn Glu Lys Phe
    50                  55                  60

```
Lys Ser Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Arg Pro Leu Tyr Ala Ser Asp Leu Trp Gly Gln Gly Thr
            100                 105                 110

Thr Val Thr Val Ser Ser
            115

<210> SEQ ID NO 134
<211> LENGTH: 10
<212> TYPE: PRT
<213> ORGANISM: Homo sapiens

<400> SEQUENCE: 134

Gly Tyr Thr Phe Thr Ser Tyr Tyr Met His
1               5                   10

<210> SEQ ID NO 135
<211> LENGTH: 17
<212> TYPE: PRT
<213> ORGANISM: Homo sapiens

<400> SEQUENCE: 135

Glu Ile His Pro Ser Gly Gly Arg Thr Asn Tyr Asn Glu Lys Phe Lys
1               5                   10                  15

Ser

<210> SEQ ID NO 136
<211> LENGTH: 9
<212> TYPE: PRT
<213> ORGANISM: Homo sapiens

<400> SEQUENCE: 136

Glu Arg Pro Leu Tyr Ala Ser Asp Leu
1               5

<210> SEQ ID NO 137
<211> LENGTH: 107
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 138
<211> LENGTH: 11
```

```
<212> TYPE: PRT
<213> ORGANISM: Homo sapiens

<400> SEQUENCE: 138

Lys Ala Ser Gln Asp Val His Thr Ala Val Ala
1               5                   10

<210> SEQ ID NO 139
<211> LENGTH: 7
<212> TYPE: PRT
<213> ORGANISM: Homo sapiens

<400> SEQUENCE: 139

His Ala Ser Tyr Arg Tyr Thr
1               5

<210> SEQ ID NO 140
<211> LENGTH: 9
<212> TYPE: PRT
<213> ORGANISM: Homo sapiens

<400> SEQUENCE: 140

Gln Gln Arg Tyr Ser Leu Trp Arg Thr
1               5

<210> SEQ ID NO 141
<211> LENGTH: 118
<212> TYPE: PRT
<213> ORGANISM: Mus musculus

<400> SEQUENCE: 141

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Arg Pro Leu Tyr Ala Met Asp Tyr Trp Gly Gln Gly Thr
            100                 105                 110

Ser Val Thr Val Ser Ser
        115

<210> SEQ ID NO 142
<211> LENGTH: 7
<212> TYPE: PRT
<213> ORGANISM: Mus musculus

<400> SEQUENCE: 142

Gly Tyr Thr Phe Thr Ser Tyr
1               5

<210> SEQ ID NO 143
<211> LENGTH: 6
<212> TYPE: PRT
<213> ORGANISM: Mus musculus
```

<400> SEQUENCE: 143

Asn Pro Ser Asn Gly Arg
1               5

<210> SEQ ID NO 144
<211> LENGTH: 9
<212> TYPE: PRT
<213> ORGANISM: Mus musculus

<400> SEQUENCE: 144

Glu Arg Pro Leu Tyr Ala Met Asp Tyr
1               5

<210> SEQ ID NO 145
<211> LENGTH: 108
<212> TYPE: PRT
<213> ORGANISM: Mus musculus

<400> SEQUENCE: 145

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Arg Tyr Ser Thr Pro Arg
                85                  90                  95

Thr Phe Gly Gly Gly Thr Lys Leu Glu Ile Lys Arg
            100                 105

<210> SEQ ID NO 146
<211> LENGTH: 11
<212> TYPE: PRT
<213> ORGANISM: Mus musculus

<400> SEQUENCE: 146

Lys Ala Ser Gln Asp Val Ser Thr Ala Val Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 147

Ser Ala Ser Tyr Arg Tyr Thr
1               5

<210> SEQ ID NO 148
<211> LENGTH: 9
<212> TYPE: PRT
<213> ORGANISM: Mus musculus

<400> SEQUENCE: 148

Gln Gln Arg Tyr Ser Thr Pro Arg Thr

```
<210> SEQ ID NO 149
<211> LENGTH: 115
<212> TYPE: PRT
<213> ORGANISM: Mus musculus

<400> SEQUENCE: 149

Glu Val Gln Leu Gln Gln Ser Gly Pro Glu Leu Val Lys Pro Gly Ala
1               5                   10                  15
Ser Val Lys Ile Ser Cys Lys Ala Ser Gly Tyr Thr Phe Thr Asp Tyr
            20                  25                  30
Tyr Met Asn Trp Val Lys Gln Ser His Gly Lys Ser Leu Glu Trp Ile
        35                  40                  45
Gly Asp Ile Asn Pro Asn Asn Gly Gly Thr Thr Tyr Asn Gln Lys Phe
    50                  55                  60
Lys Gly Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Arg Trp Leu Leu Phe Ala Tyr Trp Gly Gln Gly Thr Leu Val Thr
            100                 105                 110
Val Ser Ala
        115

<210> SEQ ID NO 150
<211> LENGTH: 7
<212> TYPE: PRT
<213> ORGANISM: Mus musculus

<400> SEQUENCE: 150

Gly Tyr Thr Phe Thr Asp Tyr
1               5

<210> SEQ ID NO 151
<211> LENGTH: 6
<212> TYPE: PRT
<213> ORGANISM: Mus musculus

<400> SEQUENCE: 151

Asn Pro Asn Asn Gly Gly
1               5

<210> SEQ ID NO 152
<211> LENGTH: 6
<212> TYPE: PRT
<213> ORGANISM: Mus musculus

<400> SEQUENCE: 152

Trp Leu Leu Phe Ala Tyr
1               5

<210> SEQ ID NO 153
<211> LENGTH: 108
<212> TYPE: PRT
<213> ORGANISM: Mus musculus

<400> SEQUENCE: 153

Asp Ile Val Met Thr Gln Ser Gln Lys Phe Met Ser Thr Ser Val Gly
1               5                   10                  15
Asp Arg Val Ser Val Thr Cys Lys Ala Ser Gln Asn Val Gly Thr Asn
```

```
                20                  25                  30
Val Ala Trp Tyr Gln Gln Lys Pro Gly Gln Ser Pro Lys Ala Leu Ile
            35                  40                  45
Tyr Ser Ala Ser Tyr Arg Tyr Ser Gly Val Pro Asp Arg Phe Thr Gly
        50                  55                  60
Ser Gly Ser Gly Thr Asp Phe Thr Leu Thr Ile Ser Asn Val Leu Ser
65                  70                  75                  80
Glu Asp Leu Ala Glu Tyr Phe Cys Gln Gln Phe Tyr Ser Tyr Pro Tyr
                85                  90                  95
Thr Phe Gly Gly Gly Thr Lys Leu Glu Ile Lys Arg
                100                 105
```

<210> SEQ ID NO 154
<211> LENGTH: 11
<212> TYPE: PRT
<213> ORGANISM: Mus musculus

<400> SEQUENCE: 154

```
Lys Ala Ser Gln Asn Val Gly Thr Asn Val Ala
1               5                   10
```

<210> SEQ ID NO 155
<211> LENGTH: 7
<212> TYPE: PRT
<213> ORGANISM: Mus musculus

<400> SEQUENCE: 155

```
Ser Ala Ser Tyr Arg Tyr Ser
1               5
```

<210> SEQ ID NO 156
<211> LENGTH: 9
<212> TYPE: PRT
<213> ORGANISM: Mus musculus

<400> SEQUENCE: 156

```
Gln Gln Phe Tyr Ser Tyr Pro Tyr Thr
1               5
```

<210> SEQ ID NO 157
<211> LENGTH: 123
<212> TYPE: PRT
<213> ORGANISM: Mus musculus

<400> SEQUENCE: 157

```
Glu Val Gln Leu Gln Gln Ser Gly Pro Glu Leu Val Lys Pro Gly Ala
1               5                   10                  15
Ser Val Lys Ile Ser Cys Lys Ala Ser Gly Tyr Thr Phe Thr Asp Tyr
                20                  25                  30
Tyr Met Asn Trp Val Lys Gln Ser His Gly Lys Ser Leu Glu Trp Ile
            35                  40                  45
Gly Asp Ile Asn Pro Asn Gly Gly Thr Ser Tyr Asn Gln Lys Phe
        50                  55                  60
Lys Gly Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Gly Gly Gly Ile Tyr Tyr Arg Tyr Asp Arg Asn Tyr Phe Asp Tyr
                100                 105                 110
```

Trp Gly Gln Gly Thr Thr Leu Thr Val Ser Ser
            115                 120

<210> SEQ ID NO 158
<211> LENGTH: 7
<212> TYPE: PRT
<213> ORGANISM: Mus musculus

<400> SEQUENCE: 158

Gly Tyr Thr Phe Thr Asp Tyr
1               5

<210> SEQ ID NO 159
<211> LENGTH: 6
<212> TYPE: PRT
<213> ORGANISM: Mus musculus

<400> SEQUENCE: 159

Asn Pro Asn Asn Gly Gly
1               5

<210> SEQ ID NO 160
<211> LENGTH: 14
<212> TYPE: PRT
<213> ORGANISM: Mus musculus

<400> SEQUENCE: 160

Gly Gly Ile Tyr Tyr Arg Tyr Asp Arg Asn Tyr Phe Asp Tyr
1               5                   10

<210> SEQ ID NO 161
<211> LENGTH: 107
<212> TYPE: PRT
<213> ORGANISM: Mus musculus

<400> SEQUENCE: 161

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Phe
                85                  90                  95

Thr Phe Gly Ser Gly Thr Lys Leu Glu Ile Lys
            100                 105

<210> SEQ ID NO 162
<211> LENGTH: 11
<212> TYPE: PRT
<213> ORGANISM: Mus musculus

<400> SEQUENCE: 162

Ser Ala Ser Gln Gly Ile Ser Asn Tyr Leu Asn
1               5                   10

<210> SEQ ID NO 163
<211> LENGTH: 7

<212> TYPE: PRT
<213> ORGANISM: Mus musculus

<400> SEQUENCE: 163

Tyr Thr Ser Ser Leu His Ser
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Tyr Ser Lys Leu Pro Phe Thr
1               5

<210> SEQ ID NO 165
<211> LENGTH: 117
<212> TYPE: PRT
<213> ORGANISM: Mus musculus

<400> SEQUENCE: 165

Glu Val Lys Leu Val Glu Ser Gly Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Asn Thr Ser Tyr Leu Asp Ser Leu
        50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Glu Lys Phe Ala Ala Met Asp Tyr Trp Gly Gln Gly Thr Ser
            100                 105                 110

Val Thr Val Ser Ser
        115

<210> SEQ ID NO 166
<211> LENGTH: 7
<212> TYPE: PRT
<213> ORGANISM: Mus musculus

<400> SEQUENCE: 166

Gly Phe Thr Phe Ser Asp Tyr
1               5

<210> SEQ ID NO 167
<211> LENGTH: 6
<212> TYPE: PRT
<213> ORGANISM: Mus musculus

<400> SEQUENCE: 167

Asn Tyr Asp Gly Ser Asn
1               5

<210> SEQ ID NO 168
<211> LENGTH: 8

```
<212> TYPE: PRT
<213> ORGANISM: Mus musculus

<400> SEQUENCE: 168

Glu Lys Phe Ala Ala Met Asp Tyr
1               5

<210> SEQ ID NO 169
<211> LENGTH: 108
<212> TYPE: PRT
<213> ORGANISM: Mus musculus

<400> SEQUENCE: 169

Asp Ile Val Met Thr Gln Ser His Lys Phe Met Ser Thr Ser Phe Gly
1               5                   10                  15

Asp Arg Val Ser Ile Thr Cys Lys Ala Ser Gln Asp Val Ser Asn Ala
            20                  25                  30

Leu Ala Trp Tyr Gln Gln Lys Pro Gly His Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys Arg
            100                 105

<210> SEQ ID NO 170
<211> LENGTH: 11
<212> TYPE: PRT
<213> ORGANISM: Mus musculus

<400> SEQUENCE: 170

Lys Ala Ser Gln Asp Val Ser Asn Ala Leu Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 171

Ser Ala Ser Tyr Arg Tyr Thr
1               5

<210> SEQ ID NO 172
<211> LENGTH: 9
<212> TYPE: PRT
<213> ORGANISM: Mus musculus

<400> SEQUENCE: 172

Gln Gln His Tyr Ser Thr Pro Trp Thr
1               5

<210> SEQ ID NO 173
<211> LENGTH: 121
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
            20                  25                  30

Thr Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Phe Thr Phe Thr Arg His Thr Ile His
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Ile Ser Pro Ala Asn Gly Asn Thr Asn Tyr Ala Asp Ser Val Lys
1               5                   10                  15

Gly

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Ile Gly Ser Arg Glu Leu Tyr Ile Met Asp Tyr
1               5                   10

<210> SEQ ID NO 177
<211> LENGTH: 108
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 177

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Ile Gln Pro
                85                  90                  95

Thr Phe Gly Gln Gly Thr Lys Val Glu Ile Lys Arg
            100                 105
```

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 178

```
Arg Ala Ser Gln Asp Val Ser Thr Ala Val Ala
1               5                   10
```

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

```
Ser Ala Ser Phe Leu Tyr Ser
1               5
```

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

```
Gln Gln Ser Tyr Arg Ile Gln Pro Thr
1               5
```

<210> SEQ ID NO 181
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 181

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Ala Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120
```

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Gly Phe Thr Phe Ser Ser Thr Ala Ile His
1               5                   10
```

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Arg Ile Ser Pro Ala Asn Gly Asn Thr Asn Tyr Ala Asp Ser Val Lys
1               5                   10                  15

Gly
```

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Trp Ile Gly Ser Arg Glu Leu Tyr Ile Met Asp Tyr
1               5                   10
```

<210> SEQ ID NO 185
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Leu His
                85                  90                  95

Thr Phe Gly Gln Gly Thr Lys Val Glu Ile Lys Arg
            100                 105
```

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

```
Arg Ala Ser Gln Asp Val Ser Thr Ala Val Ala
1               5                   10
```

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Ser Ala Ser Phe Leu Tyr Ser
1               5
```

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

```
Gln Gln Ser Tyr Pro Ala Leu His Thr
1               5
```

<210> SEQ ID NO 189
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Lys Leu
            20                  25                  30
```

```
Gly Met Val Trp Val Arg Gln Ala Pro Gly Lys Gly Leu Glu Trp Val
            35                  40                  45

Ser Thr Ile Ser Ser Gly Gly Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser
            115                 120                 125

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Pro Phe Ser Lys Leu Gly Met Val
1               5                   10

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Ile Ser Ser Gly Gly Gly Tyr Thr Tyr Tyr Pro Asp Ser Val Lys
1               5                   10                  15

Gly

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Glu Gly Ile Ser Phe Gln Gly Gly Thr Tyr Thr Tyr Val Met Asp Tyr
1               5                   10                  15

<210> SEQ ID NO 193
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30
```

Asn Gly Ile Thr Tyr Ser Tyr Trp Tyr Leu Gln Lys Pro Gly Gln Ser
         35                  40                  45

Pro Gln Leu Leu Ile Tyr Gln Leu Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Tyr Gln Asn
                 85                  90                  95

Leu Glu Leu Pro Leu Thr Phe Gly Gln Gly Thr Lys Val Glu Ile Lys
            100                 105                 110

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ser Ser Lys Ser Leu Leu His Arg Asn Gly Ile Thr Tyr Ser Tyr
 1               5                  10                  15

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Leu Ser Asn Leu Ala Ser
 1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Tyr Gln Asn Leu Glu Leu Pro Leu Thr
 1               5

<210> SEQ ID NO 197
<211> LENGTH: 2076
<212> TYPE: DNA
<213> ORGANISM: Homo sapiens

<400> SEQUENCE: 197
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgttc cgaggaggac ggcctggccg aagcacccga gcacggaacc     180
acagccacct tccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc gccggggata cctcaccaag atcctgcatg tcttccatgg ccttcttcct     360
ggcttcctgg tgaagatgag tggcgacctg ctggagctgg ccttgaagtt gccccatgtc     420

```
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg cagggtgtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact ttggggacca actttggccg ctgtgtggac   1080
ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc ggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccatggg gcaggttggc agctgttttg caggactgta   1380
tggtcagcac actcggggcc tacacggatg gccacagccg tcgcccgctg cgccccagat   1440
gaggagctgc tgagctgctc cagtttctcc aggagtggga gcggcgggg cgagcgcatg   1500
gaggcccaag ggggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctgggggc ctacgccgta gacaacacgt gtgtagtcag gagccgggac   1980
gtcagcacta caggcagcac cagcgaaggg gccgtgacag ccgttgccat ctgctgccgg   2040
agccggcacc tggcgcaggc ctcccaggag ctccag                             2076
```

<210> SEQ ID NO 198
<211> LENGTH: 692
<212> TYPE: PRT
<213> ORGANISM: Homo sapiens

<400> SEQUENCE: 198

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

-continued

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

-continued

```
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
    530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
        610             615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
            645                 650                 655
Arg Ser Arg Asp Val Ser Thr Thr Gly Ser Thr Ser Glu Gly Ala Val
            660                 665                 670
Thr Ala Val Ala Ile Cys Cys Arg Ser Arg His Leu Ala Gln Ala Ser
            675                 680                 685
Gln Glu Leu Gln
    690
```

DOSING REGIMENS FOR USE WITH PCSK9 INHIBITORS

RELATED APPLICATIONS

This application is related to U.S. Provisional Patent Application No. 61/902,857 filed Nov. 12, 2013, U.S. Provisional Patent Application No. 61/955,337 filed Mar. 19, 2014, and European Patent Application No. 14306222.2 filed Jul. 31, 2014, the contents of each of which are incorporated herein by reference in their entirety.

FIELD OF THE INVENTION

The present invention relates to the field of therapeutic treatment for a PCSK9-mediated disease or a PCSK9-mediated condition. Specifically, the invention relates to methods comprising the administration of a proprotein convertase subtilisin/kexin type 9 (PCSK9) antagonist, e.g., an anti-PCSK9 antibody or antigen binding protein, in the absence of a statin to a subject in need thereof. The invention also relates to methods comprising the administration of a high dose, low frequency dosing regimen of a PCSK9 antibody or antigen binding protein to a subject who is not taking a concomitant statin.

SEQUENCE LISTING

A sequence listing is enclosed herewith and incorporated herein by reference in its entirety.

BACKGROUND

Hypercholesterolemia, particularly an increase in low-density lipoprotein cholesterol (LDL-C) levels, constitutes a major risk for the development of atherosclerosis and coronary heart disease (CHD), the leading cause of death and disability in the Western world. Numerous studies have demonstrated that reducing LDL-C levels, mainly with 3-hydroxy-3-methyl-glutaryl-CoA reductase (HMG CoA) inhibitors (commonly referred to as statins), reduces the risk of CHD, with a strong direct relationship between LDL-C levels and CHD events; for each 1 mmol/L (~40 mg/dL) reduction in LDL-C, cardiovascular disease (CVD) mortality and morbidity is lowered by 22%. Greater reductions in LDL-C produce greater reduction in events, and comparative data of intensive versus standard statin treatment suggest that the lower the LDL-C level, the greater the benefit in patients at high cardiovascular risk.

The long-term elevations of LDL-C leading to a progressive accumulation of coronary atherosclerosis require a long-term management, which includes lifestyle measures as the primary intervention. However, since lifestyle measures rarely reduce plasma LDL-C by >15%, use of pharmacologic treatments are needed to adequately treat dyslipidemic patients. Current LDL-C lowering medications include statins, ezetimibe (EZE), fibrates, niacin, and bile acid sequestrants, of which statins are the most commonly prescribed, as they have shown a great ability to lower LDL-C and reduce CHD events. Since hypercholesterolemia is largely asymptomatic, side effects of pharmacologic agents used to manage it can undermine patient compliance. In several cohort studies, the reported rate of adherence to statin therapy at 1 year ranged from 26% to 85%, with a rapid decline in adherence rates typically observed within the first few months.

Despite the widespread availability of lipid-modifying therapies, such as statins, approximately 30% of all adult patients treated for hypercholesterolemia in the United States between 1999 and 2006 failed to achieve their recommended LDL-C targets. Reasons for this include poor adherence to therapy, drug-resistance/intolerance, and the positive relationship between adverse event rates and increasing dosage. Moreover, since the most effective lipid-modifying therapies can only reduce LDL-C levels by up to 55%, target attainment rates in patients that require substantial reductions in LDL-C, such as those with familial hypercholesterolemia, are often significantly lower than might be expected. More effective lipid-modifying therapies and treatment regimens are therefore required to improve target attainment rates in these patients.

Proprotein convertase subtilisin/kexin type 9 (PCSK9) is a proprotein convertase belonging to the proteinase K subfamily of the secretory subtilase family. Evidence suggests that PCSK9 increases plasma LDL cholesterol by promoting degradation of the LDL receptor, which mediates LDL endocytosis in the liver, the major route of LDL clearance from circulation.

The use of PCSK9 inhibitors (anti-PCSK9 antibodies) to reduce serum total cholesterol, LDL cholesterol, and serum triglycerides has been described in U.S. Pat. Nos. 8,062,640 and 8,357,371, and U.S. Patent Application Publication No. 2013/0064834. However, there remains a need in the art for improved therapeutic methods.

BRIEF SUMMARY OF THE INVENTION

The present invention addresses the need in the art for improved therapeutic methods by establishing the beneficial effects of administering a PCSK9 antibody or antigen binding protein to a subject in the absence of a statin at a lower frequency. The present invention provides methods for treating hypercholesterolemia and/or reducing LDL-cholesterol by administering a high dose, low frequency dosing regimen of an anti-PCSK9 antibody, in the absence of statin.

One embodiment provides a method for reducing low-density lipoprotein cholesterol (LDL-C) in a subject in need thereof by administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses, thereby reducing the LDL-C in the subject.

Another embodiment provides a method for treating hypercholesterolemia in a subject in need thereof by administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses, thereby treating the hypercholesterolemia in the subject.

One embodiment provides a method for maintaining constant low-density lipoprotein cholesterol (LDL-C) lowering throughout an interdosing interval in a subject by administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses. The invention also provides a method for increasing the duration of action of a proprotein convertase subtilisin/kexin type 9 (PCSK9) antagonist in a subject by administering to the subject a PCSK9 antagonist in the absence of a statin.

In some embodiments, the subject has heterozygous Familial Hypercholesterolemia (heFH). In other embodiments, the subject has a form of hypercholesterolemia that is not Familial Hypercholesterolemia (nonFH).

The present invention also includes a method for treating a form of hypercholesterolemia that is not Familial Hypercholesterolemia in a subject in need thereof by administering to the subject a pharmaceutical composition comprising an anti-proprotein convertase subtilisin/kexin type 9 (anti-PCSK9) antibody or antigen-binding protein at a dose of about 150 mg every 4 weeks for at least 3 doses, thereby treating the form of hypercholesterolemia that is not Familial Hypercholesterolemia in the subject.

In some embodiments, subject is on a non-statin lipid-lowering agent before and/or during administration of the antibody or antigen-binding protein. In some embodiments, the non-statin lipid-lowering agent is selected from the group consisting of: ezetimibe, a fibrate, fenofibrate, niacin, an omega-3 fatty acid, and a bile acid resin. In specific embodiments, the non-statin lipid-lowering agent is ezetimibe or fenofibrate. In other embodiments, the subject is not on a non-statin lipid-lowering agent before and/or during administration of the antibody or antigen-binding protein.

In some embodiments, the PCSK9 antibody or antigen-binding fragment thereof comprises the heavy and light chain complementarity determining regions (CDRs) of a heavy chain variable region/light chain variable region (HCVR/LCVR) amino acid sequence pair selected from the group consisting of SEQ ID NOs: 1/6 and 11/15. In some aspects, the antibody or antigen-binding fragment thereof comprises heavy and light chain CDR amino acid sequences having SEQ ID NOs:12, 13, 14, 16, 17, and 18. In some aspects, the antibody or antigen-binding fragment thereof comprises an HCVR having the amino acid sequence of SEQ ID NO:11 and an LCVR having the amino acid sequence of SEQ ID NO:15. In some aspects, the antibody or antigen-binding fragment thereof comprises heavy and light chain CDR amino acid sequences having SEQ ID NOs:2, 3, 4, 7, 8, and 10. In some aspects, the antibody or antigen-binding fragment thereof comprises an HCVR having the amino acid sequence of SEQ ID NO:1 and an LCVR having the amino acid sequence of SEQ ID NO:6.

In certain aspects of the invention, the antibody or antigen-binding fragment thereof binds to the same epitope on PCSK9 as an antibody comprising heavy and light chain CDR amino acid sequences having SEQ ID NOs:12, 13, 14, 16, 17, and 18; or SEQ ID NOs: 2, 3, 4, 7, 8, and 10.

In certain aspects of the invention, the antibody or antigen-binding fragment thereof competes for binding to PCSK9 with an antibody comprising heavy and light chain CDR amino acid sequences having SEQ ID NOs:12, 13, 14, 16, 17, and 18; or SEQ ID NOs:2, 3, 4, 7, 8, and 10.

The methods of the invention include administering an anti-PCSK9 antibody or antigen-binding protein to a subject at a dose of about 150 mg every 4 weeks for at least three doses. In certain embodiments, the antibody is administered at a dose of about 150 mg every four weeks for three doses, and the dose remains at about 150 mg every four weeks if the subject's LDL-C value is less than a target LDL-C level. In some embodiments, the LDL-C of the subject is measured twelve weeks after the subject received the first dose of the antibody or antigen-binding protein. In some embodiments, the target LDL-C level is less than 70 milligrams per deciliter (mg/dL). In alternative embodiments, the target LDL-C level is less than 70 milligrams per deciliter (mg/dL) and a 30% reduction of LDL-C. In other embodiments, the target LDL-C level is less than 100 milligrams per deciliter (mg/dL) In alternative embodiments, the target LDL-C level is less than 100 milligrams per deciliter (mg/dL) and a 30% reduction of LDL-C.

The methods of the invention include administering an anti-PCSK9 antibody or antigen-binding protein by injection, including by subcutaneous injection.

In some embodiments, the method reduces the levels of one or more of apolipoprotein B (ApoB), non-high density lipoprotein cholesterol (non-HDL-C), total cholesterol (TC), lipoprotein a (Lp(a)), high-density lipoprotein cholesterol (HDL-C), triglyceride (TG), or Apolipoprotein A-1 (Apo A-1) in a subject.

In certain embodiments, the subject exhibits one or more symptoms or indicia of hypercholesterolemia or has been diagnosed with hypercholesterolemia, or would benefit from a reduction in total serum cholesterol, LDL, triglycerides, VLDL, lipoprotein(a), or would benefit from an increase in HDL.

In certain embodiments, the PCSK9-mediated disease or PCSK9-mediated condition is selected from the group consisting of elevated total cholesterol levels, elevated low-density lipoprotein cholesterol (LDL-C) levels, hyperlipidemia, dyslipidemia, atherosclerosis, cardiovascular disease, hypercholesterolemia, primary hypercholesterolemia, familial hypercholesterolemia, and hypercholesteremia which is uncontrolled by statins. In certain embodiments, the subject falls into one or more of the following groups of subjects: (i) subjects having a serum LDL cholesterol (LDL-C) level of at least 100 mg/dL, (ii) subjects having a serum HDL-C level of less than 40 mg/dL; (iii) subjects having a serum cholesterol level of at least 200 mg/dL; and (iv) subjects having a serum triacylglycerol level of at least 150 mg/dL, wherein the triacylglycerol level is determined after fasting for at least 8 hours.

The present invention also provides a pharmaceutical composition comprising a PCSK9 inhibitor for treating a subject with a PCSK9-mediated disease or a PCSK9-mediated condition, and a pharmaceutically acceptable excipient. The PCSK9 inhibitor is an antibody in certain embodiments, including an antibody comprising a heavy chain variable domain comprising the CDR amino acid sequences set forth in SEQ ID NOs:2, 3, and 4; and a light chain variable domain comprising the CDR amino acid sequences set forth in SEQ ID NOs:7, 8, and 10. In certain embodiments, the antibody comprises a heavy chain variable domain comprising the CDR amino acid sequences set forth in SEQ ID NOs:12, 13, and 14; and a light chain variable domain comprising the CDR amino acid sequences set forth in SEQ ID NOs:16, 17, and 18. In certain embodiments, the antibody comprises the heavy chain variable domain and the light chain variable domain, respectively, amino acid sequences set forth in SEQ ID NOs:1 and 6 or SEQ ID NOs:11 and 15. In certain embodiments, the pharmaceutical composition comprises a pharmaceutically acceptable excipient which is a combination of histidine, pH 6.0, polysorbate 20, and sucrose.

One embodiment provides a dosing regimen of an anti-proprotein convertase subtilisin/kexin type 9 (anti-PCSK9) antibody or antigen-binding protein that maintains a constant low-density lipoprotein cholesterol (LDL-C) lowering throughout the interdosing interval in a human subject which, following administration of the anti-PCSK9 antibody or antigen-binding protein thereof at a dose of about 150 mg every 4 weeks for at least 3 doses, has one or more of the properties selected from the group consisting of: (a) an area under the plasma concentration versus time curve calculated using the trapezoidal method from time zero to real time ($AUC_{last}$) from about 250 mg·day/L to about 650 mg·day/L; (b) a maximum plasma concentration observed ($C_{max}$) from about 15 mg/L to about 33 mg/L; (c) a first time to reach a maximum plasma concentration ($t_{max}$) of about 7 days; and (d) a time to reach terminal half life ($t_{1/2}^Z$) from about 5.5 days to about 12 days.

Another embodiment provides a dosing regimen of an anti-proprotein convertase subtilisin/kexin type 9 (anti-PCSK9) antibody or antigen-binding protein that maintains a constant low-density lipoprotein cholesterol (LDL-C) lowering throughout the interdosing interval in a human subject which, following administration of the anti-PCSK9 antibody or antigen-binding protein thereof at a dose of about 150 mg every 4 weeks for at least 3 doses, has one or more of the properties selected from the group consisting of: (a) an area under the plasma concentration versus time curve calculated using the trapezoidal method from time zero to real time ($AUC_{last}$) from about 150 mg·day/L to about 450 mg·day/L; (b) a maximum plasma concentration observed ($C_{max}$) from about 10.5 mg/L to about 24 mg/L; (c) a first time to reach a maximum plasma concentration ($t_{max}$) of about 7 days; and (d) a time to reach terminal half life ($t_{1/2}^Z$) from about 5 days to about 9 days.

BRIEF DESCRIPTION OF THE FIGURES

FIG. 5A shows the results for all three groups compared. FIG. 5B shows the results for the alirocumab+placebo group. FIG. 5C shows the results for the alirocumab+EZE group. FIG. 5D shows the results for the alirocumab+FENO group.

FIG. 7 (bottom) are two graphs showing mean alirocumab serum concentration-time profiles on Day 57 after the third alirocumab administration in linear (bottom left) and semi-log scale (bottom right) for the three groups: alirocumab+placebo, alirocumab+ezetimibe, and alirocumab+fenofibrate.

DETAILED DESCRIPTION

Figure 1:
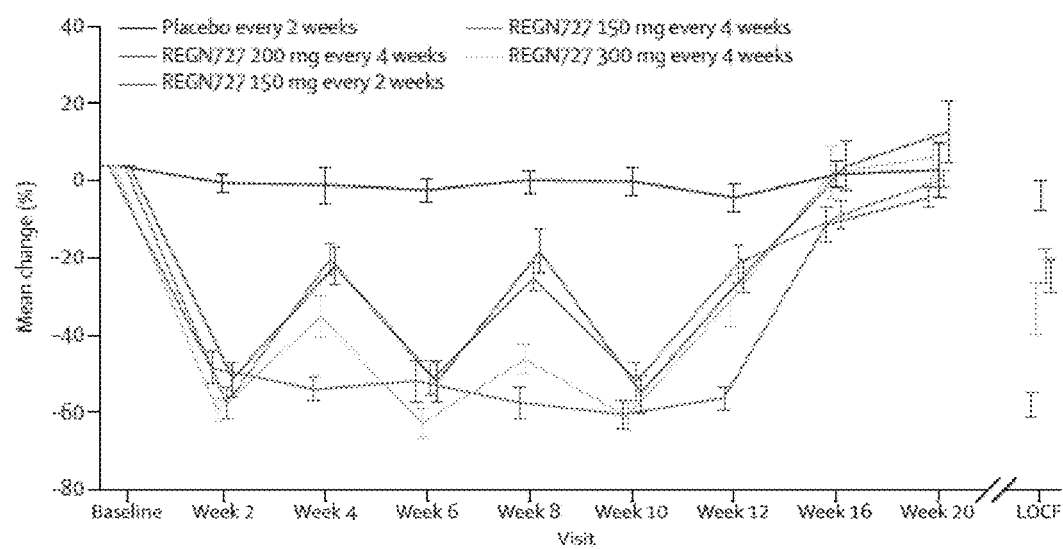
FIG. 1 is a graph of the prior art showing the mean percent change in baseline LDL-C versus week during treatment and follow-up period for patients with heterozygous familial hypercholesterolaemia given alirocumab who are on a stable statin dose with or without ezetimibe therapy. Specifically, the "saw tooth" profile of the plasma LDL-C concentration is evident, as the prior art treatments are not able to maintain constant LDL-C lowering throughout the interdosing interval.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Definitions

Unless defined otherwise, all technical and scientific terms used herein have the same meaning as is commonly understood by one of ordinary skill in the art.

It is noted here that as used in this specification and the appended claims, the singular forms "a", "an", and "the" also include plural reference, unless the context clearly dictates otherwise.

The term "about" or "approximately," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

The terms "administer" or "administration" refer to the act of injecting or otherwise physically delivering a substance as it exists outside the body (e.g., a formulation of the invention) into a patient, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

The terms "composition" and "formulation" are intended to encompass a product containing the specified ingredients (e.g., an anti-PCSK9 antibody) in, optionally, the specified amounts, as well as any product which results, directly or indirectly, from the combination of the specified ingredients in, optionally, the specified amounts.

The term "excipients" refers to inert substances that are commonly used as a diluent, vehicle, preservative, binder, stabilizing agent, etc. for drugs and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, PCSK9 fragments include polypeptides comprising an amino acid sequence of at least 50, at 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a PCSK9 polypeptide. In a specific embodiment, a fragment of a PCSK9 polypeptide or an antibody that specifically binds to a PCSK9 antigen retains at least 1, at least 2, or at least 3 functions of the full-length polypeptide or antibody.

The term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

The terms "prevent", "preventing", and "prevention" refer to the total or partial inhibition of the development, recurrence, onset or spread of a PCSK9-mediated disease and/or symptom related thereto, resulting from the administration of a therapy or combination of therapies provided herein (e.g., a combination of prophylactic or therapeutic agents).

The term "PCSK9 antigen" refers to that portion of a PCSK9 polypeptide to which an antibody specifically binds. A PCSK9 antigen also refers to an analog or derivative of a PCSK9 polypeptide or fragment thereof to which an antibody specifically binds. In some embodiments, a PCSK9 antigen is a monomeric PCSK9 antigen or a trimeric PCSK9 antigen. A region of a PCSK9 polypeptide contributing to an epitope may be contiguous amino acids of the polypeptide, or the epitope may come together from two or more non-contiguous regions of the polypeptide. The epitope may or may not be a three-dimensional surface feature of the antigen. A localized region on the surface of a PCSK9 antigen that is capable of eliciting an immune response is a PCSK9 epitope. The epitope may or may not be a three-dimensional surface feature of the antigen.

The term "human PCSK9," "hPCSK9" or "hPCSK9 polypeptide" and similar terms refer to the polypeptides ("polypeptides," "peptides" and "proteins" are used interchangeably herein) comprising the amino acid sequence of SEQ ID NO:198 and related polypeptides, including SNP variants thereof. Related polypeptides include allelic variants (e.g., SNP variants); splice variants; fragments; derivatives; substitution, deletion, and insertion variants; fusion polypeptides; and interspecies homologs, preferably, which retain PCSK9 activity and/or are sufficient to generate an anti-PCSK9 immune response. Also encompassed are soluble forms of PCSK9 that are sufficient to generate an anti-PCSK9 immunological response. As those skilled in the art will appreciate, an anti-PCSK9 antibody can bind to a PCSK9 polypeptide, polypeptide fragment, antigen, and/or epitope, as an epitope is part of the larger antigen, which is part of the larger polypeptide fragment, which, in turn, is part of the larger polypeptide. hPCSK9 can exist in a trimeric (native) or monomeric (denatured) form.

The terms "PCSK9-mediated disease," "PCSK9-mediated condition," and "PCSK9-mediated disorder" are used interchangeably and refer to any disease that is completely or partially caused by or is the result of PCSK9, e.g., hPCSK9. In certain embodiments, PCSK9 is aberrantly (e.g., highly) expressed. In some embodiments, PCSK9 may be aberrantly upregulated. In other embodiments, normal, aberrant, or excessive cell signaling is caused by binding of PCSK9 to a PCSK9 ligand. In certain embodiments, the PCSK9 ligand is a PCSK9 receptor. In certain embodiments, the PCSK9-mediated disease or condition is selected from the group consisting of: elevated total cholesterol levels; elevated low-density lipoprotein cholesterol (LDL-C) levels; hyperlipidemia; dyslipidemia; hypercholesterolemia, particularly hypercholesterolemia uncontrolled by statins, hypercholesterolemia, such as familial hypercholesterolemia or non-familial hypercholesterolemia, and hypercholesterolemia uncontrolled by statins; atherosclerosis; and cardiovascular diseases.

The terms "subject" and "patient" are used interchangeably. As used herein, a subject is preferably a mammal, such as a non-primate (e.g., cows, pigs, horses, cats, dogs, rats, etc.) or a primate (e.g., monkey and human), most preferably a human. In one embodiment, the subject is a mammal, preferably a human, having a PCSK9-mediated disease. In another embodiment, the subject is a mammal, preferably a human, at risk of developing a PCSK9-mediated disease.

The term "therapeutic agent" refers to any agent that can be used in the treatment, management or amelioration of a PCSK9-mediated disease and/or a symptom related thereto. In certain embodiments, the term "therapeutic agent" refers to a PCSK9 antibody of the invention. In certain other embodiments, the term "therapeutic agent" refers to an agent other than a PCSK9 antibody of the invention. Preferably, a therapeutic agent is an agent that is known to be useful for, or has been or is currently being used for the treatment, management or amelioration of a PCSK9-mediated disease or one or more symptoms related thereto.

The term "therapy" refers to any protocol, method, and/or agent that can be used in the prevention, management, treatment, and/or amelioration of a PCSK9-mediated disease (e.g., atherosclerosis or hypercholesterolemia). In certain embodiments, the terms "therapies" and "therapy" refer to a biological therapy, supportive therapy, and/or other therapies useful in the prevention, management, treatment, and/or amelioration of a PCSK9-mediated disease known to one of skill in the art, such as medical personnel.

The terms "treat", "treatment", and "treating" refer to the reduction or amelioration of the progression, severity, and/or duration of a PCSK9-mediated disease (e.g., atherosclerosis) resulting from the administration of one or more therapies (including, but not limited to, the administration of one or more prophylactic or therapeutic agents). In specific embodiments, such terms refer to the reduction or inhibition of the binding of PCSK9 to a PCSK9 ligand.

Although any methods and materials similar or equivalent to those described herein can be used in the practice of the present invention, the preferred methods and materials are now described. All publications mentioned herein are incorporated herein by reference to describe in their entirety.

Patient Populations

The methods of the present invention comprise selecting subjects that have, or are at risk of developing, a PCSK9-mediated disease or condition, such as hypercholesterolemia or a related disorder (e.g., atherosclerosis), and administering to these subjects, in the absence of a statin, a pharmaceutical composition comprising a PCSK9 inhibitor.

For example, the methods of the present invention comprise administering to a subject in need thereof a therapeutic composition comprising an anti-PCSK9 antibody, in the absence of a statin. The therapeutic composition can comprise any of the anti-PCSK9 antibodies, or fragments thereof, as disclosed herein.

As used herein, the expression "a subject in need thereof" means a human or non-human animal that exhibits one or more symptoms or indicia of hypercholesterolemia or who has been diagnosed with hypercholesterolemia, or who otherwise would benefit from a reduction in total serum cholesterol, LDL, triglycerides, VLDL, lipoprotein(a) [Lp (a)], or who would benefit from an increase in HDL. Specific exemplary populations treatable by the therapeutic methods of the invention include patients indicated for LDL apheresis, subjects with PCSK9-activating (GOF) mutations, patients with heterozygous or homozygous Familial Hypercholesterolemia (HeFH or HoFH); subjects with primary hypercholesterolemia who are statin intolerant or statin uncontrolled; and subjects at risk for developing hypercholesterolemia who may be preventably treated.

While modifications in lifestyle and conventional drug treatment are often successful in reducing cholesterol levels, not all patients are able to achieve the recommended target cholesterol levels with such approaches. Various conditions, such as familial hypercholesterolemia (FH), appear to be resistant to lowering of LDL-C levels in spite of aggressive use of conventional therapy. Homozygous and heterozygous familial hypercholesterolemia (hoFH, heFH) are conditions associated with premature atherosclerotic vascular disease. However, patients diagnosed with hoFH are largely unresponsive to conventional drug therapy and have limited treatment options. Specifically, treatment with statins, which reduce LDL-C by inhibiting cholesterol synthesis and upregulating the hepatic LDL receptor, may have little effect in patients whose LDL receptors are non-existent or defective. A mean LDL-C reduction of only less than about 20% has been recently reported in patients with genotype-confirmed hoFH treated with the maximal dose of statins. The addition of ezetimibe 10 mg/day to this regimen resulted in a total reduction of LDL-C levels of 27%, which is still far from optimal. Likewise, many patients are statin non-responsive, poorly controlled with statin therapy, or cannot tolerate statin therapy; in general, these patients are unable to achieve cholesterol control with alternative treatments. There is a large unmet medical need for new treatments that can address the short-comings of current treatment options.

Thus, the invention includes therapeutic methods in which a PCSK9 inhibitor of the invention is administered in the absence of a statin to a patient to treat or prevent hypercholesterolemia. As used herein, the use of the PCSK9 inhibitor "in the absence of a statin" means that the subject is not taking a concomitant statin while being treated with the PCSK9 inhibitor of the invention, or was not recently taking a statin prior to treatment with the PCSK9 inhibitor of the invention. The terms "in the absence of a statin" and "not on a concomitant statin" mean that the subject should have no detectable levels of statin the bloodstream, but, due to prior therapy, the subject may have a serum concentration of any statin of less than 0.1 mg/mL. As used herein, a "lipid lowering agent" means any pharmaceutical agent other than a PCSK9 inhibitor which is administered for the purpose of modifying the lipid profile of a subject. Examples of lipid-lowering agents include, but are not limited to: HMG-CoA reductase inhibitors, including statins (atorvastatin, cerivastatin, fluvastatin, lovastatin, mevastatin, pitavastatin, pravastatin, rosuvastatin, simvastatin, etc.), niacin, fibric acid, bile acid sequestrants (e.g., cholestyramine), colesevelam, colestipol, and ezetimibe. It follows that a "non-statin lipid lowering agent" means any pharmaceutical agent other than a PCSK9 inhibitor and a statin. Examples of non-statin lipid lowering agents include, but are not limited to, niacin, fibric acid, fenofibrate, bile acid sequestrants (e.g., cholestyramine), colesevelam, colestipol, an omega-3 fatty acid, a bile acid resin, and ezetimibe.

In some instances the patient who is treated with a therapeutic formulation of the present invention is otherwise healthy except for exhibiting elevated levels of cholesterol, lipids, triglycerides or lipoproteins. For example, the patient may not exhibit any other risk factor of cardiovascular, thrombotic or other diseases or disorders at the time of treatment. In other instances, however, the patient is selected on the basis of being diagnosed with, or at risk of developing, a disease or disorder that is caused by, correlated with or ancillary to elevated serum cholesterol, lipids, triglycerides or lipoproteins. For example, at the time of, or prior to administration of the pharmaceutical composition of the present invention, the patient may be diagnosed with or identified as being at risk of developing a cardiovascular disease or disorder, such as, e.g., coronary artery disease, acute myocardial infarction, asymptomatic carotid atherosclerosis, stroke, peripheral artery occlusive disease, etc. The cardiovascular disease or disorder, in some instances, is hypercholesterolemia. For example, a patient may be selected for treatment with a pharmaceutical composition of the present invention if the patient is diagnosed with or identified as being at risk of developing a hypercholesterolemia condition such as, e.g., heterozygous Familial Hypercholesterolemia (heFH), homozygous Familial Hypercholesterolemia (hoFH), as well as incidences of hypercholesterolemia that are distinct from Familial Hypercholesterolemia (nonFH).

In other instances, at the time of, or prior to administration of the pharmaceutical composition of the present invention, the patient may be diagnosed with or identified as being at risk of developing a thrombotic occlusive disease or disorder, such as, e.g., pulmonary embolism, central retinal vein occlusion, etc. In certain embodiments, the patient is selected on the basis of being diagnosed with or at risk of developing a combination of two or more of the above mentioned diseases or disorders. For example, at the time of, or prior to administration of the pharmaceutical composition of the present invention, the patient may be diagnosed with or identified as being at risk of developing coronary artery disease and pulmonary embolism. Other diagnostic combinations (e.g., atherosclerosis and central retinal vein occlusion, heFH and stroke, etc.) are also included in the definition of the patient populations that are treatable with a pharmaceutical composition of the present invention.

The pharmaceutical compositions of the present invention are also useful for treating hypercholesterolemia or dyslipidemia caused by or related to an underlying disease or disorder selected from the group consisting of metabolic syndrome, diabetes mellitus, hypothyroidism, nephrotic syndrome, renal failure, Cushing's syndrome, biliary cirrhosis, glycogen storage diseases, hepatoma, cholestasis, growth hormone deficiency. The pharmaceutical compositions of the present invention are also useful for treating hypercholesterolemia or dyslipidemia caused by or related to a prior therapeutic regimen such as estrogen therapy, progestin therapy, beta-blockers, or diuretics.

In yet other instances, the patient who is to be treated with a pharmaceutical composition of the present invention is selected on the basis of one or more factors selected from the group consisting of age (e.g., older than 40, 45, 50, 55, 60, 65, 70, 75, or 80 years), race, gender (male or female), exercise habits (e.g., regular exerciser, non-exerciser), other preexisting medical conditions (e.g., type-II diabetes, high blood pressure, etc.), and current medication status (e.g., currently taking statins [e.g., cerivastatin, atorvastatin, simvastatin, pitavastatin, rosuvastatin, fluvastatin, lovastatin, pravastatin, etc.], beta blockers, niacin, etc.). Potential patients can be selected/screened on the basis of one or more of these factors (e.g., by questionnaire, diagnostic evaluation, etc.) before being treated with the methods of the present invention.

The present invention also includes methods for increasing transintestinal cholesterol excretion (TICE) in a subject by administering a PCSK9 inhibitor to the subject. For example, the present invention provides methods for increasing TICE in a subject by administering to the subject an anti-PCSK9 antibody with pH-dependent binding characteristics. According to certain embodiments, the present invention includes methods comprising identifying a subject for which enhanced TICE would be beneficial, or identifying a subject that exhibits impaired TICE, and administering a PCSK9 inhibitor to the subject.

Hypercholesterolemia is a precursor to atherosclerosis. Accordingly, the invention also includes therapeutic methods in which a PCSK9 inhibitor of the invention is administered in the absence of a statin to a patient to treat or prevent atherosclerosis. Risk factors for atherosclerosis are well known in the art and include, without limitation, high low density lipoprotein (LDL) cholesterol levels, low high density lipoprotein (HDL) cholesterol levels, hypertension, diabetes mellitus, family history, male gender, cigarette smoking, and high serum cholesterol. Methods of assessing these risk factors for a given subject are also well known in the art.

In certain embodiments, the selected subject is hyperlipidemic. A "hyperlipidemic" is a subject that is a hypercholesterolemic and/or a hypertriglyceridemic subject. A "hypercholesterolemic" subject is one that fits the current criteria established for a hypercholesterolemic subject. A "hypertriglyceridemic" subject is one that fits the current criteria established for a hypertriglyceridemic subject (See, e.g., Harrison's Principles of Experimental Medicine, 13th Edition, McGraw-Hill, Inc., N.Y.). For example, a hypercholesterolemic subject typically has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject typically has a triglyceride (TG) level of >250 mg/dL. In certain embodiments the selected subject is hyperlipidemic but not receiving treatment for hyperlipidemia.

PCSK9 Inhibitors

The methods of the present invention comprise administering to a patient a therapeutic composition comprising a PCSK9 inhibitor. As used herein, a "PCSK9 inhibitor" is any agent which binds to or interacts with human PCSK9 and inhibits the normal biological function of PCSK9 in vitro or in vivo. Non-limiting examples of categories of PCSK9 inhibitors include small molecule PCSK9 antagonists, peptide-based PCSK9 antagonists (e.g., "peptibody" molecules), and antibodies or antigen-binding fragments of antibodies that specifically bind human PCSK9.

The term "human proprotein convertase subtilisin/kexin type 9" or "human PCSK9" or "hPCSK9" refers to PCSK9 having the nucleic acid sequence shown in SEQ ID NO:197 and the amino acid sequence of SEQ ID NO:198, or a biologically active fragment thereof.

The term "antigen binding protein" means a protein that binds to an antigen. For example, an antigen binding protein includes, but is not limited to, an antibody, an antigen binding fragment of an antibody, a DVD-Ig, and a dual variable domain immunoglobulin.

The term "antibody" is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," also includes antigen-binding fragments of full antibody molecules. The terms "antigen-binding portion" of an antibody, "antigen-binding fragment" of an antibody, and the like, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment".

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody" is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" is not intended to include antibodies in which CDR sequences derived from the germline of another mammalian species, such as a mouse, have been grafted onto human framework sequences.

The term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds" or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PCSK9, as used in the context of the present invention, includes antibodies that bind PCSK9 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PCSK9, however, have cross-reactivity to other antigens, such as PCSK9 molecules from other (non-human) species.

The anti-PCSK9 antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-PCSK9 antibodies comprising variants of any of the HCVR, LCVR, and/or CDR amino acid sequences disclosed herein having one or more conservative substitutions. For example, the present invention includes the use of anti-PCSK9 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$" is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain embodiments, the anti-PCSK9 antibody used in the methods of the present invention is an antibody with pH-dependent binding characteristics. As used herein, the expression "pH-dependent binding" means that the antibody or antigen-binding fragment thereof exhibits "reduced binding to PCSK9 at acidic pH as compared to neutral pH" (for purposes of the present disclosure, both expressions may be used interchangeably). For the example, antibodies "with pH-dependent binding characteristics" includes antibodies and antigen-binding fragments thereof that bind PCSK9 with higher affinity at neutral pH than at acidic pH. In certain embodiments, the antibodies and antigen-binding fragments of the present invention bind PCSK9 with at least 3, 5, 10, 15, 20, 25, 30, 35, 40, 45, 50, 55, 60, 65, 70, 75, 80, 85, 90, 95, 100, or more times higher affinity at neutral pH than at acidic pH.

According to this aspect of the invention, the anti-PCSK9 antibodies with pH-dependent binding characteristics may possess one or more amino acid variations relative to the parental anti-PCSK9 antibody. For example, an anti-PCSK9 antibody with pH-dependent binding characteristics may contain one or more histidine substitutions or insertions, e.g., in one or more CDRs of a parental anti-PCSK9 antibody. Thus, according to certain embodiments of the present invention, methods are provided comprising administering an anti-PCSK9 antibody which comprises CDR amino acid sequences (e.g., heavy and light chain CDRs) which are identical to the CDR amino acid sequences of a parental anti-PCSK9 antibody, except for the substitution of one or more amino acids of one or more CDRs of the parental antibody with a histidine residue. The anti-PCSK9 antibodies with pH-dependent binding may possess, e.g., 1, 2, 3, 4, 5, 6, 7, 8, 9, or more histidine substitutions, either within a single CDR of a parental antibody or distributed throughout multiple (e.g., 2, 3, 4, 5, or 6) CDRs of a parental anti-PCSK9 antibody. For example, the present invention includes the use of anti-PCSK9 antibodies with pH-dependent binding comprising one or more histidine substitutions in HCDR1, one or more histidine substitutions in HCDR2, one or more histidine substitutions in HCDR3, one or more histidine substitutions in LCDR1, one or more histidine substitutions in LCDR2, and/or one or more histidine substitutions in LCDR3, of a parental anti-PCSK9 antibody.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.90, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Preparation of Human Antibodies

Methods for generating human antibodies in transgenic mice are known in the art. Any such known methods can be used in the context of the present invention to make human antibodies that specifically bind to human PCSK9.

Using VELOCIMMUNE™ technology (see, for example, U.S. Pat. No. 6,596,541, Regeneron Pharmaceuticals) or any other known method for generating monoclonal antibodies, high affinity chimeric antibodies to PCSK9 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs:1 and 11, or a substantially similar sequence thereof having at least 90%, at least 95%, at least 98% or at least 99% sequence identity. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs:6 and 15, or a substantially similar sequence thereof having at least 90%, at least 95%, at least 98% or at least 99% sequence identity.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs: 1/6 and 11/15.

In certain embodiments of the present invention, the anti-PCSK9 antibody, or antigen-binding fragment thereof, that can be used in the methods of the present invention has HCDR1/HCDR2/HCDR3/LCDR1/LCDR2/LCDR3 amino acid sequences selected from SEQ ID NOs:2/3/4/7/8/10 (mAb316P) and SEQ ID NOs:12/13/14/16/17/18 (mAb300N) (See US Patent App. Publ No. 2010/0166768).

In certain embodiments of the present invention, the antibody or antigen-binding fragment thereof comprises HCVR/LCVR amino acid sequence pairs selected from the group consisting of SEQ ID NOs: 1/6 and 11/15.

Pharmaceutical Compositions and Methods of Administration

The present invention includes methods which comprise administering a PCSK9 inhibitor to a subject in the absence of a statin, wherein the PCSK9 inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to, AUTOPEN™ (Owen Mumford, Inc., Woodstock, UK), DISETRONIC™ pen (Disetronic Medical Systems, Bergdorf, Switzerland), HUMALOG MIX 75/25$^1$m pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to, the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain embodiments, the pharmaceutical composition is delivered in a controlled release system. In certain embodiments, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil], etc. As the oily medium, there are employed, e.g., sesame oil, soybean oil, etc., which may be used in combination with a solubilizing agent such as benzyl benzoate, benzyl alcohol, etc. In certain embodiments, the injection thus prepared is filled in an appropriate ampoule. In certain embodiments, the pharmaceutically acceptable excipient is a combination of histidine, pH 6.0, polysorbate 20, and sucrose.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage and Administration Regimens

The amount of PCSK9 inhibitor (e.g., anti-PCSK9 antibody) administered to a subject according to the methods and compositions of the present invention is, generally, a therapeutically effective amount. The phrase "therapeutically effective amount" means a dose of PCSK9 inhibitor that results in a detectable reduction in one more symptoms of hypercholesterolemia or a related disorder (e.g., lipid levels and/or atherosclerotic lesions).

The amount of anti-PCSK9 antibody contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight. Exemplary therapeutically effective amounts of antibody can be from about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PCSK9 antibody.

In certain embodiments, the anti-PCSK9 antibody is administered to a subject at a dose of about 150 mg every four weeks for at least three doses.

In some embodiments, the antibody is administered to a subject at a dose of about 150 mg every four weeks for 12 weeks, and the dose remains at 150 mg every four weeks for another 12 weeks if, at week 8, the subject's LDL-C value was less than 100 mg/dl and a 30% reduction of LDL-C.

In other embodiments, the antibody is administered to a subject at a dose of about 150 mg every four weeks for 12 weeks, and the dose is titrated up to about 150 mg every two weeks for another 12 weeks if, at week 8, the subject's LDL-C value was greater than or equal to 100 mg/dl.

In some embodiments, the antibody is administered to a subject at a dose of about 150 mg every four weeks for 12 weeks, and the dose remains at 150 mg every four weeks for another 12 weeks if, at week 8, the subject's LDL-C value was less than 70 mg/dl and a 30% reduction of LDL-C.

In another embodiment, the antibody is administered to a subject at a dose of about 300 mg every four weeks for 48 weeks.

In a further embodiment, the antibody is administered to a subject at a dose of about 300 mg every four weeks for a total of three doses, and the dose is changed to 150 mg every two weeks for another 36 weeks if, at week 8, the subject did not achieve a pre-determined treatment goal or the subject did not have at least a 30% reduction of LDL-C from baseline.

Additional Therapies

In some embodiments, the invention relates to a method for increasing the duration of action of a proprotein convertase subtilisin/kexin type 9 (PCSK9) antagonist in a subject comprising administering to the subject an anti-PCSK9 antagonist in the absence of a statin. In some embodiments, antagonist is an antibody or antigen binding protein. For example, the Examples show that administering an anti-PCSK9 antibody to a subject in the absence of a statin increases the duration of action of the anti-PCSK9 antibody.

In some embodiments, the invention relates to a method for maintaining constant low-density lipoprotein cholesterol (LDL-C) lowering throughout an interdosing interval in a subject comprising administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses. As shown in FIG. 1, prior art therapies exhibit a "sawtooth profile" of LDL-C during treatment. In contrast, the Q4W dosing regimen maintains constant LDL-C lowering throughout the interdosing interval in patients not receiving a statin.

In some embodiments, the invention relates to a method for reducing low-density lipoprotein cholesterol (LDL-C) in a subject in need thereof comprising administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses, thereby reducing the LDL-C in the subject.

In some embodiments, the invention relates to a method for treating hypercholesterolemia in a subject in need thereof comprising administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses, thereby treating the hypercholesterolemia in the subject.

In some embodiments, the invention relates to a method for treating a form of hypercholesterolemia that is not Familial Hypercholesterolemia in a subject in need thereof comprising administering to the subject a pharmaceutical composition comprising an anti-proprotein convertase subtilisin/kexin type 9 (anti-PCSK9) antibody or antigen-binding protein at a dose of about 150 mg every 4 weeks for at least 3 doses, thereby treating the form of hypercholesterolemia that is not Familial Hypercholesterolemia in the subject.

Thus, the methods of the present invention, according to certain embodiments, comprise administering a pharmaceutical composition comprising an anti-PCSK9 antibody to a subject, in the absence of a statin.

The methods of the present invention, according to certain embodiments, also comprise administering a pharmaceutical composition comprising an anti-CPSK9 inhibitor to a subject in combination with another non-statin lipid lowering agent.

Lipid lowering agents include, for example, agents which inhibit cholesterol uptake and or bile acid re-absorption (such as ezetimibe); agents which increase lipoprotein catabolism (such as niacin); and/or activators of the LXR transcription factor that plays a role in cholesterol elimination such as 22-hydroxycholesterol.

In some embodiments, the subject was previously on a therapeutic regimen for the treatment of hypercholesterolemia prior to administration of the pharmaceutical composition of the invention. For example, a patient who has previously been diagnosed with hypercholesterolemia may have been prescribed and was taking a stable therapeutic regimen of another drug prior to administration of a pharmaceutical composition comprising an anti-PCSK9 antibody.

In some embodiments, the subject was previously treated with a statin or other lipid lowering agent prior to treatment with a PCSK9 inhibitor described herein. In other embodiments, the subject has not been previously treated with a statin or other lipid lowering agent.

Exemplary Embodiments

In one aspect the present disclosure provides, a method for reducing low-density lipoprotein cholesterol (LDL-C) in a subject in need thereof, the method comprising administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses, thereby reducing the LDL-C in the subject.

In certain embodiments, the antibody or antigen-binding fragment thereof comprises the heavy and light chain complementarity determining regions (CDRs) of a heavy chain variable region/light chain variable region (HCVR/LCVR) amino acid sequence pair selected from the group consisting of SEQ ID NOs: 1/6 and 11/15. In certain embodiments, the antibody or antigen-binding fragment thereof comprises heavy and light chain CDR amino acid sequences having SEQ ID NOs:12, 13, 14, 16, 17, and 18. In certain embodiments, the antibody or antigen-binding fragment thereof comprises an HCVR having the amino acid sequence of SEQ ID NO:11 and an LCVR having the amino acid sequence of SEQ ID NO:15. In certain embodiments, the antibody or antigen-binding fragment thereof comprises heavy and light chain CDR amino acid sequences having SEQ ID NOs:2, 3, 4, 7, 8, and 10. In certain embodiments, the antibody or antigen-binding fragment thereof comprises an HCVR having the amino acid sequence of SEQ ID NO:1 and an LCVR having the amino acid sequence of SEQ ID NO:6.

In certain embodiments, the antibody or antigen-binding fragment thereof binds to the same epitope on PCSK9 as an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the antibody or antigen-binding fragment thereof competes for binding to PCSK9 with an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the subject has a form of hypercholesterolemia that is not Familial Hypercholesterolemia (nonFH). In certain embodiments, the subject has heterozygous Familial Hypercholesterolemia (heFH). In certain embodiments, the diagnosis of heFH is made either by genotyping or clinical criteria. In certain embodiments, the clinical criteria is either the Simon Broome Register Diagnostic Criteria for Heterozygous Familial Hypercholesterolemia, or the WHO/Dutch Lipid Network criteria with a score >8.

In certain embodiments, the subject is on a non-statin lipid-lowering agent before and/or during administration of the antibody or antigen-binding protein. In certain embodiments, the non-statin lipid-lowering agent is selected from the group consisting of: ezetimibe, a fibrate, fenofibrate, niacin, an omega-3 fatty acid, and a bile acid resin. In certain embodiments, the non-statin lipid-lowering agent is ezetimibe or fenofibrate.

In certain embodiments, the subject is not on a non-statin lipid-lowering agent before and/or during administration of the antibody or antigen-binding protein.

In certain embodiments, the antibody or antigen binding protein is administered subcutaneously.

In certain embodiments, the dose of about 150 mg every 4 weeks is maintained if the subject's LDL-C measured after 4 or more does is ≤70 mg/dL. In certain embodiments, the dose of about 150 mg every 4 weeks is discontinued if the subject's LDL-C measured after 4 or more doses is ≥70 mg/dL, and the antibody or antigen binding protein is subsequently administered to the subject at dose of about 150 mg every 2 weeks.

In another aspect the present disclosure provides, a method for treating hypercholesterolemia in a subject in need thereof, the method comprising administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses, thereby treating the hypercholesterolemia in the subject.

In certain embodiments, the antibody or antigen-binding fragment thereof comprises the heavy and light chain complementarity determining regions (CDRs) of a heavy chain variable region/light chain variable region (HCVR/LCVR) amino acid sequence pair selected from the group consisting of SEQ ID NOs: 1/6 and 11/15. In certain embodiments, the antibody or antigen-binding fragment thereof comprises heavy and light chain CDR amino acid sequences having SEQ ID NOs:12, 13, 14, 16, 17, and 18. In certain embodiments, the antibody or antigen-binding fragment thereof comprises an HCVR having the amino acid sequence of SEQ ID NO:11 and an LCVR having the amino acid sequence of SEQ ID NO:15. In certain embodiments, the antibody or antigen-binding fragment thereof comprises heavy and light chain CDR amino acid sequences having SEQ ID NOs:2, 3, 4, 7, 8, and 10. In certain embodiments, the antibody or antigen-binding fragment thereof comprises an HCVR having the amino acid sequence of SEQ ID NO:1 and an LCVR having the amino acid sequence of SEQ ID NO:6.

In certain embodiments, the antibody or antigen-binding fragment thereof binds to the same epitope on PCSK9 as an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the antibody or antigen-binding fragment thereof competes for binding to PCSK9 with an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the subject has a form of hypercholesterolemia that is not Familial Hypercholesterolemia (nonFH). In certain embodiments, the subject has heterozygous Familial Hypercholesterolemia (heFH). In certain embodiments, the diagnosis of heFH is made either by genotyping or clinical criteria. In certain embodiments, the clinical criteria is either the Simon Broome Register Diagnostic Criteria for Heterozygous Familial Hypercholesterolemia, or the WHO/Dutch Lipid Network criteria with a score >8.

In certain embodiments, the subject is on a non-statin lipid-lowering agent before and/or during administration of the antibody or antigen-binding protein. In certain embodiments, the non-statin lipid-lowering agent is selected from the group consisting of: ezetimibe, a fibrate, fenofibrate, niacin, an omega-3 fatty acid, and a bile acid resin. In certain embodiments, the non-statin lipid-lowering agent is ezetimibe or fenofibrate.

In certain embodiments, the subject is not on a non-statin lipid-lowering agent before and/or during administration of the antibody or antigen-binding protein.

In certain embodiments, the antibody or antigen binding protein is administered subcutaneously.

In certain embodiments, the dose of about 150 mg every 4 weeks is maintained if the subject's LDL-C measured after 4 or more does is ≤70 mg/dL. In certain embodiments, the dose of about 150 mg every 4 weeks is discontinued if the subject's LDL-C measured after 4 or more doses is ≥70 mg/dL, and the antibody or antigen binding protein is subsequently administered to the subject at dose of about 150 mg every 2 weeks.

In another aspect the present disclosure provides, a method for treating a form of hypercholesterolemia that is not Familial Hypercholesterolemia in a subject in need thereof, the method comprising administering to the subject a pharmaceutical composition comprising an anti-proprotein convertase subtilisin/kexin type 9 (anti-PCSK9) antibody or antigen-binding protein at a dose of about 150 mg every 4 weeks for at least 3 doses, thereby treating the form of hypercholesterolemia that is not Familial Hypercholesterolemia in the subject.

In certain embodiments, the antibody or antigen-binding fragment thereof comprises the heavy and light chain complementarity determining regions (CDRs) of a heavy chain variable region/light chain variable region (HCVR/LCVR) amino acid sequence pair selected from the group consisting of SEQ ID NOs: 1/6 and 11/15. In certain embodiments, the antibody or antigen-binding fragment thereof comprises heavy and light chain CDR amino acid sequences having SEQ ID NOs:12, 13, 14, 16, 17, and 18. In certain embodiments, the antibody or antigen-binding fragment thereof comprises an HCVR having the amino acid sequence of SEQ ID NO:11 and an LCVR having the amino acid sequence of SEQ ID NO:15. In certain embodiments, the antibody or antigen-binding fragment thereof comprises heavy and light chain CDR amino acid sequences having SEQ ID NOs:2, 3, 4, 7, 8, and 10. In certain embodiments, the antibody or antigen-binding fragment thereof comprises an HCVR having the amino acid sequence of SEQ ID NO:1 and an LCVR having the amino acid sequence of SEQ ID NO:6.

In certain embodiments, the antibody or antigen-binding fragment thereof binds to the same epitope on PCSK9 as an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the antibody or antigen-binding fragment thereof competes for binding to PCSK9 with an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the subject has a form of hypercholesterolemia that is not Familial Hypercholesterolemia (nonFH). In certain embodiments, the subject has heterozygous Familial Hypercholesterolemia (heFH). In certain embodiments, the diagnosis of heFH is made either by genotyping or clinical criteria. In certain embodiments, the clinical criteria is either the Simon Broome Register Diagnostic Criteria for Heterozygous Familial Hypercholesterolemia, or the WHO/Dutch Lipid Network criteria with a score >8.

In certain embodiments, the subject is on a non-statin lipid-lowering agent before and/or during administration of the antibody or antigen-binding protein. In certain embodiments, the non-statin lipid-lowering agent is selected from the group consisting of: ezetimibe, a fibrate, fenofibrate, niacin, an omega-3 fatty acid, and a bile acid resin. In certain embodiments, the non-statin lipid-lowering agent is ezetimibe or fenofibrate.

In certain embodiments, the subject is not on a non-statin lipid-lowering agent before and/or during administration of the antibody or antigen-binding protein.

In certain embodiments, the antibody or antigen binding protein is administered subcutaneously.

In certain embodiments, the dose of about 150 mg every 4 weeks is maintained if the subject's LDL-C measured after 4 or more does is ≤70 mg/dL. In certain embodiments, the dose of about 150 mg every 4 weeks is discontinued if the subject's LDL-C measured after 4 or more doses is ≥70 mg/dL, and the antibody or antigen binding protein is subsequently administered to the subject at dose of about 150 mg every 2 weeks.

In another aspect the present disclosure provides, a dosing regimen of an anti-proprotein convertase subtilisin/kexin type 9 (anti-PCSK9) antibody or antigen-binding protein that maintains a constant low-density lipoprotein cholesterol (LDL-C) lowering throughout the interdosing interval in a human subject which, following administration of the anti-PCSK9 antibody or antigen-binding protein thereof at a dose of about 150 mg every 4 weeks for at least 3 doses, has one or more of the properties selected from the group consisting of: (a) an area under the plasma concentration versus time curve calculated using the trapezoidal method from time zero to real time ($AUC_{last}$) from about 250 mg·day/L to about 650 mg·day/L; (b) a maximum plasma concentration observed ($C_{max}$) from about 15 mg/L to about 33 mg/L; (c) a first time to reach a maximum plasma concentration ($t_{max}$) of about 7 days; and (d) a time to reach terminal half life ($t_{1/2}^{Z}$) from about 5.5 days to about 12 days.

In another aspect the present disclosure provides, a dosing regimen of an anti-proprotein convertase subtilisin/kexin type 9 (anti-PCSK9) antibody or antigen-binding protein that maintains a constant low-density lipoprotein cholesterol (LDL-C) lowering throughout the interdosing interval in a human subject which, following administration of the anti-PCSK9 antibody or antigen-binding protein thereof at a dose of about 150 mg every 4 weeks for at least 3 doses, has one or more of the properties selected from the group consisting of: (a) an area under the plasma concentration versus time curve calculated using the trapezoidal method from time zero to real time ($AUC_{last}$) from about 150 mg·day/L to about 450 mg·day/L; (b) a maximum plasma concentration observed ($C_{max}$) from about 10.5 mg/L to about 24 mg/L; (c) a first time to reach a maximum plasma concentration ($t_{max}$) of about 7 days; and (d) a time to reach terminal half life ($t_{1/2}^{Z}$) from about 5 days to about 9 days.

In another aspect the present disclosure provides, a method for maintaining constant low-density lipoprotein cholesterol (LDL-C) lowering throughout an interdosing interval in a subject, the method comprising administering to the subject, who is not taking a concomitant statin, a pharmaceutical composition comprising an anti-proprotein convertase subtilisin/kexin type 9 (anti-PCSK9) antibody or antigen-binding protein at a dose of about 150 mg every 4 weeks for at least 3 doses.

In certain embodiments, the antibody or antigen-binding fragment thereof comprises the heavy and light chain complementarity determining regions (CDRs) of a heavy chain variable region/light chain variable region (HCVR/LCVR) amino acid sequence pair selected from the group consisting of SEQ ID NOs: 1/6 and 11/15. In certain embodiments, the antibody or antigen-binding fragment thereof comprises heavy and light chain CDR amino acid sequences having SEQ ID NOs:12, 13, 14, 16, 17, and 18. In certain embodiments, the antibody or antigen-binding fragment thereof comprises an HCVR having the amino acid sequence of SEQ ID NO:11 and an LCVR having the amino acid sequence of SEQ ID NO:15. In certain embodiments, the antibody or antigen-binding fragment thereof comprises heavy and light chain CDR amino acid sequences having SEQ ID NOs:2, 3, 4, 7, 8, and 10. In certain embodiments, the antibody or antigen-binding fragment thereof comprises an HCVR having the amino acid sequence of SEQ ID NO:1 and an LCVR having the amino acid sequence of SEQ ID NO:6.

In certain embodiments, the antibody or antigen-binding fragment thereof binds to the same epitope on PCSK9 as an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the antibody or antigen-binding fragment thereof competes for binding to PCSK9 with an antibody comprising heavy and light chain CDR amino acid sequences having SEQ ID NOs:12, 13, 14, 16, 17, and 18; or SEQ ID NOs: 2, 3, 4, 7, 8, and 10.

In certain embodiments, the subject has a form of hypercholesterolemia that is not Familial Hypercholesterolemia (nonFH). In certain embodiments, the subject has heterozygous Familial Hypercholesterolemia (heFH). In certain embodiments, the diagnosis of heFH is made either by genotyping or clinical criteria. In certain embodiments, the clinical criteria is either the Simon Broome Register Diagnostic Criteria for Heterozygous Familial Hypercholesterolemia, or the WHO/Dutch Lipid Network criteria with a score >8.

In certain embodiments, the subject is on a non-statin lipid-lowering agent before and/or during administration of the antibody or antigen-binding protein. In certain embodiments, the non-statin lipid-lowering agent is selected from the group consisting of: ezetimibe, a fibrate, fenofibrate, niacin, an omega-3 fatty acid, and a bile acid resin. In certain embodiments, the non-statin lipid-lowering agent is ezetimibe or fenofibrate.

In certain embodiments, the subject is not on a non-statin lipid-lowering agent before and/or during administration of the antibody or antigen-binding protein.

In certain embodiments, the antibody or antigen binding protein is administered subcutaneously.

In certain embodiments, the dose of about 150 mg every 4 weeks is maintained if the subject's LDL-C measured after 4 or more does is ≤70 mg/dL. In certain embodiments, the dose of about 150 mg every 4 weeks is discontinued if the subject's LDL-C measured after 4 or more doses is ≥70 mg/dL, and the antibody or antigen binding protein is subsequently administered to the subject at dose of about 150 mg every 2 weeks.

EXAMPLES

The following examples are put forth so as to provide those of ordinary skill in the art with a complete disclosure and description of how to make and use the methods and compositions of the invention, and are not intended to limit the scope of what the inventors regard as their invention.

Example 1: Generation of Human Antibodies to Human PCSK9

Human anti-PCSK9 antibodies were generated as described in U.S. Pat. No. 8,062,640. The exemplary PCSK9 inhibitor used in the following Examples is the human anti-PCSK9 antibody designated "alirocumab". Alirocumab has the following amino acid sequence characteristics: heavy chain variable region (HCVR) comprising SEQ ID NO:90; light chain variable domain (LCVR) comprising SEQ ID NO:92; heavy chain complementarity determining region 1 (HCDR1) comprising SEQ ID NO:76; HCDR2 comprising SEQ ID NO:78; HCDR3 comprising SEQ ID NO:80; light chain complementarity determining region 1 (LCDR1) comprising SEQ ID NO:84; LCDR2 comprising SEQ ID NO:86; and LCDR3 comprising SEQ ID NO:88.

Alirocumab is a fully human monoclonal antibody that binds proprotein convertase subtilisin kexin type 9 (PCSK9). Proprotein convertase subtilisin kexin type 9 belongs to the subtilisin family of serine proteases and is highly expressed in the liver. PCSK9 is involved in regulating the levels of the low-density lipoprotein receptor (LDLR) protein. In animals and humans, alirocumab reduces LDL-C levels in circulation. Alirocumab may be an effective treatment to lower LDL-C and to reduce the risk for cardiovascular disease.

Example 2: A Randomized, Partial Blind, 3 Parallel Groups Study of the Pharmacodynamic Profile of Alirocumab Administered as Multiple 150 mg Subcutaneous Doses, Either Alone or on Top of Ezetimibe or Fenofibrate Administered as Multiple Oral Doses in Healthy Subjects Introduction A phase 1 clinical trial was conducted to evaluate the pharmacodynamics and safety of an anti-PCSK9 antibody, alirocumab, in healthy subjects. The primary objective of the study was to assess the pharmacodynamic profile of alirocumab administered either alone or on top of ezetimibe or fenofibrate, based on low density lipoprotein cholesterol (LDL-C). The secondary objectives of the study were: 1) to assess the pharmacodynamic profile of alirocumab administered either alone or on top of ezetimibe or fenofibrate, based on other lipid parameters, 2) to assess the pharmacokinetic profile of alirocumab administered either alone or on top of ezetimibe or fenofibrate, 3) to document exposure to ezetimibe and fenofibrate, 4) to assess the effect of either ezetimibe or fenofibrate on PCSK9 levels, and 5) to assess the safety of concomitant administration of alirocumab and either ezetimibe or fenofibrate.

This phase 1 study was a randomized, partial blind, controlled study conducted in 3 parallel groups, with a 4-week run-in period with either ezetimibe or fenofibrate or placebo ezetimibe, followed by a 17 week treatment period (i.e.: group A: alirocumab+ezetimibe placebo, group B: alirocumab+ezetimibe, group C: alirocumab+fenofibrate). The study investigated the impact of combining 150 mg Q4W with ezetimibe (EZE) and fenofibrate (FENO) on the LDL-C lowering effect and on circulating levels of free PCSK9 and total alirocumab.

Subjects

The study evaluated 72 healthy subjects. The criteria for inclusion were: healthy male or female subjects, aged 18 to 65 years old, with serum LDL-C levels >130 mg/dL not receiving lipid lowering therapy at screening (Day −29), and serum LDL-C levels ≥100 mg/dL at the baseline control on Day −1 (before initiation of alirocumab). (Note: for practical reasons, the blood sample for the measure of baseline LDL-C was taken on D-1, to verify that subject had still a LDL-C level ≥100 mg/dL before initiating treatment with alirocumab).

Seventy-two subjects were randomized into three groups, with 24 subjects per group. Baseline characteristics for the subjects are shown in Table 1.

TABLE 1

| | Patient characteristics at baseline (Day-29) | | |
| --- | --- | --- | --- |
| Treatment group | Alirocumab 150 mg Q4W + placebo (N = 24) | Alirocumab 150 mg Q4W + EZE (N = 24) | Alirocumab 150 mg Q4W + FENO (N = 24) |
| Age (years), mean (SD) | 48.5 (12.8) | 49.5 (10.7) | 54.6 (7.6) |
| Male (%) | 46 | 46 | 42 |
| Body mass index (kg/m$^2$), mean (SD) | 23.9 (2.0) | 25.5 (2.7) | 24.7 (2.5) |
| Calculated LDL-C (mg/dL), mean (SD) | 183.3 (38.7) | 181.7 (37.1) | 180.6 (31.3) |
| Total cholesterol (mg/dL), mean (SD) | 264.5 (43.7) | 250.6 (40.6) | 263.7 (40.6) |

TABLE 1-continued

Patient characteristics at baseline (Day-29)

| Treatment group | Alirocumab 150 mg Q4W + placebo (N = 24) | Alirocumab 150 mg Q4W + EZE (N = 24) | Alirocumab 150 mg Q4W + FENO (N = 24) |
|---|---|---|---|
| Apolipoprotein B (g/L), mean (SD) | 1.3 (0.21) | 1.3 (0.22) | 1.3 (0.17) |
| Non-HDL-C (mg/dL), mean (SD) | 198.4 (40.6) | 200.3 (39.8) | 199.5 (31.7) |
| HDL-C (mg/dL), mean (SD) | 65.7 (12.4) | 60.3 (13.1) | 64.2 (15.5) |
| Triglycerides (mg/dL), median (range) | 78.8 (44.3-177.1) | 95.7 (35.4-168.3) | 94.8 (53.1-194.9) |
| Lipoprotein (a) (g/L), median (range) | 0.27 (0.0-1.6) | 0.33 (0.0-1.6) | 0.17 (0.0-1.5) |
| Free PCSK9 (ng/L), mean (SD) | 146.5 (54.3) | 150.7 (48.5) | 152.1 (54.1) |

HDL-C, high-density lipoprotein cholesterol;
SD, standard deviation

Study Treatments

Alirocumab was formulated as a 150 mg/ml solution for injection. Alirocumab was administered subcutaneously in the abdomen. Alirocumab was administered at a dose of 150 mg, 1 injection every four weeks, for a total of three injections.

Ezetimibe was formulated as a 10 mg over-encapsulated tablet (and matching placebo ezetimibe capsule). Ezetimibe was administered orally. Ezetimibe was administered at a dose of 10 mg, once daily administration for a total duration of 21 weeks (4 weeks run-in followed by 17 weeks after initial administration of alirocumab).

Fenofibrate was formulated at a 160 mg coated tablet. Fenofibrate was administered orally during a meal. Fenofibrate was administered at a dose of 160 mg, once daily administration for a total duration of 21 weeks (4 weeks of run-in followed by 17 weeks after initial administration of alirocumab).

The duration of treatment was as follows. Subjects received repeated doses (daily doses) of ezetimibe or fenofibrate or placebo ezetimibe for the duration of the run-in period (Days −28 to −1), and throughout the treatment phase (Days 1 to 120), and repeated doses of alirocumab (on Days 1, 29, and 57) on top of continuing ezetimibe or fenofibrate or placebo ezetimibe.

The duration of observation was up to a maximum of 25 weeks per subject (from screening to end-of-study [EOS] visit) which included a screening period of 3 weeks, a run-in period of 4 weeks, a treatment period of 17 weeks, and an EOS visit (a minimum of 4 days after the last dose with ezetimibe, placebo or fenofibrate).

Criteria for Evaluation

The pharmacodynamic criteria were as follows. The primary endpoint was percent change in calculated serum LDL-C from baseline (D-29). The secondary endpoints were absolute change from baseline in calculated LDL-C, total cholesterol (TC), high density lipoprotein cholesterol (HDL-C), non-HDL-C, triglycerides (TG), apolipoprotein B (ApoB), apolipoprotein A1 (ApoA1), and lipoprotein a (Lp[a]) analyzed in percent and absolute change from baseline.

The following pharmacokinetic (PK) parameters were calculated for alirocumab, using non-compartmental methods: maximum serum concentration observed ($C_{max}$), serum concentrations just before treatment administration during repeated dosing ($C_{trough}$), serum concentration observed at Day 29 ($C_{D29}$), area under the serum concentration versus time curve calculated using the trapezoidal method from time zero to the real time ($AUC_{last}$), area under the serum concentration versus time curve extrapolated to infinity (AUC), time to reach $C_{max}$ ($t_{max}$), area under the serum concentration versus time curve calculated using the trapezoidal method from time zero to Day 14 ($AUC_{0-D14}$), area under the serum concentration versus time curve calculated using the trapezoidal method from time zero to study Day 29 ($AUC_{0-D28}$), terminal half-life associated with the terminal slope ($t_{1/2z}$), time corresponding to the last concentration above the limit of quantification ($t_{last}$), apparent total body clearance of a drug from the serum (CL/F), distribution volume at the steady-state ($V_{ss/F}$), mean time a molecule remains in the body (MRT), and distribution volume in the terminal phase ($V_{z/F}$). Total serum alirocumab concentrations, total and free proprotein convertase subtilisin kexin type 9 (PCSK9) concentrations, and anti-alirocumab antibodies were measured.

Subjects were monitored for safety via adverse events (AEs; including local tolerability) spontaneously reported by the subjects or observed by the Investigator, clinical laboratory evaluations (biochemistry, hematology, coagulation, and urinalysis), vital sign assessments (heart rate, systolic blood pressure, and diastolic blood pressure), body weight, physical examination, 12-lead electrocardiogram (ECG) automatic on-site recordings, urine drug screen; alcohol breath or plasma test; β-human chorionic gonadotrophin levels in females; and immunogenicity (anti-alirocumab antibody titers) assessments.

Pharmacodynamic Sampling Times

The blood sampling for lipid parameters (ie, LDL-C, TC, HDL-C, non-HDL-C, TG, ApoB, ApoA1, Lp[a]) were performed in the morning, in the fasted condition (at least 10-hours fasted and refrained from smoking), before any drug intake.

Blood samples were collected at screening; Day −1 of the run-in phase; and Days 8, 15, 22, 29±1, 57±1, 64±1, 71±1, 78±1, 85±1, 99±2, and 120±3 of the treatment phase.

Pharmacokinetic Sampling Times and Bioanalytical Methods

Pharmacokinetic blood samples for assay of alirocumab and total and free PCSK9 were collected at Day −28 and Day −15±2 of the run-in phase (assay of total and free PCSK9 only); at Days 1, 8, 15, 22, 29, 57, 64, 71, 78, 85, 99, 120 of the treatment phase; and the EOS visit.

Pharmacokinetic blood samples for assay of total and unconjugated ezetimibe as well as fenofibric acid were collected at Day −28, Day −15, and Day −1 of the run-in phase; and Days 1, 29, 57, and 64 of the treatment phase.

Samples for the determination of anti-drug antibody (ADA) levels in serum were collected at Day −28 of the run-in phase; Days 29, 57, 85, and 120 of the treatment phase; and the EOS visit.

Serum concentrations of alirocumab were determined using a validated enzyme-linked immunosorbent assay (ELISA) method with a lower limit of quantification (LLOQ) of 0.078 µg/mL.

Plasma concentrations of total and unconjugated ezetimibe, and fenofibric acid were determined using validated liquid chromatography with tandem mass spectrometry (LC-MS/MS) methods with lower limits of quantification of 0.2 ng/mL, 0.04 ng/mL, and 49.9 ng/mL, respectively.

Anti-alirocumab antibody samples were analyzed using a validated electrochemiluminescence assay for the determination of anti-alirocumab antibody titers in acid-treated human serum. Based on the minimum dilution of the samples, the minimum titer for any anti-alirocumab antibody positive sample was 30. In neat serum samples, the validated lower limit of detection was approximately 1.5 ng/mL.

Summary

Population Characterisitics

The study population included 72 subjects (24 in each treatment group); there were 32 male and 40 female subjects aged between 21 and 65 years.

Pharmacodynamic Results

Figure 2:
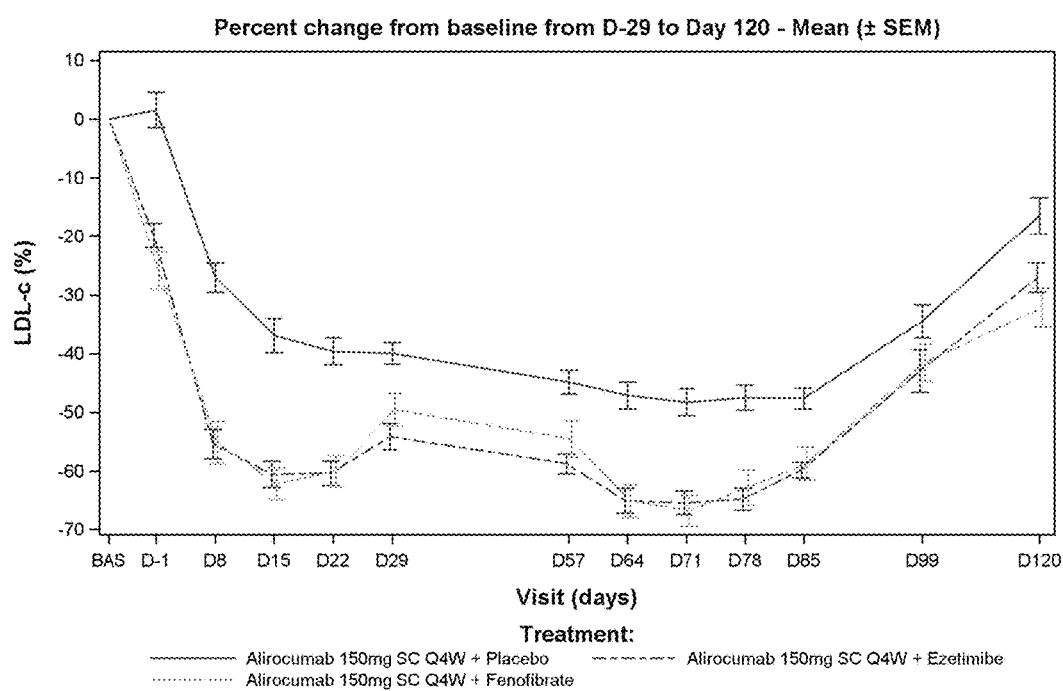
FIG. 2 is a graph showing the percent change of LDL-C from baseline from Day −29 to Day 120 for the three groups: alirocumab+placebo, alirocumab+ezetimibe, and alirocumab+fenofibrate.
Figure 3:
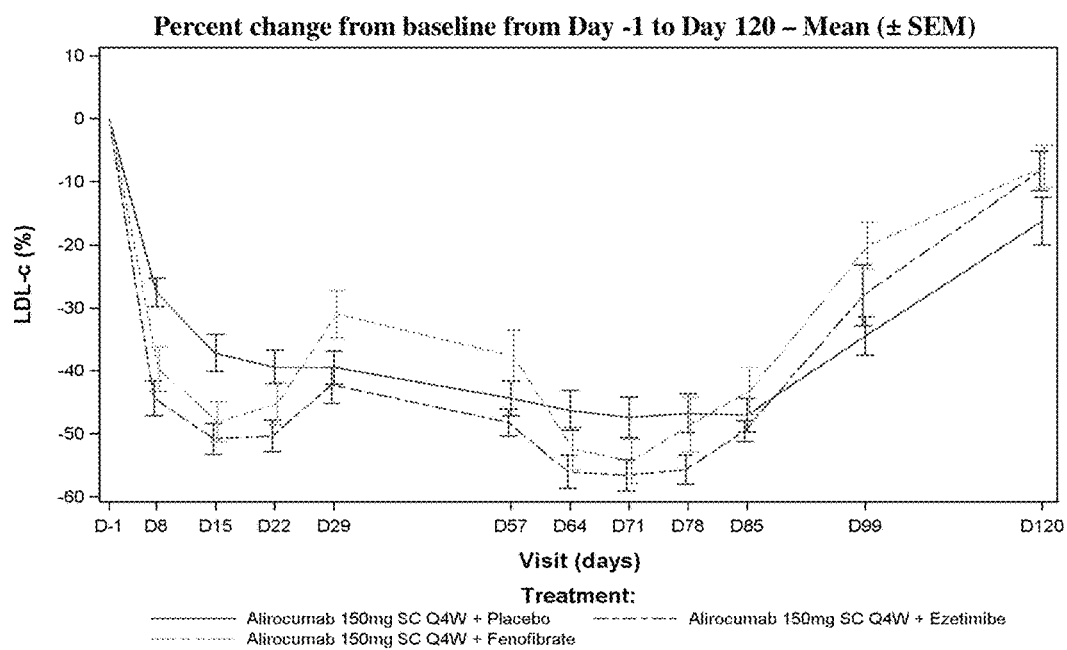
FIG. 3 is a graph showing the percent change of LDL-C from baseline from Day −1 to Day 120 for the three groups: alirocumab+placebo, alirocumab+ezetimibe, and alirocumab+fenofibrate.

LDL-C declined similarly in the ezetimibe and fenofibrate groups during the run-in period (Day −29 to Day −1) reaching −19.8 (2.1)% and −25.9 (3.2)%, in the ezetimibe and fenofibrate groups respectively on Day −1 and remained stable in the placebo group (+1.6 (3.0)% on Day −1) (FIG. 2). After the run-in period, treatment with alirocumab administered from Day 1, produced a further decline, greater in the ezetimibe and fenofibrate groups. The relative change in LDL-C was parallel in the 3 treatment groups until Day 15, then from Day 15 a modest reincrease was starting in the fenofibrate group while this was more stable until Day 22 in the ezetimibe group from which a slight reincrease was also seen. This trend was not observed in the alirocumab alone group in which the decline in LDL-C was sustained. The 3rd administration of alirocumab produced a further decline in LDL-C, compared to the decline observed after the 1st dose, and a maximum effect was achieved after the 3rd administration of alirocumab on Day 71 (14 days after administration) in all treatment groups ($p<0.0001$), whatever the baseline considered (Day −29 or Day −1), and with a similar behavior to that seen 21 days after the $1^{st}$ administration in the ezetimibe and fenofibrate groups (FIGS. 2 & 3; Table 2). Maximum decreases were −47.59%, −65.34% and −66.75% in the alirocumab alone, ezetimibe and fenofibrate groups, respectively (change from Day −29 baseline). Using the change from Day −1 baseline, maximum decreases were −47.39%, —56.56% and −54.34% in the alirocumab alone, ezetimibe and fenofibrate groups, respectively. On Day 28 after the $3^{rd}$ administration of alirocumab (ie: Day 85), decreases were −47.03%, −49.57% and −43.17% for alirocumab administered either alone, or with ezetimibe or with fenofibrate respectively (change from Day −1 baseline). See FIGS. 2 and 3.

Overall treatment effect was significant ($p<0.0001$). Pairwise comparisons showed that the difference between alirocumab alone and alirocumab coadministered with ezetimibe remained significant across all time points (FIG. 2). The difference between alirocumab alone and alirocumab coadministered with fenofibrate remained also significant across all time points, except on Day 99 (CI: −13.8174 to 0.1219%).

Figure 4:
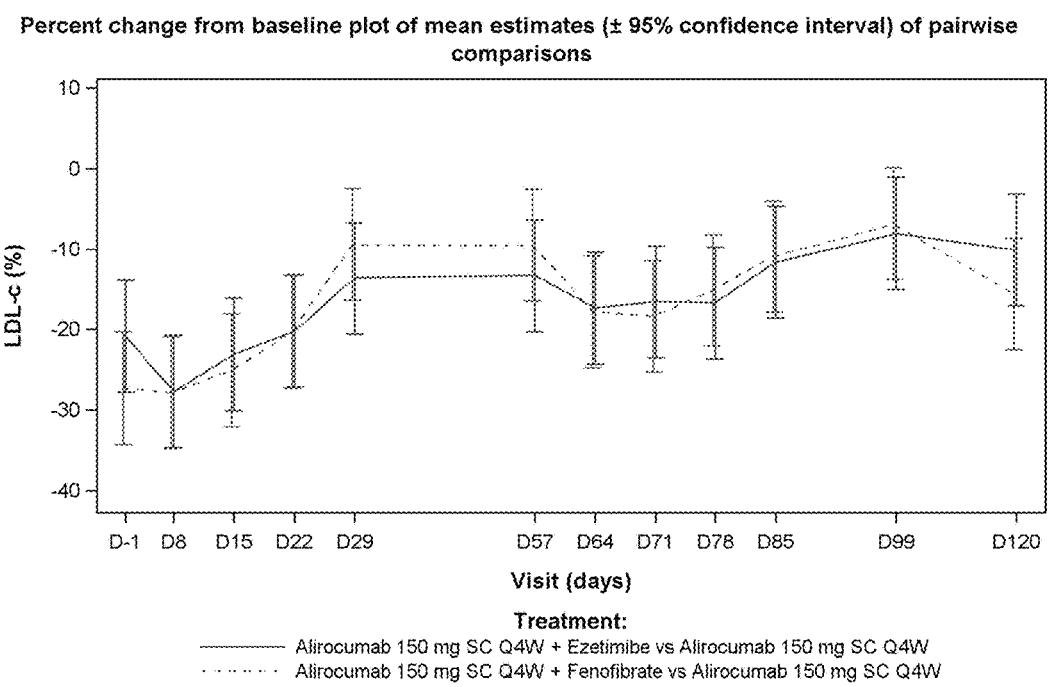
FIG. 4 is a graph showing the percent change of LDL-C from baseline plot of mean estimates of pairwise comparisons for: alirocumab 150 mg SC Q4W+ezetimibe v. alirocumab 150 mg SC Q4W; and alirocumab 150 mg SC Q4W+fenofibrate v. alirocumab 150 mg SC Q4W.

As shown in FIG. 4, analysis of the difference between mean estimates of alirocumab coadministered with ezetimibe versus alirocumab alone and alirocumab coadministered with fenofibrate versus alirocumab alone do not show any difference over the time course of the study between the fenofibrate and the ezetimibe groups. Relative changes in TC were parallel to the change in LDL-C. Treatment effect were significant for both TG and HDL-C. Compared to alirocumab alone, fenofibrate produced an increase in HDL-C and a decrease in TG, that were sustained and significant over most time points, whereas compared to alirocumab alone changes in the ezetimibe group were generally not significant.

Effects on other lipid parameters are summarized in Table 2. Table 2 shows that: 1) mean percentage (SEM) reductions from the main Day −29 baseline to Day 71 were −48.2 (2.3)% with alirocumab alone, and −65.3 (2.0)% and −66.8 (2.7)% with alirocumab+EZE and +FENO, respectively; and 2) mean percentage (SEM) LDL-C reductions from the Day −1 baseline to Day 71 were −47.4 (3.2)% with alirocumab alone, and −56.6 (2.5)% and −54.3 (3.5)% with alirocumab+EZE and +FENO, respectively.

TABLE 2

Mean (SEM) percent change in other lipid parameters from the Day −29 baseline and Day −1 baseline to Day 71 (14 days after the $3^{rd}$ alirocumab dose)

| Treatment group | Main baseline (Day −29) (From start of placebo, EZE or FENO run-in period) | | | Additional baseline (Day −1) (From start of alirocumab injection; placebo/EZE/FENO treatment continued) | | |
|---|---|---|---|---|---|---|
| | Alirocumab 150 mg Q4W + placebo (N = 24) | Alirocumab 150 mg Q4W + EZE (N = 24) | Alirocumab 150 mg Q4W + FENO (N = 24) | Alirocumab 150 mg Q4W + placebo (N = 24) | Alirocumab 150 mg Q4W + EZE (N = 24) | Alirocumab 150 mg Q4W + FENO (N = 24) |
| LDL-C | −48.2 (2.3) | −65.3 (2.0) | −66.8 (2.7) | −47.4 (3.2) | −56.6 (2.5) | −54.3 (3.5) |
| Total cholesterol | −31.6 (1.4) | −45.7 (1.5) | −46.1 (1.9) | −31.5 (2.6) | −36.5 (1.4) | −32.4 (2.2) |
| Non-HDL-C | −43.0 (1.7) | −60.6 (1.9) | −64.4 (2.5) | −43.0 (2.7) | −51.9 (2.1) | −50.5 (3.2) |
| Apolipoprotein B | −39.1 (1.5) | −53.5 (1.8) | −58.3 (2.1) | −38.4 (2.4) | −44.9 (2.0) | −44.6 (2.5) |
| HDL-C | 3.3 (3.4) | 5.4 (3.2) | 12.3 (3.1) | 3.6 (2.9) | 6.4 (3.1) | 8.7 (3.0) |

TABLE 2-continued

Mean (SEM) percent change in other lipid parameters from the Day −29
baseline and Day −1 baseline to Day 71 (14 days after the 3rd alirocumab dose)

| | Main baseline (Day −29) (From start of placebo, EZE or FENO run-in period) | | | Additional baseline (Day −1) (From start of alirocumab injection; placebo/EZE/FENO treatment continued) | | |
|---|---|---|---|---|---|---|
| Treatment group | Alirocumab 150 mg Q4W + placebo (N = 24) | Alirocumab 150 mg Q4W + EZE (N = 24) | Alirocumab 150 mg Q4W + FENO (N = 24) | Alirocumab 150 mg Q4W + placebo (N = 24) | Alirocumab 150 mg Q4W + EZE (N = 24) | Alirocumab 150 mg Q4W + FENO (N = 24) |
| Triglycerides* | 5.7 (−48.5 to 266.7) | −13.8 (−53.4 to 53.5) | −36.0 (−57.9 to 11.3) | −3.9 (−41.3 to 77.6) | −16.5 (−37.2 to 24.2) | −3.5 (−58.0 to 74.1) |
| Lipoprotein (a)* | −20.3 (−63.2 to 33.3) | −27.0 (−71.4 to 35.8) | −19.9 (−57.6 to 38.3) | −11.7 (−58.8 to 160.9) | −9.2 (−67.0 to 66.7) | −20.4 (−56.8 to 17.7) |

*Median (range)

FIGS. 5(A-D) are a group of four graphs that show the mean levels of free PCSK9, comparing the three treatment groups together, and compared with percent changes in LDL-C from the Day −29 baseline, per treatment group.

Figure 6A:
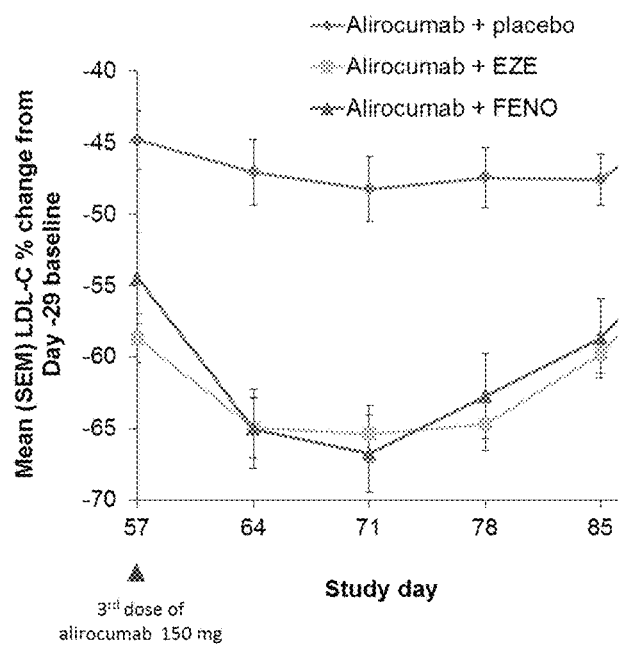
FIGS. 6A-C are a group of three graphs showing the percent changes in LDL-C from the Day −29 baseline (FIG. 6A), and levels of free PCSK9 (FIG. 6B) and total alirocumab (FIG. 6C) from Day 57 (time of $3^{rd}$ alirocumab injection) to Day 85 (28 days after $3^{rd}$ alirocumab injection).
Figure 6B:
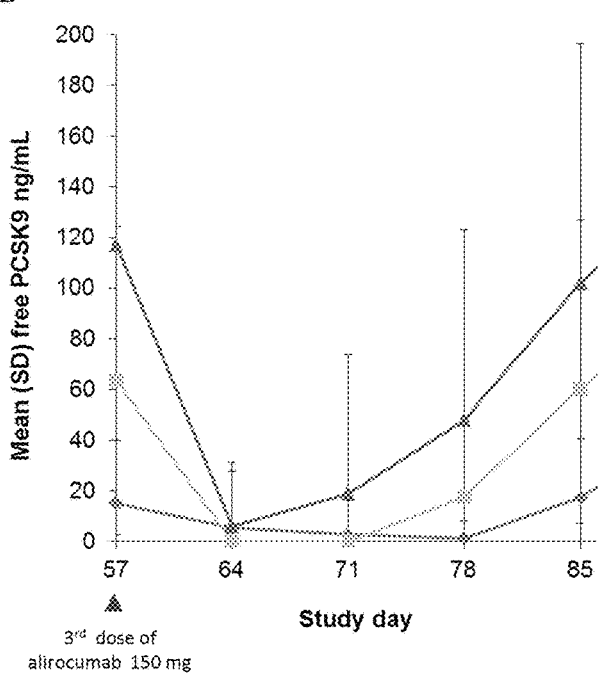

FIGS. 6(A-C) are a group of three graphs that show percent changes in LDL-C from the Day −29 baseline, levels of free PCSK9, and total alirocumab from Day 57 (time of 3rd alirocumab injection) to Day 85 (28 days after 3rd alirocumab injection).

During the placebo run-in period (i.e., prior to alirocumab treatment), FENO resulted in increased free PCSK9 levels from 152 to 217 ng/mL. Corresponding changes in free PCSK9 were 147 to 119 ng/mL in the placebo group and 151 to 142 ng/mL in the EZE group (FIG. 5A).

Figure 5A:
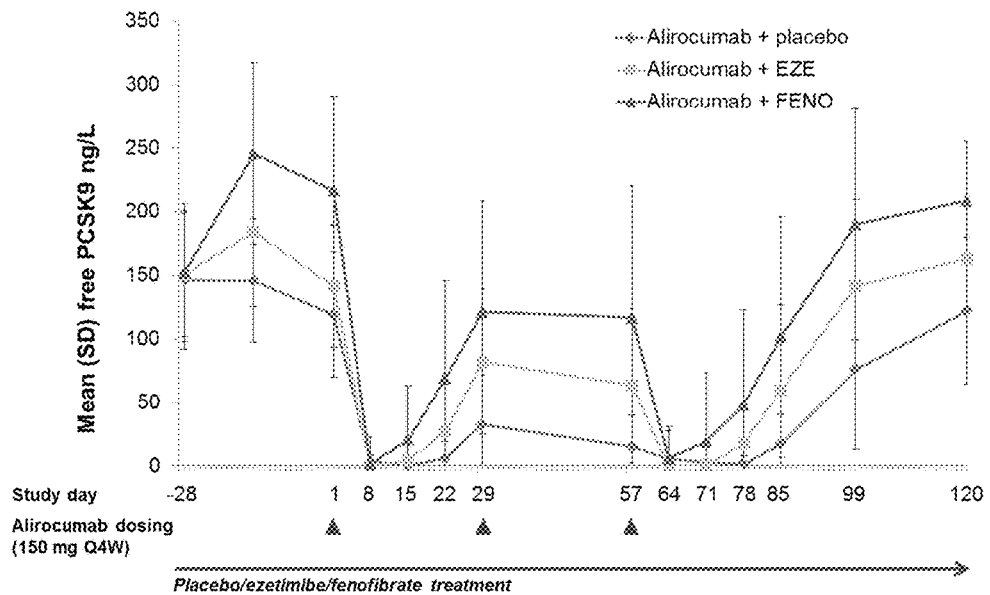
FIGS. 5A-D are a group of four graphs showing mean levels of free PCSK9, comparing the three treatment groups together (FIG. 5A) and compared with percent changes in LDL-C from the Day −29 baseline, per treatment group (FIGS. 5B-D) (N=24 per group).
Figure 5B:
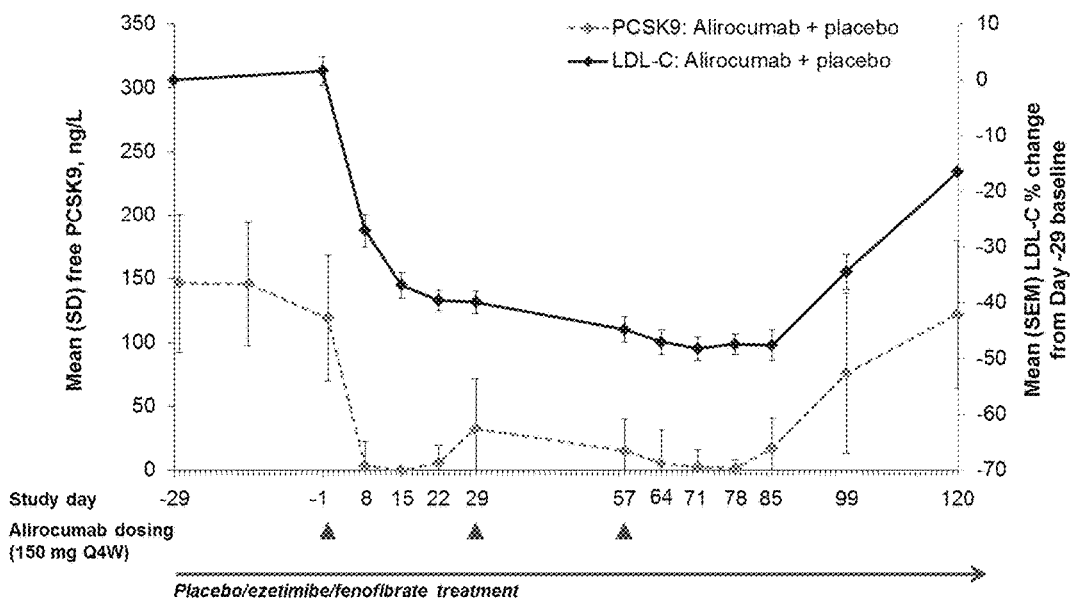
Figure 5C:
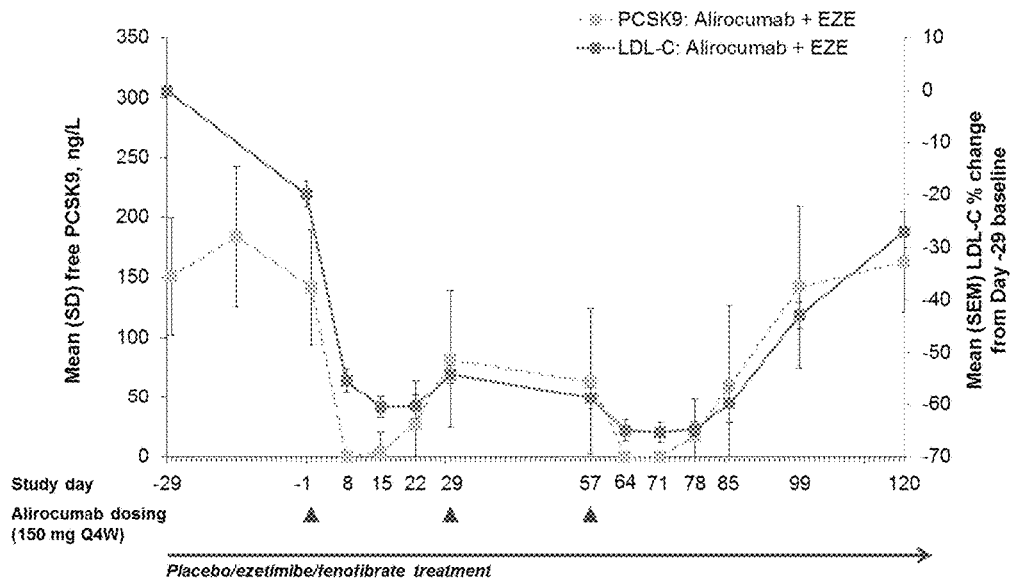
Figure 5D:
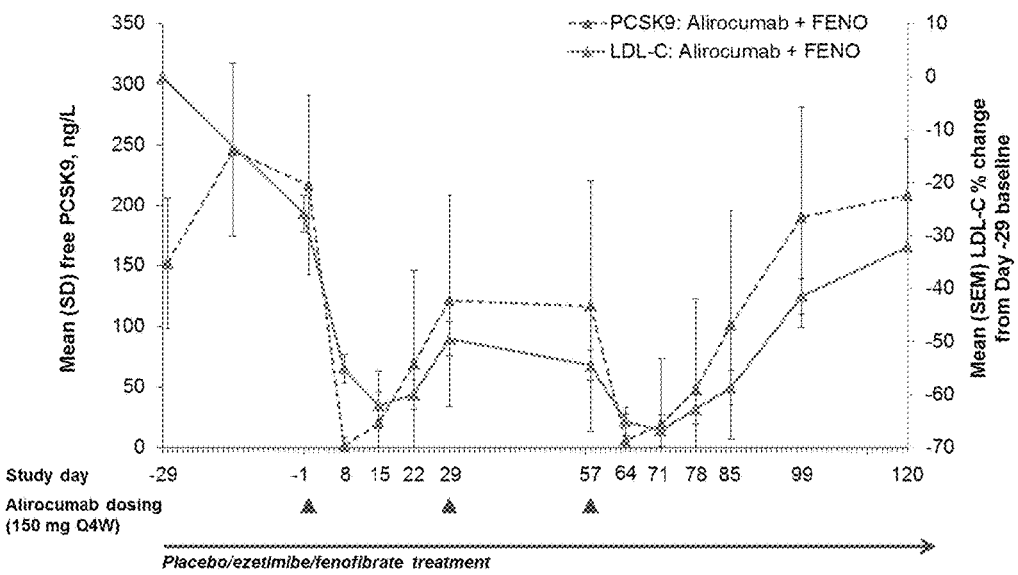

A complete suppression of free PCSK9 followed the 1st and 3rd alirocumab injections (no measure was done after the 2nd injection) (FIG. 5A).

After 7 to 15 days post-alirocumab injection, levels of free PCSK9 had increased again in the FENO group, and, to a lesser extent, in the EZE group, compared with the alirocumab alone group (FIG. 5A). These increases corresponded with the modest decrease in efficacy observed in the EZE and FENO groups (FIG. 5B-D; and close-up in FIGS. 6A+B).

Figure 6C:
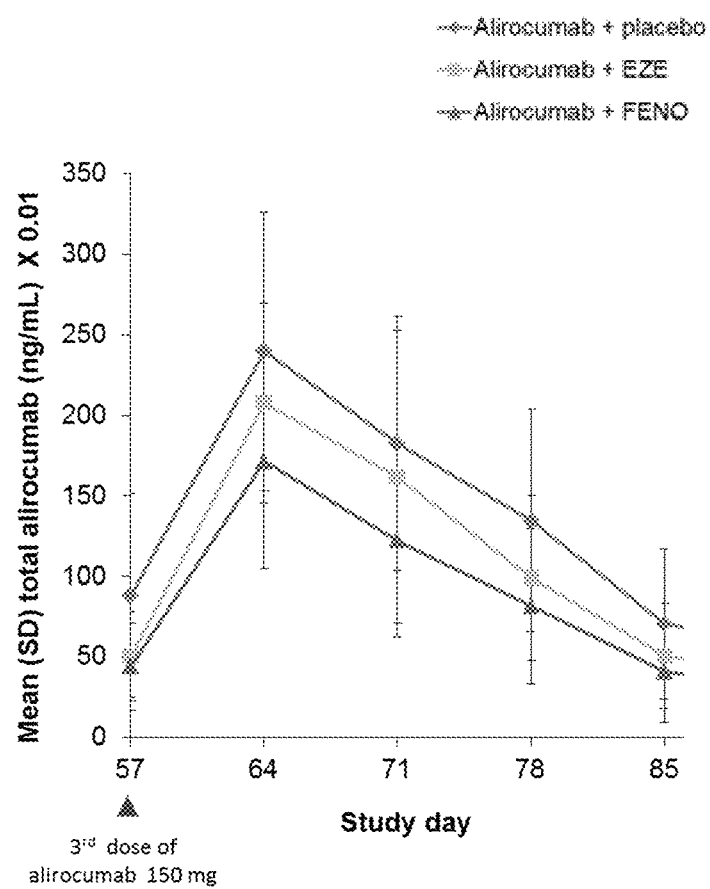

Corresponding to the changes in free PCSK9, alirocumab exposures were reduced in the presence of FENO (geometric mean ratio [95% confidence interval] versus alirocumab alone: 0.64 [0.53 to 0.77]) as well as in the presence of EZE (0.85 [0.70 to 1.03] versus alirocumab alone) (FIG. 6C).

Safety Results

There was no death or SAE during the study. The incidence of TEAEs was similar across the 3 treatment groups (50.0%, 58.3% and 50.0% in the alirocumab alone, ezetimibe and fenofibrate groups respectively). Only 1 subject had a TEAE of severe intensity, recorded in the fenofibrate group (renal colic, lasting about 11 hours, occurring 64 days after the last administration of alirocumab, and considered not related to the treatment). The most frequent TEAEs (ie. recorded in ≥2 subjects in any treatment group) were headache (3/24, 5/24, and 2/24 subjects in the alirocumab alone, ezetimibe and fenofibrate groups respectively), nasopharyngitis (3/24, 4/24, and 4/24 subjects in the alirocumab alone, ezetimibe and fenofibrate groups respectively), influenza (2/24, 0/24, and 1/24 subjects in the alirocumab alone, ezetimibe and fenofibrate groups respectively), gastroenteritis viral (0/24, 0/24, and 2/24 subjects in the alirocumab alone, ezetimibe and fenofibrate groups respectively), influenza-like illness (1/24, 3/24, and 1/24 subjects in the alirocumab alone, ezetimibe and fenofibrate groups respectively), and abdominal pain (2/24, 1/24, and 1/24 subjects in the alirocumab alone, ezetimibe and fenofibrate groups respectively). All other TEAEs were sporadic among the 3 groups.

There were few PCSAs in vital signs, with low incidence in the 3 treatment groups. There were few PCSAs in ECG parameters, however no QTc>450 ms (male) or QTc>470 ms (female) was recorded and no prolongation of QTc (defined as increase from baseline >60 ms) was detected. None of these abnormalities in vital signs or ECG parameters were considered clinically significant.

There were few PCSAs in hematology and biochemistry parameters with low incidence in the 3 treatment groups. None of these abnormalities were considered clinically significant, except for creatinine protein kinase (CPK) increase >10 upper limit of normal (ULN) in 1 subject of the alirocumab alone group. This CPK increase recorded at the EOS visit was considered related to physical exercise, and declared as an AE. There were no PCSAs in liver function tests.

There were no serious adverse events (AEs) or discontinuations due to AEs. Treatment-emergent adverse events (TEAEs) are summarized in Table 3.

One subject in the alirocumab+FENO group had a TEAE of severe intensity (renal colic), which was not considered by the investigator to be related to the study treatment.

No clinically significant changes in vital signs, electrocardiogram, hematologic or biochemical parameters were observed in this study. One subject in the alirocumab+placebo group displayed an increase in creatine phosphokinase >10 times the upper limit of normal, which was considered by the Investigator to be related to physical exercise (Table 3).

TABLE 3

Safety summary

| Treatment group | Alirocumab 150 mg Q4W + placebo (N = 24) | Alirocumab 150 mg Q4W + EZE (N = 24) | Alirocumab 150 mg Q4W + FENO (N = 24) |
|---|---|---|---|
| Patients with any TEAEs, n (%) | 12 (50.0) | 14 (58.3) | 12 (50.0) |
| Most frequent TEAEs (recorded in ≥2 subjects in any group), n (%) | | | |
| Headache | 3 (12.5) | 5 (20.8) | 2 (8.3) |
| Nasopharyngitis | 3 (12.5) | 4 (16.7) | 4 (16.7) |

TABLE 3-continued

Safety summary

| Treatment group | Alirocumab 150 mg Q4W + placebo (N = 24) | Alirocumab 150 mg Q4W + EZE (N = 24) | Alirocumab 150 mg Q4W + FENO (N = 24) |
|---|---|---|---|
| Influenza | 2 (8.3) | 0 (0) | 1 (4.2) |
| Gastroenteritis viral | 0 (0) | 0 (0) | 2 (8.3) |
| Influenza-like illness | 1 (4.2) | 3 (12.5) | 1 (4.2) |
| Abdominal pain | 2 (8.3) | 1 (4.2) | 1 (4.2) |

Immunogenicity Results

Four out of 24 subjects (16.7%) in the alirocumab alone group, 6/24 subjects (25%) in the ezetimibe group, and 7/24 (29.2%) subjects in the fenofibrate group were tested ADA positive with titers ranging between 30 (minimum detectable titer) and 240. A single titer of 240 was detected in a subject in the ezetimibe group on Day 29, declining to a titer of 30 on Day 85. On Day 120, no ADA's were detectable in this subject. All other measured ADA titers were low and between 30 and 120 for all other ADA positive subjects.

Over all groups, 4 subjects showed ADA positive titers in the predose samples. This suggests that these subjects exhibited a pretreatment immunoreactivity in the assay, and not necessarily a treatment-emergent ADA response to the administration of study drug. Only 1 pretreatment positive subject (fenofibrate group) had increased titers in postbaseline period, with a maximum titer of 120 on Day 29 and Day 120.

Pharmacokinetic (PK) Results

Figure 7:
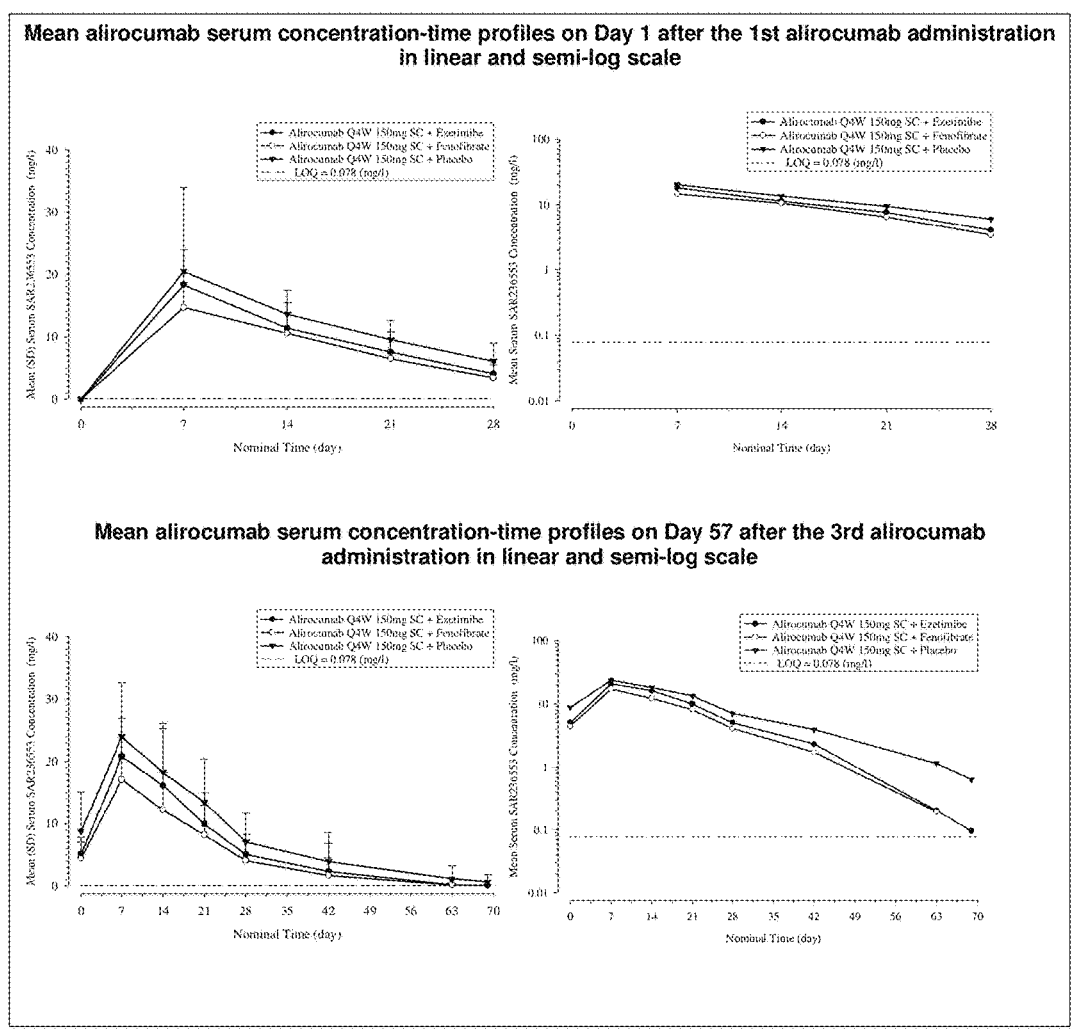
FIG. 7 (top) are two graphs showing the mean alirocumab serum concentration-time profiles on Day 1 after the first alirocumab administration in linear (top left) and semi-log scale (top right) for the three groups: alirocumab+placebo, alirocumab+ezetimibe, and alirocumab+fenofibrate.

Descriptive statistics of PK parameters of alirocumab following Q4W repeated SC doses of 150 mg alirocumab are provided in the tables below (Tables 4-6) and in FIG. 7.

TABLE 4

Mean ± SD (Geometric Mean) [CV %] of alirocumab PK parameters in serum on Day 1

| | Mean ± SD (Geometric Mean) [CV %] Serum Alirocumab | | |
|---|---|---|---|
| | Alirocumab Q4W 150 mg SC + Placebo | Alirocumab Q4W 150 mg SC + Fenofibrate | Alirocumab Q4W 150 mg SC + Ezetimibe |
| N | 24 | 24 | 24 |
| $C_{max}$ (mg/l) | 20.4 ± 13.5 (18.3) [66.2] | 14.6 ± 4.06 (14.1) [27.7] | 18.2 ± 5.68 (17.3) [31.2] |
| $C_{D29}$* (mg/l) | 6.06 ± 2.91 (5.45) [48.0] | 3.40 ± 2.05 (2.73) [60.4] | 4.04 ± 2.25 (3.49) [55.6] |
| $t_{max}^{a}$ (day) | 7.00 (6.96-7.01) | 7.00 (6.97-7.01) | 7.00 (6.97-7.19) |
| $AUC_{last}$ (mg · day/l) | 326 ± 125 (306) [38.4] | 233 ± 75.5 (221) [32.3] | 274 ± 87.4 (261) [31.8] |

TABLE 4-continued

Mean ± SD (Geometric Mean) [CV %] of alirocumab PK parameters in serum on Day 1

| | Mean ± SD (Geometric Mean) [CV %] Serum Alirocumab | | |
|---|---|---|---|
| | Alirocumab Q4W 150 mg SC + Placebo | Alirocumab Q4W 150 mg SC + Fenofibrate | Alirocumab Q4W 150 mg SC + Ezetimibe |
| N | 24 | 24 | 24 |
| $AUC_{0-D28}$** (mg · day/l) | 326 ± 125 (306) [38.4] | 233 ± 75.5 (221) [32.3] | 274 ± 87.4 (261) [31.8] |
| AUC (mg · day/l) | 357 ± 210 (318) [58.9]$^b$ | 241 ± 84.6 (227) [35.0]$^c$ | 291 ± 92.9 (277) [31.9]$^c$ |
| $AUC_{Ext}$*** (%) | 25 ± 11 (22) [44.7] | 15 ± 9 (12) [57.6] | 17 ± 11 (15) [62.6] |

$^a$Median(Min-Max)
$^b$n = 8,
$^c$n = 18,
*Concentration in serum on study day 29 (28 days after administration)
**Partial AUC calculated between study days 1 and 29 (PK time zero to Day 28)
***percentage of extrapolation of AUC

TABLE 5

Mean ± SD (Geometric Mean) [CV %] of alirocumab PK parameters in serum on Day 57, after the 3$^{rd}$ alirocumab administration

| | Mean ± SD (Geometric Mean) [CV%] Serum Alirocumab | | |
|---|---|---|---|
| | Alirocumab Q4W 150 mg SC + Placebo | Alirocumab Q4W 150 mg SC + Fenofibrate | Alirocumab Q4W 150 mg SC + Ezetimibe |
| N | 24 | 24 | 24 |
| $C_{max}$ (mg/l) | 24.3 ± 8.61 (22.9) [35.5] | 17.1 ± 6.66 (15.9) [38.9] | 21.9 ± 8.91 (20.5) [40.6] |
| $C_{D29}$* (mg/l) | 7.07 ± 4.66 (6.00) [66.0] | 4.08 ± 3.18 (2.89) [77.9] | 5.08 ± 3.26 (4.02) [64.3] |
| $t_{max}^{a}$ (day) | 7.00 (0.00-7.00) | 7.00 (6.97-7.99) | 7.00 (6.96-13.98) |
| $t_{last}^{a}$ (day) | 69.00 (42.00-77.05) | 63.00 (28.00-69.00) | 64.99 (41.95-70.07) |
| $t_{1/2z}$ (day) | 8.76 ± 3.12 (8.37) [35.7] | 7.07 ± 1.68 (6.88) [23.8] | 6.72 ± 1.56 (6.55) [23.3] |
| $AUC_{0-D28}$** (mg · day/l) | 445 ± 189 (414) [42.3] | 292 ± 138 (259) [47.3] | 364 ± 143 (338) [39.4] |
| CL/F (l/day) | 0.312 ± 0.124 (0.285) [39.6] | 0.595 ± 0.414 (0.496) [69.6] | 0.409 ± 0.176 (0.372) [43.0] |
| Vss/F (l) | 5.46 ± 1.83 (5.19) [33.4] | 8.44 ± 4.18 (7.62) [49.5] | 6.27 ± 2.17 (5.91) [34.6] |
| MRT (day) | 18.5 ± 3.84 (18.2) [20.7] | 15.6 ± 2.78 (15.4) [17.8] | 16.1 ± 2.62 (15.9) [16.3] |

$^a$Median (Min-Max)
*Concentration in serum on study day 85 (28 days after the third administration)
**Partial AUC calculated between study days 57 and 85 (PK time zero to Day 28)

TABLE 6

Point estimates of geometric mean ratio with 90% confidence interval for treatment period [D1-D29]

| Treatment period | Parameter | Comparison | Estimate | 90% CI |
|---|---|---|---|---|
| [D1-D29] | $C_{max}$ | alirocumab + ezetimibe vs alirocumab alone | 0.97 | (0.82 to 1.14) |
| | | alirocumab + fenofibrate vs alirocumab alone | 0.78 | (0.66 to 0.92) |
| | AUC | alirocumab + ezetimibe vs alirocumab alone | 0.86 | (0.67 to 1.11) |
| | | alirocumab + fenofibrate vs alirocumab alone | 0.73 | (0.57 to 0.95) |
| | $AUC_{last}$ | alirocumab + ezetimibe vs alirocumab alone | 0.88 | (0.76 to 1.03) |
| | | alirocumab + fenofibrate vs alirocumab alone | 0.74 | (0.64 to 0.86) |
| | $AUC_{0-D28}$ | alirocumab + ezetimibe vs alirocumab alone | 0.88 | (0.76 to 1.03) |
| | | alirocumab + fenofibrate vs alirocumab alone | 0.74 | (0.64 to 0.86) |

TABLE 6-continued

| Treatment period | Parameter | Comparison | Estimate | 90% CI |
|---|---|---|---|---|
| Point estimates of geometric mean ratio with 90% confidence interval for treatment period [D57-D126] | | | | |
| [D57-D126] | $C_{max}$ | alirocumab + ezetimibe vs alirocumab alone | 0.92 | (0.78 to 1.09) |
| | | alirocumab + fenofibrate vs alirocumab alone | 0.71 | (0.60 to 0.84) |
| | $AUC_{0-D28}$ | alirocumab + ezetimibe vs alirocumab alone | 0.85 | (0.70 to 1.03) |
| | | alirocumab + fenofibrate vs alirocumab alone | 0.64 | (0.53 to 0.77) |
| | $t_{1/2z}$ | alirocumab + ezetimibe vs alirocumab alone | 0.80 | (0.72 to 0.90) |
| | | alirocumab + fenofibrate vs alirocumab alone | 0.83 | (0.74 to 0.93) |

After the $1^{st}$ injection, alirocumab $C_{max}$ values were similar when comparing alirocumab+ezetimibe versus alirocumab alone with a point estimate of 0.97 (90% CI=0.82 to 1.14). Whereas a trend for reduced $AUC_{0-D28}$ with a point estimate of 0.88 (90% CI=0.76 to 1.03) was seen. Alirocumab serum exposure was reduced when comparing alirocumab+fenofibrate versus alirocumab alone with point estimates of 0.78 (90% CI=0.66 to 0.92) and 0.74 (90% CI=0.64 to 0.86) for $C_{max}$ and $AUC_{0-D28}$, respectively.

After the $3^{rd}$ injection, alirocumab $C_{max}$ values were similar when comparing alirocumab+ezetimibe versus alirocumab alone with a point estimate of 0.92 (90% CI=0.78 to 1.09). $AUC_{0-D28}$ was seen to be reduced with a point estimate of 0.85 (90% CI=0.70 to 1.03). A trend for a shorter half-life (6.72±1.56 versus 8.76±3.12 days) was seen in the alirocumab+ezetimibe versus alirocumab alone group with a point estimate of 0.80 (90% CI=0.72 to 0.90).

Alirocumab serum exposure remained reduced when comparing alirocumab+fenofibrate versus alirocumab alone with point estimates of 0.71 (90% CI=0.60 to 0.84) and 0.64 (90% CI=0.53 to 0.77) for $C_{max}$ and $AUC_{0-D28}$, respectively. Mean half-lives were reduced with a point estimate of 0.83 (90% CI=0.74 to 0.93) when comparing alirocumab+fenofibrate versus alirocumab alone group. Half-lives of 7.07±1.68 days and 8.76±3.12 days were calculated for alirocumab+fenofibrate and alirocumab alone groups, respectively.

Conclusions

LDL-C reductions with EZE and FENO therapy alone observed during the run-in period were as expected.

Alirocumab 150 mg Q4W monotherapy resulted in LDL-C reductions of ~48% (regardless of baseline) which were sustained over the 28-day dosing interval. Combination of alirocumab with EZE or FENO resulted in greater LDL-C reductions than with alirocumab alone: 1) maximum reductions from the main baseline, which included the 28-day run-in with placebo, EZE or FENO, were ~65% with EZE or FENO; 2) corresponding reductions using the additional baseline (from first alirocumab injection) were ~55% with EZE or FENO.

Treatment with FENO alone, and to a lesser extent EZE, resulted in modest increases in free PCSK9 as compared with placebo.

The slight decrease in efficacy observed from 14 to 28 days after dosing with alirocumab in the FENO combination group may be the result of reduced alirocumab exposure due to increase in free PCSK9 levels observed with FENO administration. This also seemed to be the case, to a lesser extent, with the EZE combination.

Previous studies suggested that concomitant statin therapy reduces the duration of efficacy of alirocumab via increased target mediated clearance, requiring every 2 weeks dosing to overcome this. This study suggests that other LLTs (EZE, FENO) may have less of an impact on alirocumab duration of efficacy, and so could be utilized with lower/less frequent doses of alirocumab.

Effects on other lipid parameters were as expected based on previous experience and a similar incidence of TEAEs was reported in all groups.

Results of this study suggest that EZE and FENO therapy results in modest increases in free PCSK9 levels that may explain slightly greater reductions in LDL-C with alirocumab administration as well as a modest reduction in the duration of this maximal effect. However, these data indicate that, unlike in combination with statins, alirocumab 150 mg could be dosed Q4W in the setting of monotherapy and in combination with non-statin LLTs.

Maximum decreases were −47.59%, −65.34%, and −66.75% in the alirocumab alone, ezetimibe, and fenofibrate groups, respectively (change from Day −29 baseline). Administration of alirocumab 150 mg Q4W either alone or on top of ezetimibe (10 mg/day) or fenofibrate (160 mg/day) in healthy subjects produced a decline in LDL-C reaching −47.39%, −56.56%, and −54.34% in the alirocumab alone, ezetimibe, and fenofibrate groups respectively 14 days after the $3^{rd}$ administration of alirocumab, in comparison to pre-alirocumab baseline value. A reduction of −47.03%, −49.57% and −43.17% in the alirocumab alone, ezetimibe, and fenofibrate groups respectively was still observed 28 days after this $3^{rd}$ administration of alirocumab. This suggests a maintenance of the effect when alirocumab was administered alone, whereas a small change from the maximum effect was seen between 2 and 4 weeks post dose in both combination arms. The coadministration of alirocumab with either ezetimibe or fenofibrate produced a similar decline in LDL-C.

When comparing alirocumab+ezetimibe versus alirocumab alone $C_{max}$ values were similar, with a non-significant trend towards lower $AUC_{0-D28}$ in the alirocumab+ezetimibe treatment group and therefore a faster elimination in this group.

Alirocumab PK parameters were significantly reduced by the coadministration of fenofibrate. A daily dose of 160 mg fenofibrate reduced the exposure of alirocumab in serum as described above. An analysis of $t_{max}$ median difference in treatment showed no difference.

The incidences and titers of ADAs were similar for the 3 treatment groups. The serum concentrations of alirocumab in ADA positive and negative subjects were comparable in the 3 treatment groups.

Continuous exposure of ezetimibe or fenofibrate in plasma was confirmed throughout the study period.

Alirocumab administered either alone or on top of ezetimibe or fenofibrate at the dose of 150 mg Q4W for 3 administrations in healthy subjects was well tolerated.

Example 3: A Randomized, Double-Blind, Placebo-Controlled, Parallel-Group Study Evaluating the Efficacy and Safety of Alirocumab in Patients with Primary Hypercholesterolemia not Treated with a Statin Selection of Dose Based on the results of studies carried out with statin as background therapy, the Q2W dosing regimen is appropriate to maintain constant LDL-C lowering throughout the inter-dosing interval in statin-treated patients, with the maximum efficacy at 12 weeks provided by the 150 mg Q2W dosing. However, for many patients, the magnitude of effect observed with the 150 mg Q2W dose may not be needed to achieve the target LDL-C goal, and starting with a lesser dose may be undertaken.

The 150 mg Q4W dosing regimen for alirocumab that will be evaluated in this study is based on the longer duration of action observed in patients not receiving concomitant statin. A statin-stimulated increased production of PCSK9 may affect the duration of action of alirocumab, because higher rates of PCSK9 production may result in greater target-mediated clearance of the antibody. Compared to statins, ezetimibe and fibrates appear to have little or no effect on PCSK9 levels, and a Q4W dosing regimen is expected to maintain sufficient LDL-C lowering throughout the inter-dosing interval in patients not receiving a statin but receiving these lipid-lowering therapies.

Rationale for Protocol Design

The objective of the present study is to assess the efficacy and safety of alirocumab 150 mg Q4W as a potential starting dose in patients not treated with a statin. The current study will provide information on the efficacy, safety and tolerability for an every 4 week dosing regimen, and in patients receiving a background therapy of ezetimibe or fenofibrate or diet alone.

None of the patients selected in this study will receive a statin. A component of the population in the current study is statin intolerant patients.

Overall, a target of ⅔ of patients should receive a background therapy with ezetimibe or fenofibrate.

In this study of patients maintaining their background therapy of ezetimibe or fenofibrate or diet alone, who do not/cannot receive a statin, the choice of placebo as control over the double-blind treatment period appears appropriate for the objectives of this study, since it will provide the most robust assessment of efficacy and safety of 150 mg Q4W. A calibrator arm of alirocumab 75 mg Q2W will provide a bench mark for the starting dose.

To help adjust the dosing regimen of alirocumab to patients' needs, in the phase 3 program, alirocumab is initiated in most studies with a dose expected to provide a 50% reduction in LDL-C at steady state (75 mg Q2W program). In all the studies with 75 mg Q2W as a starting dose, the dose is increased to 150 mg Q2W at Week 12, based on LDL-C level achieved at Week 8. In the current study assessing 150 mg Q4W as a potential starting dose in non-statin treated patients, the up-titration, if needed, will also be performed at week 12, as in all other studies of the program. In the whole program, the primary efficacy is assessed after titration has taken place, as needed. In this study, the primary efficacy parameter will be assessed at week 24. The 12-week efficacy assessment (i.e., before up-titration) will be important to consider, and will therefore be analyzed as a key secondary endpoint.

A 24 week duration for the double-blind period is considered adequate to provide safety information on a dosing regimen including 150 mg Q4W as a starting dose, as exposure to alirocumab ($C_{max}$ and AUC) will be in between that observed with 75 mg Q2W and 150 mg Q2W, for which a large database will be available, over a longer duration. In the post-titration period, patients not reaching LDL-C goal will receive 150 mg Q2W, as in the rest of the program. To obtain additional safety data with this Q4W dosing, patients may participate in an optional open-label treatment period from week 24 to June 2016.

This specific study is undertaken to demonstrate the safety and the reduction of low-density lipoprotein cholesterol (LDL-C) with a regimen including alirocumab 150 mg Q4W as a starting dose, as add-on to non-statin lipid modifying background therapy (ezetimibe or fenofibrate) or with diet alone in comparison with placebo in patients with primary hypercholesterolemia not treated with a statin. The statin intolerant population that is not at LDL-C goal on optimized LMT (ezetimibe or fenofibrate) or on diet alone represents a group with an identified unmet medical need that can be addressed by adding alirocumab to their LDL-C lowering therapies. At the end of the 24-week double-blind treatment period, background therapy can be adjusted as needed in patients opting to enter the optional open-label treatment period.

Study Objectives

The primary objective of the study is to demonstrate the reduction of low-density lipoprotein cholesterol (LDL-C) by a regimen including an alirocumab starting dose of 150 mg Q4W as add-on to non-statin lipid modifying background therapy or as monotherapy in comparison with placebo in patients with primary hypercholesterolemia not treated with a statin.

The secondary objectives are: to evaluate the effect of alirocumab, with 150 mg Q4W as starting dose, in comparison with placebo on other lipid parameters (e.g., Apolipoprotein B (ApoB), non-high density lipoprotein cholesterol (non-HDL-C), Total-Cholesterol (TC), Lipoprotein (a) (Lp [a]), high-density lipoprotein cholesterol (HDL-C), Triglycerides (TG) and Apolipoprotein A-1 (Apo A-1) levels; to evaluate the safety and tolerability of alirocumab 150 mg Q4W; to evaluate the development of anti-alirocumab antibodies; and to evaluate the pharmacokinetics (PK) of alirocumab 150 mg Q4W.

Other objectives are to evaluate efficacy and safety of a Q2W dosing regimen of 75 mg alirocumab.

Study Design

This is a randomized, double-blind, placebo-controlled, parallel-group, multi-center phase 3 study. Randomization will be stratified according to the statin intolerant status and non-statin lipid modifying background therapy. Only patients not receiving a statin will be included. Statin intolerant patients at moderate, high or very high CV risk as defined below in the population section will represent a target of approximately 50% of the study population. Statin intolerance is defined for the trial as the inability to tolerate at least two statins: one statin at the lowest daily starting dose (defined as rosuvastatin 5 mg, atorvastatin 10 mg, simvastatin 10 mg, lovastatin 20 mg, pravastatin 40 mg, fluvastatin 40 mg, or pitavastatin 2 mg or as the lowest approved daily dose by country specific labeling), and another stating at any dose, due to skeletal muscle-related symptoms, other than those due to strain or trauma, such as pain, aches, weakness, or cramping, that began or increased during statin therapy and stopped when statin therapy was discontinued. Patients at moderate CV risk, not fulfilling the SI definition, will comprise the rest of the study population.

For the background therapy, a target of approximately ⅔ of patients will receive a background therapy (fenofibrate or ezetimibe) and up to ⅓ patients will be treated with diet alone.
The study comprises four periods:
1) A screening period of up to 3 weeks,
2) A double-blind, parallel-group treatment period of 24 weeks over which patients will receive double-blind study treatment as follows:
Alirocumab 150 mg subcutaneous every 4 weeks*
OR
Placebo for alirocumab subcutaneous every 2 weeks
OR
Alirocumab 75 mg subcutaneous every 2 weeks.
* the blind will be maintained in the alirocumab 150 mg every 4 weeks alternating with placebo SC Q4W.
At the week 12 visit, based on their LDL-C at week 8 and baseline CV risk, patients will, in a blinded manner, either continue receiving alirocumab 150 mg Q4W or 75 mg Q2W or will have their dose up-titrated, as follows:
i) Patients with very high CV risk will, in a blinded manner, either:
  continue receiving alirocumab 150 mg Q4W or 75 mg Q2W from week 12 onwards until the last injection at week 22, if their week 8 LDL-C is <70 mg/dL (1.81 mmol/L) and they had at least a 30% reduction of LDL-C from baseline at week 8; or
  receive a dose that is up-titrated to alirocumab 150 mg Q2W from Week 12 onwards until the last injection at week 22, if their week 8 LDL-C is ≥70 mg/dL (1.81 mmol/L) or they do not have at least 30% reduction of LDL-C from baseline at Week 8.
ii) Patients with high or moderate CV risk will, in a blinded manner, either:
  continue receiving alirocumab 150 mg Q4W or 75 mg Q2W from Week 12 onwards until the last injection at week 22, if their week 8 LDL-C is <100 mg/dL (2.59 mmol/L) and they had at least a 30% reduction of LDL-C from baseline at week 8; or
  receive a dose that is up-titrated to alirocumab 150 mg Q2W from Week 12 onwards until the last injection at week 22, if their week 8 LDL-C is ≥100 mg/dL (2.59 mmol/L) or they do not have at least 30% reduction of LDL-C from baseline at Week 8.
3) A follow-up period of 8 weeks after the end of double-blind treatment period.
Patients who are not eligible for the open-label treatment period will be followed for a period of 8 weeks after the end of the double-blind treatment period if they do not opt to or are not eligible to participate in the open-label treatment period. The 8-week follow-up period will not apply to patients who are eligible and choose to enroll in the open-label treatment period.
4) An optional open-label treatment period.
Patients who successfully complete the double-blind treatment period will be eligible (provided they have not experienced any treatment-related AEs, or had significant protocol deviations) to enter an optional open-label treatment period.
Patients will receive alirocumab 150 mg Q4W at the start of the open-label treatment period. The first injection during the open-label treatment period will be administered at the site at the week 24 visit (the first visit of the open-label treatment period).
From week 36 visit, based on LDL-C value at week 32, the Investigator will manage, based on his/her own judgment, adjustment of alirocumab doses. At week 36, patients will either continue receiving alirocumab 150 mg Q4W or will receive a dose that is up-titrated to alirocumab 150 mg Q2W. Subsequent down titration to 150 mg Q4W will be allowed.
Although the background therapies should be maintained stable if possible, they might be adjusted based on Investigator judgment, in particular in case of tolerability issue.
For adjustments based on LDL-C values, the Investigator can modify background therapy as needed. However, simultaneous adjustments in alirocumab dose and any LMT should be avoided.
Treatment for these patients will continue uninterrupted from the last dose of study drug during the double-blind treatment period (week 22) to week 24 (the first dose in the open-label treatment period) onward, until June 2016.
Duration of Study Participation
The study duration includes a screening period of up to 3-weeks, a 24-week double-blind treatment period for efficacy and safety assessment, and an 8-week post-treatment follow-up period for patients who are not eligible for the open-label treatment period after the last visit of the DBTP. Thus the study duration per patient is about 35 weeks+an optional open-label treatment period. The 8-week follow-up period will not apply to patients who are eligible and choose to enroll in the open-label treatment period. Patients who successfully complete the double-blind treatment period will be eligible (provided they have not experienced any treatment-related AEs, or had significant protocol deviations) to enter an optional open-label treatment period.
Selection of Patients
Patients meeting all of the following criteria will be considered for enrollment into the study. Patients with Primary hypercholesterolemia (heFH or non-FH) receiving fenofibrate or ezetimibe or diet alone. Only patients not receiving a statin will be included in the study, which correspond to patients: who are intolerant to statins* as defined below with moderate, high, or very high CV risk; or who are not fulfilling the SI definition. Only patients at moderate CV risk will be included in this stratum.
*Statin intolerance is defined as the inability to tolerate at least 2 statins: 1 statin at the lowest daily starting dose (defined as rosuvastatin 5 mg, atorvastatin 10 mg, simvastatin 10 mg, lovastatin 20 mg, pravastatin 40 mg, fluvastatin 40 mg or pitavastatin 2 mg or as the lowest approved daily dose by country specific labeling), AND another statin at any dose, due to skeletal muscle-related symptoms, other than those due to strain or trauma, such as pain, aches, weakness, or cramping, that began or increased during statin therapy and stopped when statin therapy was discontinued.
Moderate CV risk is defined as a calculated 10-year fatal CVD risk SCORE ≥1 and <5% (ESC/EAS 2012).
High CV risk is defined as a calculated 10-year fatal CVD risk SCORE ≥5% (ESC/EAS 2012), or moderate chronic kidney disease (CKD), or type 1 or type 2 diabetes mellitus without target organ damage, or heFH (NCEP-ATP III, ESC/EAS 2012).
Very high CV risk is defined as a history of documented CHD, ischemic stroke, peripheral arterial disease (PAD), transient ischemic attack (TIA), abdominal aortic aneurysm, carotid artery occlusion >50% without symptoms, carotid endarterectomy or carotid artery stent procedure, renal artery stenosis, renal artery stent procedure, type 1 or type 2 diabetes mellitus with target organ damage (NCEP-ATP III, ESC/EAS 2012).
A documented history of CHD (includes 1 or more of the following): acute MI, silent MI, unstable angina, coronary revascularization procedure (e.g., percutaneous coronary intervention [PCI] or coronary artery bypass graft surgery [CABG]), and clinically significant CHD diagnosed by invasive or non-invasive testing (such as coronary angiography, stress test using treadmill, stress echocardiography or nuclear imaging).

Patients who have met all the above inclusion criteria will be screened for exclusion criteria. Exclusion criteria for the double-blind period are: patients defined as statin intolerant and very high CV risk with LDL-C <70 mg/dL (1.81 mmol/L) at the screening visit (Week-3, V1); patients defined as statin intolerant and high or moderate CV risk with LDL-C <100 mg/dL (<2.59 mmol/L) at the screening visit (Week-3, V1); patients not fulfilling the statin intolerant definition and who are at moderate CV risk with LDL-C <100 mg/dL (<2.59 mmol/L), at the screening visit (Week-3, V1); patients with LDL-C ≥160 mg/dL (≥4.1 mmol/L) at the screening visit (Week-3, V1) if receiving diet only, whatever the statin intolerance status or if non fulfilling statin intolerance definition at moderate CV risk and treated with ezetimibe or fenofibrate; with a 10-year fatal CVD risk SCORE <1% (ESC/EAS 2011) at the screening visit (Week-3, V1); newly diagnosed (within 3 months prior to randomization visit [Week 0]) or poorly controlled (HbA1c >9%) diabetes; with use of statin, red yeast rice products, niacin or bile acid sequestrant within 4 weeks of the screening visit (Week-3) or between screening and randomization visits; not on a stable dose of ezetimibe or fenofibrate for at least 4 weeks, prior to the screening visit (Week-3, V1) or between screening and randomization visits; with use of fibrates, other than fenofibrate, within 4 weeks of the screening visit (Week-3, V1) or between screening and randomization visits; with use of nutraceuticals or over-the-counter therapies known to affect lipids, at a dose/amount that has not been stable for at least 4 weeks, prior to the screening visit (Week-3, V1) or between screening and randomization visits; planned to undergo scheduled PCI, CABG, carotid or peripheral revascularization during the study; systolic blood pressure (BP) >160 mmHg or diastolic BP >100 mmHg at screening (Week-3, V1) and/or randomization (Week 0) visits; history of New York Heart Association Class III or IV heart failure within the past 12 months; history of a MI, unstable angina leading to hospitalization, CABG, PCI, uncontrolled cardiac arrhythmia, carotid surgery or stenting, stroke, transient ischemic attack, carotid revascularization, endovascular procedure or surgical intervention for peripheral vascular disease within 3 months prior to the screening visit (Week-3, V1); known history of hemorrhagic stroke; age <18 years or legal age of majority at the screening visit (Week-3, V1) whichever is older; patients not previously instructed on a cholesterol-lowering diet prior to the screening visit (Week-3, V1); presence of any clinically significant uncontrolled endocrine disease known to influence serum lipids or lipoproteins; history of bariatric surgery within 12 months prior to the screening visit (Week-3, V1); unstable weight defined by a variation >5 kg within 2 months prior to the screening visit (Week-3, V1); known history of homozygous FH; known history of loss of function of PCSK9 (i.e., genetic mutation or sequence variation); use of systemic corticosteroids, unless used as replacement therapy for pituitary/adrenal disease with a stable regimen for at least 6 weeks prior to randomization; history of cancer within the past 5 years, except for adequately treated basal cell skin cancer, squamous cell skin cancer, or in situ cervical cancer; known history of a positive HIV test; patient who has taken any active investigational drugs within 1 month or 5 half-lives, whichever is longer; patient who has been previously treated with at least one dose of alirocumab or any other anti-PCSK9 monoclonal antibody in other clinical trials; use of continuous hormone replacement therapy unless the regimen has been stable in the past 6 weeks prior to the Screening visit (Week-3) and no plans to change the regimen during the study; patient who withdraws consent during the screening period (patient who is not willing to continue or fails to return); conditions/situations or laboratory findings such as: any clinically significant abnormality identified at the time of screening that in the judgment of the Investigator or any sub-Investigator would preclude safe completion of the study or constrain endpoints assessment such as major systemic diseases, patients with short life expectancy, patients considered by the Investigator or any sub-Investigator as inappropriate for this study for any reason, e.g.: those deemed unable to meet specific protocol requirements, such as scheduled visits, those deemed unable to administer or tolerate long-term injections as per the patient or the investigator, investigator or any sub-Investigator, pharmacist, study coordinator, other study staff or relative thereof directly involved in the conduct of the protocol, etc., presence of any other conditions (e.g., geographic, social . . . ) actual or anticipated, that the Investigator feels would restrict or limit the patient's participation for the duration of the study; laboratory findings during the screening period (not including randomization labs): positive test for Hepatitis B surface antigen or Hepatitis C antibody, positive serum or urine pregnancy (including Week 0) test in women of childbearing potential, triglycerides >400 mg/dL (>4.52 mmol/L) (1 repeat lab is allowed), eGFR <30 mL/min/1.73 m2 according to 4-variable MDRD Study equation (Calculated by central lab), ALT or AST >3×ULN (1 repeat lab is allowed), CPK >3×ULN (1 repeat lab is allowed), TSH <LLN or >ULN (for patients on thyroid replacement therapy see earlier exclusion criterion; known hypersensitivity to monoclonal antibody or any component of the drug product; and pregnant or breast-feeding women (women of childbearing potential not protected by highly-effective method(s) of birth control (as defined in the informed consent form and/or in a local protocol addendum) and/or who are unwilling or unable to be tested for pregnancy)

Exclusion criteria for the open-label period are: significant protocol deviation in the double-blind period based on the Investigator judgment, such as non-compliance by the patient; any patient who experienced an adverse event leading to permanent discontinuation from the double-blind period; patients having any new condition or worsening of existing condition which in the opinion of the Investigator would make the patient unsuitable for enrollment, or could interfere with the patient participating in or completing the study; known hypersensitivity to monoclonal antibody or any component of the drug product; positive pregnancy test at last visit of the double-blind period (W24, Visit 11); and women of childbearing potential not willing to continue highly-effective method(s) of birth control (as defined in the informed consent form and/or in a local protocol addendum) and/or who are unwilling or unable to be tested for pregnancy.

Study Treatments

For the double-blind treatment period, the study treatment is a single SC injection of 1 mL for a 75 or 150 mg dose of alirocumab or placebo provided in an auto-injector, administered in the abdomen, thigh, or outer area of the upper arm.

During the double-blind treatment period (Week 0 to 24), eligible patients will be randomized to receive: alirocumab 150 mg subcutaneous every 4 weeks alternating with placebo of alirocumab subcutaneous every 4 weeks, or alirocumab 75 mg subcutaneous every 2 weeks, or placebo subcutaneous every 2 weeks.

Study drug will be administered by SC injection Q2W, starting at week 0 and continuing up to the last injection (week 22), 2 weeks before the end of the double-blind treatment period.

At the week 12 visit, based on their LDL-C at week 8 and baseline CV risk, patients will either continue receiving alirocumab 150 mg Q4W or 75 mg Q2W or will have their dose up-titrated, as follows:

1) Patients with very high CV risk will, in a blinded manner, either: continue receiving alirocumab 150 mg Q4W or 75 mg Q2W from week 12 onwards until the last injection at week 22, if their week 8 LDL-C is <70 mg/dL (1.81 mmol/L) and they had at least a 30% reduction of LDL-C from baseline at week 8, or receive a dose that is up-titrated to alirocumab 150 mg Q2W from week 12 onwards until the last injection at week 22, if their week 8 LDL-C is ≥70 mg/dL (1.81 mmol/L) or they do not have at least a 30% reduction of LDL-C from baseline at week 8.

2) Patients with high or moderate CV risk, will, in a blinded manner, either: continue receiving alirocumab 150 mg Q4W or 75Q2W from week 12 onwards until the last injection at week 22, if their week 8 LDL-C is <100 mg/dL (2.59 mmol/L) and they had at least a 30% reduction of LDL-C from baseline at week 8, or receive a dose that is up-titrated to alirocumab 150 mg Q2W from week 12 onwards until the last injection at week 22, if their week 8 LDL-C is ≥100 mg/dL (2.59 mmol/L) or they do not have at least a 30% reduction of LDL-C from baseline at week 8.

During the open-label treatment period (from week 24 to June 2016), eligible patients will receive: alirocumab 150 mg Q4W up to week 36; and from week 36, according to LDL-C measurement at week 32 and the judgment of the investigator, patients will either: continue receiving alirocumab 150 mg Q4W, or receive a dose that is up-titrated to alirocumab 150 mg Q2W from week 36 onwards until June 2016. Subsequent down titration to 150 mg Q4W will be allowed.

During the open-label treatment period, all patients will receive alirocumab 150 mg Q4W from week 24 to week 36. At the week 36 visit, based on their LDL-C at week 32, patients will either continue to receive alirocumab 150 mg Q4W or will have their dose up-titrated to alirocumab 150 mg Q2W at the judgment of the investigator. Subsequent down titration to 150 mg Q4W will be allowed.

Although the background therapies should be maintained stable if possible, they might be adjusted based on Investigator judgment, in particular in case of tolerability issue. For adjustments based on LDL-C values, the Investigator can modify background therapy as needed. However, simultaneous adjustments in alirocumab dose and any LMT should be avoided.

Assessment of Alirocumab

The primary efficacy endpoint will be the percent change in calculated LDL-C from baseline to Week 24, which is defined as: 100×(calculated LDL-C value at Week 24−calculated LDL-C value at baseline)/calculated LDL-C value at baseline.

The baseline calculated LDL-C value will be the last LDL-C level obtained before the first double-blind injection IMP. For patients randomized and not treated, the baseline value is defined as the last available value obtained up to randomization.

The calculated LDL-C at Week 24 will be the LDL-C level obtained within the Week 24 analysis window.

The main secondary efficacy endpoint(s) are: The percent change in calculated LDL-C from baseline to Week 12: similar definition and rules as for primary efficacy endpoint, except that the calculated LDL-C at Week 12 will be the LDL-C level obtained within the Week 12 analysis window; the percent change in Apo B from baseline to Week 24. Same definition and rules as for to the primary endpoint; the percent change in non-HDL-C from baseline to Week 24. Same definition and rules as for to the primary endpoint; the percent change in TC from baseline to Week 24. Same definition and rules as for to the primary endpoint; the percent change in Apo B from baseline to Week 12. Same definition and rules as for to the percent change in calculated LDL-C from baseline to Week 12; the percent change in non-HDL-C from baseline to Week 12. Same definition and rules as for to the percent change in calculated LDL-C from baseline to Week 12; the percent change in TC from baseline to Week 12. Same definition and rules as for to the percent change in calculated LDL-C from baseline to Week 12; the proportion of patients reaching calculated LDL-C <70 mg/dl (1.81 mmol/L) at Week 24 for very high CV risk patients or <100 mg/dl (2.59 mmol/L) for other patients using definition and rules used for the primary endpoint; the percent change in Lp(a) from baseline to Week 24; the percent change in HDL-C from baseline to Week 24; the percent change in HDL-C from baseline to Week 12; the percent change in Lp(a) from baseline to Week 12; the percent change in fasting TG from baseline to Week 24; the percent change in fasting TG from baseline to Week 12; the percent change in Apo A-1 from baseline to Week 24; and the percent change in Apo A-1 from baseline to Week 12.

Other secondary efficacy endpoints are: the proportion of patients reaching LDL-C <70 mg/dL (1.81 mmol/L) for very high CV risk patients or <100 mg/dL (2.59 mmol/L) for other patients at Week 12; the proportion of patients with LDL-C <100 mg/dL (2.59 mmol/L) at Weeks 12 and 24 whatever the CV risk patients; the proportion of patients with LDL-C <70 mg/dL (1.81 mmol/L) at Weeks 12 and 24 for very high CV risk patients; the absolute change in LDL-C (mg/dL and mmol/L) from baseline to Weeks 12 and 24; the change in ratio Apo B/Apo A-1 from baseline to Weeks 12 and 24; the proportion of patients with Apo B <80 mg/dL (0.8 g/L) at Weeks 12 and 24; the proportion of patients with non-HDL-C <100 mg/dL (2.59 mmol/L) at Weeks 12 and 24; the proportion of very high CV risk patients with LDL-C <70 mg/dL (1.81 mmol/L) and/or ≥50% reduction in LDL-C (if LDL-C ≥70 mg/dL) at Week 12 and 24; the proportion of patients achieving at least 50% reduction in LDL-C at Weeks 12 and 24.

The lipid parameters will be assessed as follows. Total-C, HDL-C, TG, Apo B, Apo A-1, and Lp(a) will be directly measured. LDL-C will be calculated using the Friedewald formula at all visits (except Week-1 and Follow-Up visit). If TG values exceed 400 mg/dL (4.52 mmol/L) then the lab will reflexively measure (via the beta quantification method) the LDL-C rather than calculating it. LDL-C will also be measured (via the beta quantification method) at Week 0 and Week 24 in all patients. Non-HDL-C will be calculated by subtracting HDL-C from the total-C. Ratio Apo B/Apo A-1 will be calculated.

The clinical laboratory data consist of urinalysis and blood analysis, hematology (RBC count, red blood cell distribution width (RDW), reticulocyte count, hemoglobin, hematocrit, platelets, WBC count with differential blood count), standard chemistry (glucose, sodium, potassium, chloride, bicarbonate, calcium, phosphorous, urea nitrogen, creatinine, uric acid, total protein, LDH, albumin, γ Glutamyl Transferase [γGT]), Hepatitis C antibody, liver panel (ALT, AST, ALP, and total bilirubin), and CPK. Some additional safety laboratory parameters may be reflexively measured, based on actual data.

The following vital signs will be measured: heart rate, systolic and diastolic BP in sitting position.

The ECG data will be measured.

Anti-alirocumab antibodies will be assessed and include the antibody status (positive/negative) and antibody titers.

The percent change in hs-CRP will be assessed from baseline to Week 12 and Week 24.

The absolute change in HbA1c (%) will be assessed from baseline to Week 12 and Week 24.

EQ-5D is a standardized measure of health status developed by the EuroQol Group in order to provide a simple, generic measure of health for clinical and economic appraisal. The EQ-5D as a measure of health related quality of life, defines health in terms of 5 dimensions: mobility, self-care, usual activities, pain/discomfort, anxiety/depression. Each dimension can take one of three responses (3 ordinal levels of severity): 'no problem' (1) "some problems" (2) "severe problems" (3). Overall health state is defined as a 5-digit number. Health states defined by the 5-dimensional classification can be converted into corresponding index scores that quantify health status, where 0 represents 'death' and 1 represents "perfect health". EQ-5D variables include response of each EQ-5D items, index score and change of index score from baseline.

Pharmacokinetic variables include total serum alirocumab concentration. Total and free PCSK9 concentrations will be measured from the same PK sample.

An optional pharmacogenomic sub-study will be conducted to identify genetic associations with clinical or biomarker response to PCSK9 inhibition, hyperlipidemia, or CVD. If needed, samples may also be used to identify markers associated with toxicity. Analyses may include sequence determination or single nucleotide polymorphisms (SNP) from candidate genes. Candidate genes may include (but are not limited to) PCSK9, Apo B and LDL-R. Genome-wide studies, including (but not limited to) SNP analyses and/or genomic sequencing may also be performed.

Study Procedures

For all visits after Day 1/Week 0 (randomization visit), a timeframe of a certain number of days will be allowed. The window period for all visits until Week 24 is ±3 days and for the follow-up period it is ±7 days. During the open label period, the visit window is ±5 days for visit Week 28, 32, 36 & ±7 days for the other visits.

The blood sampling for determination of lipid parameters (i.e., total-C, LDL-C, HDL-C, TG, non-HDL-C, Apo B, Apo A-1, ratio Apo B/Apo A-1, Lp[a]) should be performed in the morning, in fasting condition (i.e. overnight, at least 10 to 12 hours fast and refrain from smoking).

The following laboratory data are collected: Hematology; Chemistry; Lipid panel 1: TC, calculated LDL-C, HDL-C, TG, non-HDL-C; Lipid panel 2: ApoB, ApoA-1, ratio ApoB/ApoA-1, and Lp(a); Liver panel: in case of total bilirubin values above the normal range, differentiation into conjugated and non-conjugated bilirubin will occur automatically; Creatine Phosphokinase (CPK); Hepatitis B surface antigen; Hepatitis C antibody: positive tests will be confirmed with reflexive testing; Serum pregnancy test.

Urinalysis—dipstick will be performed and will assess for pH, specific gravity, and for the presence of blood, protein, glucose, ketones, nitrates, leukocyte esterase, uro-bilinogen and bilirubin. If the dipstick is abnormal then standard microscopy will be conducted.

All other blood parameters will also be measured during the study. Glycemic parameters (HbA1c and serum glucose) will be measured. The blood sampling for inflammatory parameter, hs-CRP will be collected periodically throughout the study.

Serum samples for assessment of alirocumab concentration will be obtained periodically throughout the study. Blood samples will be collected before IMP injection for visits 3 (week 0), 4 (week 4), 5 (week 8), 6 (week 9), 7 (week 10), 8 (week 11), 9 (week 12), 10 (week 16) and 11 (week 24). Blood samples should be collected before IMP injection.

Library (plasma and serum) samples will be collected periodically throughout the study. The first scheduled sample at randomization visit will be obtained before IMP injection (predose). Library samples may include the study of PCSK9 levels, PCSK9 function, effect(s) of PCSK9 inhibition with a monoclonal antibody, lipoprotein sub-fractionation, and mechanisms of hyperlipidemia and heart disease. If needed, samples may also be used to identify markers associated with toxicity. The library samples will never be used for genomic analysis.

A general physical examination should be performed at various points throughout the study.

BP should be measured in sitting position under standardized conditions, approximately at the same time of the day, on the same arm, with the same apparatus (after the patient has rested comfortably in sitting position for at least 5 minutes). Heart rate will be measured at the time of the measurement of BP.

The 12-lead ECGs should be performed after at least 10 minutes rest and in the supine position.

Body weight should be obtained with the patient wearing undergarments or very light clothing and no shoes, and with an empty bladder. Height should also be obtained.

Visit Schedule

Only patients who meet the inclusion criteria should be screened. The screening period will take place up to 3 weeks or 21 days (and as short as possible, upon receipt of laboratory eligibility criteria) prior to randomization/Day 1 visit. The Screening Visit (Visit1/Week-3/Day −21 up to −8) will include: Assess inclusion/exclusion criteria; Obtain patient demography—age, gender, race, and ethnicity; Obtain medical history (including menopausal status), surgical history, alcohol habits, and smoking habits; Obtain family medical history (including risk factors relating to premature CHD (before 55 years of age in a male, 65 years in a female first degree relative), allergy and Type 2 diabetes); Document prior medication history within the previous 12 weeks, especially for lipid modifying therapy (including statin) and nutraceutical products that may affect lipids (e.g., omega-3 fatty acids, plant stanols such as found in Benecol, flax seed oil, psyllium); Record concomitant medication; Get body weight and height measurements. Take vital signs including HR and BP; Perform physical examination.

The Injection training visit at Screening (Visit2/Week-1/Day −7±3) will include the following: Assess inclusion/exclusion criteria; Collect AEs; Record concomitant medication; Take vital signs including HR and BP.

The Randomization visit (Visit 3/Week 0/Day 1+3) will include the following: Assess Inclusion/Exclusion Criteria; Collect AEs; Record concomitant medication; Review patient's diet. Patient should be on a NCEP-ATPIII TLC diet or equivalent; Perform physical examination; Get body weight measurement; Take vital signs including HR and BP; Urinalysis (dipstick and if abnormal then microscopy); Urine pregnancy test (women of childbearing potential only); Obtain fasting blood sample for: Lipids: measure and/or calculation of total-C, LDL-C (calculated and measured LDL), HDL-C, TG, non-HDL-C, Apo B, Apo A-1, ratio Apo B/Apo A-1, and Lp(a); hs-CRP; Library samples; Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, LDH, total protein, albumin, and γGT; Liver panel (ALT, AST, ALP, and total bilirubin); CPK; Anti-alirocumab antibodies; Serum alirocumab concentration (PK); and Genomic specimen collection.

Visit 4/Week 4, (Day 29±3) will include the following: Collect AEs; Record concomitant medication; Take vital signs including HR and BP; Data collection on IMP administration and IMP compliance check by review of diary; Obtain fasting blood sample for: Lipids: measure or calculation of total-C, LDL-C, HDL-C, TG, non-HDL-C; Liver panel (ALT, AST, ALP, and total bilirubin); Serum alirocumab concentration (PK); and Anti-alirocumab antibodies.

Visit 5/Week 8 (Day 57±3) will include the following: Collect AEs; Record concomitant medication; Take vital signs including HR and BP; Data collection on IMP administration and IMP compliance check by review of diary; Obtain fasting blood sample for: Liver panel (ALT, AST, ALP, and total bilirubin), Lipids: measure or calculation of total-C, LDL-C, HDL-C, TG, non-HDL-C, Apo B, Apo A-1, ratio Apo B/Apo A-1, and Lp(a), Serum alirocumab concentration (PK), and Anti-alirocumab antibodies.

Visits 6, 7, 8/Week 9, 10, 11 (Day 64, 71, 78±3) will include the following: Blood samples should be collected before IMP injection; Serum alirocumab concentration (PK); Lipids: measure or calculation of total-C, LDL-C, HDL-C, TG, non-HDL-C; and Concomitant medications.

Visit 9/Week 12 (Day 85±3) will include the following: Collect AEs; Record concomitant medication; Get body weight measurement; Take vital signs including HR and BP; Review patient's diet. Patient should be on a NCEP-ATPIII TLC diet or equivalent; Perform 12-lead ECG; EQ-5D patient questionnaire; Urinalysis (dipstick and if abnormal then microscopy); Urine pregnancy test (women of childbearing potential only); Obtain fasting blood sample for: Lipids: measure and/or calculation of total-C, LDL-C, HDL-C, TG, non-HDL-C, Apo B, Apo A-1, ratio Apo B/Apo A-1, and Lp(a); Library samples; Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, LDH, total protein, albumin, and γGT. HbA1c and hs-CRP; Liver panel (ALT, AST, ALP, and total bilirubin); CPK; Anti-alirocumab antibodies; Serum alirocumab concentration (PK).

Visit 10/Week 16 (Day 113±3) will include the following: Collect AEs; Record concomitant medication; Get body weight measurement; Take vital signs including HR and BP; Perform 12-lead ECG; Data collection on IMP administration and IMP compliance check by review of diary; EQ-5D patient questionnaire; Urinalysis (dipstick and if abnormal then microscopy); Urine pregnancy test (females of childbearing potential only); Obtain fasting blood sample for: Lipids: measure and/or calculation of total-C, LDL-C, HDL-C, TG, non-HDL-C, Apo B, Apo A-1, ratio Apo B/Apo A-1, and Lp(a); Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, LDH, total protein, albumin, and γGT. HbA1c and hs-CRP; Liver panel (ALT, AST, ALP, and total bilirubin); CPK; Anti-alirocumab antibodies; and Serum alirocumab concentration (PK).

Visit 11/Week 24/End of double-blind period (Day 169±3) will include the following: Collect AEs; Record concomitant medication; Get body weight measurement; Take vital signs including HR and BP; Perform 12-lead ECG; Perform physical examination; EQ-5D patient questionnaire; Review patient's diet. Patient should be on a NCEP-ATPIII TLC diet or equivalent; Urinalysis (dipstick and if abnormal then microscopy); Urine pregnancy test (women of childbearing potential only); Obtain fasting blood sample for: Lipids: measure and/or calculation of total-C, LDL-C (calculated and measured LDL), HDL-C, TG, non-HDL-C, Apo B, Apo A-1, ratio Apo B/Apo A-1, and Lp(a); hs-CRP; Library samples; Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, total protein, albumin, and γGT; Hepatitis B and C Antibody Test (with automatic confirmatory testing if positive); HbA1c; Liver panel (ALT, AST, ALP, and total bilirubin); CPK; Anti-alirocumab antibodies; and Serum concentration alirocumab (PK).

The Follow Up Visit (Visit 12/Week 32/Day 225±7) will include the following: Collect AEs; Record concomitant medication; Take vital signs including HR and BP; Perform physical examination (only in case of clinically relevant abnormality at the end of treatment visit); Urinalysis (only in case of clinically relevant abnormal value at the end of treatment visit); Urine pregnancy test (women of childbearing potential only); Obtain fasting blood sample for: Anti-alirocumab antibodies. Only in case of clinically relevant abnormal values for these parameters at the end of treatment visit will the following be obtained at this visit: •Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, total protein, LDH, albumin, and γGT; Liver panel (ALT, AST, ALP, and total bilirubin); and CPK.

Open Label Treatment Period (Optional)

Patients who successfully complete the double-blind treatment period will be eligible (provided they have not experienced any treatment-limiting non-skeletal muscle-related AEs, or had significant protocol deviations) to enter an optional open-label treatment period. Treatment for these patients will continue uninterrupted from the last dose of study drug during the double-blind treatment period (week 22) to week 24 (the first dose in the open-label treatment period) onward, until June 2016.

At Visit 11/Week 24, patients will undergo end of double-blind treatment period assessments and baseline open-label treatment period assessments, concurrently. Study site personnel should review treatment requirements of the open-label treatment period with patients and remind patients that dosing in the open-label treatment period begins at this visit. The following information will be collected: Assess Exclusion Criteria for open-label treatment period; All evaluations performed for the end of the double-blind treatment period are the same for the first visit of the open-label treatment period; review patient's diet. Patient should be on a NCEP-ATPIII TLC diet or equivalent. If the patient is confirmed eligible (and in fasting conditions), the Investigator will start the next study procedures: The first open-label IMP injection will take place, but only after the collection of the fasting blood samples and after the assessment of all evaluations planned at that visit.

Visit 12/Week 28 will include the following: Collect AEs; Record concomitant medication; Urine pregnancy test; Review patient's diet. Patient should be on a NCEP-ATPIII TLC diet or equivalent; Data collection on IMP administration and IMP compliance check by review of diary; and Obtain fasting blood sample for: Liver panel (ALT, AST, ALP, and total bilirubin).

Visit 13/Week 32 will include the following: Collect AEs; Record concomitant medication; Urine pregnancy test; Review patient's diet. Patient should be on a NCEP-ATPIII TLC diet or equivalent; Data collection on IMP administration and IMP compliance check by review of diary; Obtain fasting blood sample for: Liver panel (ALT, AST, ALP, and total bilirubin); Lipids: measure or calculation of total-C, LDL-C, HDL-C, TG, non-HDL-C; HbA1c; Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, LDH, total protein, albumin, and γGT; and CPK.

Visit 14/Week 36 will include the following: Collect Aes; Record concomitant medication; Get body weight measurement; Take vital signs including HR and BP; Perform physical examination; Review patient's diet. Patient should be on a NCEP-ATPIII TLC diet or equivalent; EQ-5D patient questionnaire; Urine pregnancy test (women of childbearing potential only); Obtain fasting blood sample for: Lipids: measure and/or calculation of total-C, LDL-C, HDL-C, TG, non-HDL-C, Apo B, Apo A-1, ratio Apo B/Apo A-1, and Lp(a); Liver panel (ALT, AST, ALP, and total bilirubin); Anti-alirocumab antibodies.

Visits 15, 17, 19/Week 48, 72, 96 will include the following: Collect AEs; Record concomitant medication; Get body weight measurement; Take vital signs including HR and BP; Review patient's diet. Patient should be on a NCEP-ATPIII TLC diet or equivalent; Perform physical examination; Data collection on IMP administration and IMP compliance check by review of diary and treatment kit; EQ-5D patient questionnaire; Urinalysis (dipstick and if abnormal then microscopy); Urine pregnancy test (women of childbearing potential only); Obtain fasting blood sample for: Lipids: measure and/or calculation of total-C, LDL-C, HDL-C, TG, non-HDL-C; Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, total protein, albumin, and γGT; HbA1c; Liver panel (ALT, AST, ALP, and total bilirubin); CPK; and Anti-alirocumab antibodies.

Visits 16, 18, 20/Week 60, 84, 108 will include the following: Collect AEs; Record concomitant medication; Review patient's diet. Patient should be on a NCEP-ATPIII TLC diet or equivalent; and Data collection on IMP administration and IMP compliance check by review of diary and treatment kit.

Visit 21/Week 120 or June 2016 whichever comes first (end of OLTP treatment) will include the following: Collect AEs; Record concomitant medication; Get body weight measurement; Review patient's diet. Patient should be on a NCEP-ATPIII TLC diet or equivalent; Take vital signs including HR and BP; Perform 12-lead ECG; Perform physical examination; Data collection on IMP administration and IMP compliance check by review of diary and treatment kit accountability; EQ-5D patient questionnaire; Urinalysis (dipstick and if abnormal then microscopy); Urine pregnancy test (women of childbearing potential only); Obtain fasting blood sample for: Lipids: measure and/or calculation of total-C, LDL-C, HDL-C, TG, non-HDL-C, Apo B, Apo A-1, ratio Apo B/Apo A-1, and Lp(a); Hematology: red blood cell count including hematocrit, hemoglobin, red blood cell distribution width (RDW), reticulocyte count, WBC count with differential count and platelets; Chemistry: glucose, sodium, potassium, chloride, bicarbonate, calcium, phosphorous, urea nitrogen, creatinine, uric acid, total protein, albumin, and γGT. HbA1c; Liver panel (ALT, AST, ALP, and total bilirubin); CPK; and Anti-alirocumab antibodies.

The present invention is not to be limited in scope by the specific embodiments described herein. Indeed, various modifications of the invention in addition to those described herein will become apparent to those skilled in the art from the foregoing description and the accompanying figure. Such modifications are intended to fall within the scope of the appended claims.

What is claimed is:

1. A method for reducing low-density lipoprotein cholesterol (LDL-C) in a subject in need thereof comprising:
    (a) selecting a subject with primary hypercholesterolemia who is not taking a statin; and
    (b) administering to the subject a pharmaceutical composition comprising an anti-proprotein convertase subtilisin/kexin type 9 (anti-PCSK9) antibody or antigen-binding fragment thereof at a dose of about 150 mg every 4 weeks for at least 3 doses in the absence of a concomitant statin therapy, wherein the antibody or antigen-binding fragment thereof comprises the heavy and light chain complementarity determining regions (CDRs) of a heavy chain variable region/light chain variable region (HCVR/LCVR) amino acid sequence pair of SEQ ID NOs: 1/6,
    thereby reducing the LDL-C in the subject.

2. The method of claim 1, wherein the antibody or antigen-binding fragment thereof comprises heavy and light chain CDR amino acid sequences having SEQ ID NOs:2, 3, 4, 7, 8, and 10.

3. The method of claim 2, wherein the antibody or antigen-binding fragment thereof comprises an HCVR having the amino acid sequence of SEQ ID NO:1 and an LCVR having the amino acid sequence of SEQ ID NO:6.

4. The method of claim 1, wherein the subject has a form of hypercholesterolemia that is not Familial Hypercholesterolemia (nonFH).

5. The method of claim 1, wherein the subject has heterozygous Familial Hypercholesterolemia (heFH).

6. The method of claim 5, wherein the diagnosis of heFH is made either by genotyping or clinical criteria.

7. The method of claim 6, wherein the clinical criteria is either the Simon Broome Register Diagnostic Criteria for Heterozygous Familial Hypercholesterolemia, or the WHO/Dutch Lipid Network criteria with a score >8.

8. The method of claim 1, wherein the subject is on a non-statin lipid-lowering agent before and/or during administration of the antibody or antigen-binding fragment thereof.

9. The method of claim 8, wherein the non-statin lipid-lowering agent is selected from the group consisting of: ezetimibe, a fibrate, fenofibrate, niacin, an omega-3 fatty acid, and a bile acid resin.

10. The method of claim 9, wherein the non-statin lipid-lowering agent is ezetimibe or fenofibrate.

11. The method of claim 1, wherein the subject is not on a non-statin lipid-lowering agent before and/or during administration of the antibody or antigen-binding fragment thereof.

12. The method of claim 1, wherein the antibody or antigen-binding fragment thereof is administered subcutaneously.

13. The method of claim 1, further comprising the step of (c) administering to the subject one or more following doses of 150 mg of the antibody or antigen-binding fragment thereof about every four weeks if the LDL-C level in the subject after step (b) is lower than 70 mg/dL, or administering one or more following doses of 150 mg of the antibody or antigen-binding fragment thereof about every two weeks if the LDL-C level in the subject after step (b) is greater than or equal to 70 mg/dL.

* * * * *